US008766181B2

(12) United States Patent
Zewail et al.

(10) Patent No.: US 8,766,181 B2
(45) Date of Patent: Jul. 1, 2014

(54) CONTROL IMAGING METHODS IN ADVANCED ULTRAFAST ELECTRON MICROSCOPY

(71) Applicant: California Institute of Technology, Pasadena, CA (US)

(72) Inventors: Ahmed H. Zewail, Pasadena, CA (US); John Spencer Baskin, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 13/893,054

(22) Filed: May 13, 2013

(65) Prior Publication Data
US 2014/0131574 A1 May 15, 2014

Related U.S. Application Data

(60) Provisional application No. 61/646,069, filed on May 11, 2012, provisional application No. 61/651,467, filed on May 24, 2012, provisional application No. 61/651,413, filed on May 24, 2012, provisional application No. 61/651,439, filed on May 24, 2012, provisional application No. 61/661,941, filed on Jun. 20, 2012.

(51) Int. Cl.
*H01J 37/26* (2006.01)
*H01J 37/22* (2006.01)
*G01N 23/00* (2006.01)

(52) U.S. Cl.
CPC ................. *H01J 37/26* (2013.01); *G01N 23/00* (2013.01); *H01J 37/22* (2013.01); *H01J 37/226* (2013.01); *H01J 2237/2482* (2013.01)
USPC ............ 250/306; 250/307; 250/310; 250/311

(58) Field of Classification Search
CPC .. H01J 37/22; H01J 37/226; H01J 2237/2482
See application file for complete search history.

(56) References Cited

U.S. PATENT DOCUMENTS

| 4,474,446 | A | * | 10/1984 | Reynolds et al. | 396/111 |
| 4,972,075 | A | * | 11/1990 | Hamada et al. | 250/201.5 |
| 4,984,229 | A | * | 1/1991 | Nedvidek | 369/44.24 |
| 5,688,262 | A | * | 11/1997 | Abraham | 606/18 |
| 6,107,600 | A | * | 8/2000 | Kurosawa | 219/121.8 |
| 6,724,486 | B1 | | 4/2004 | Shull et al. | |
| 7,915,583 | B2 | * | 3/2011 | Zewail et al. | 250/310 |
| 8,203,120 | B2 | * | 6/2012 | Zewail | 250/310 |

(Continued)

OTHER PUBLICATIONS

U.S. Appl. No. 13/890,667, filed May 9, 2013 by Zewail et al. (Unpublished. Copy available via USPTO's IFW System).

(Continued)

*Primary Examiner* — Jack Berman
*Assistant Examiner* — James Choi
(74) *Attorney, Agent, or Firm* — Kilpatrick Townsend & Stockton LLP

(57) ABSTRACT

An optical system includes a beam splitter disposed along an optical axis and a set of mirrors optically coupled to the beam splitter. The set of mirrors are oriented perpendicular to each other. The optical system also includes a turning mirror optically coupled to a second mirror of the set of mirrors and a detector optically coupled to the turning mirror.

17 Claims, 25 Drawing Sheets

(56) References Cited

U.S. PATENT DOCUMENTS

| | | |
|---|---|---|
| 8,247,769 B2 * | 8/2012 | Zewail .......................... 250/311 |
| 8,429,761 B2 * | 4/2013 | Zewail et al. .................... 850/30 |
| 8,440,970 B2 * | 5/2013 | Zewail .......................... 250/307 |
| 2002/0118422 A1 * | 8/2002 | Cao ............................... 359/161 |
| 2003/0004412 A1 | 1/2003 | Izatt et al. |
| 2003/0030897 A1 | 2/2003 | Suzuki |
| 2003/0231390 A1 * | 12/2003 | Wein et al. .................... 359/495 |
| 2004/0195497 A1 | 10/2004 | Sasaki |
| 2005/0001176 A1 | 1/2005 | Loney et al. |
| 2006/0269273 A1 * | 11/2006 | Okumura ....................... 396/296 |
| 2007/0153273 A1 | 7/2007 | Meeks |
| 2008/0278813 A1 * | 11/2008 | Wilklow ........................ 359/495 |
| 2009/0207409 A1 * | 8/2009 | Yao ............................... 356/365 |
| 2009/0236521 A1 * | 9/2009 | Zewail et al. ................. 250/307 |
| 2010/0016688 A1 * | 1/2010 | Debreczeny et al. .......... 600/310 |
| 2010/0088787 A1 * | 4/2010 | Shigekawa et al. ............... 850/6 |
| 2010/0108883 A1 | 5/2010 | Zewail |
| 2011/0103816 A1 * | 5/2011 | Mitsuoka ......................... 399/67 |
| 2011/0196350 A1 | 8/2011 | Friedman et al. |
| 2011/0220792 A1 | 9/2011 | Zewail et al. |
| 2011/0255088 A1 * | 10/2011 | Dane et al. ..................... 356/370 |
| 2011/0275932 A1 * | 11/2011 | Leblond et al. ................ 600/425 |

OTHER PUBLICATIONS

Notification of Transmittal of the International Search Report and the Written Opinion of the International Searching Authority, or the Declaration and International Search Report and Written Opinion of the International Searching Authority for International Application No. PCT/US2013/040432 mailed on Sep. 13, 2013, 10 pages.

\* cited by examiner

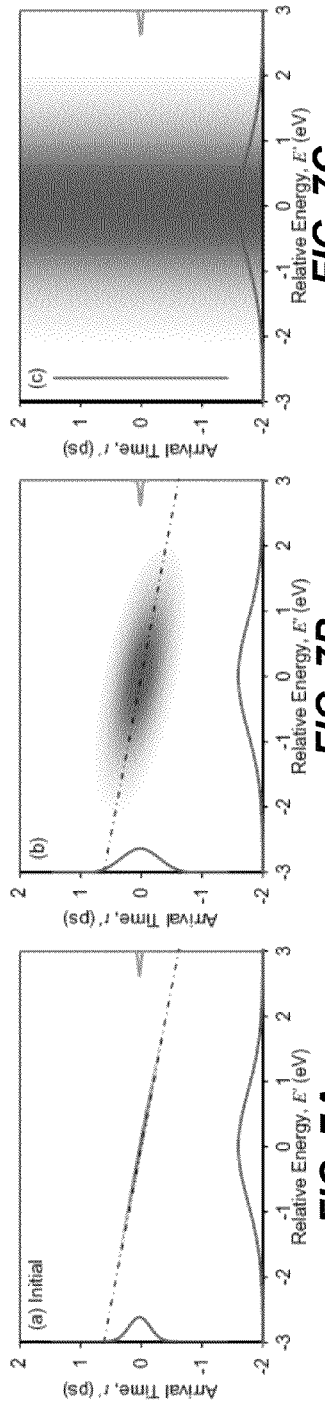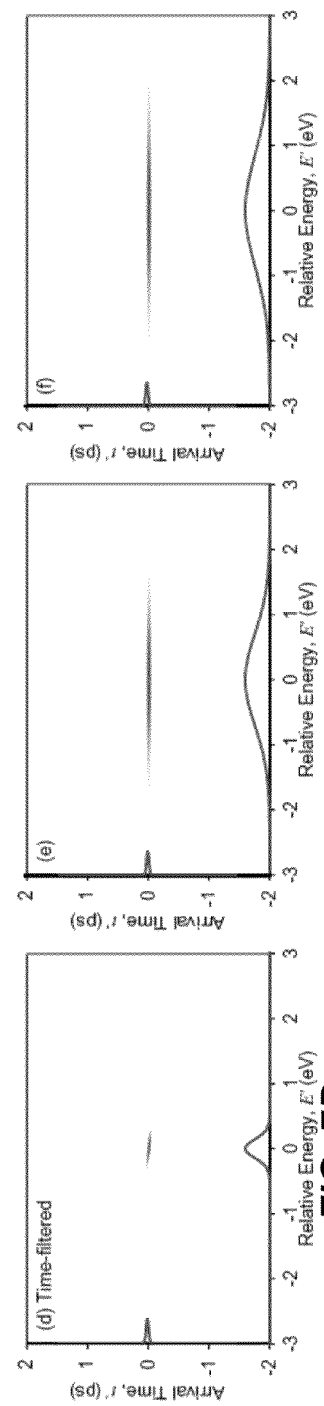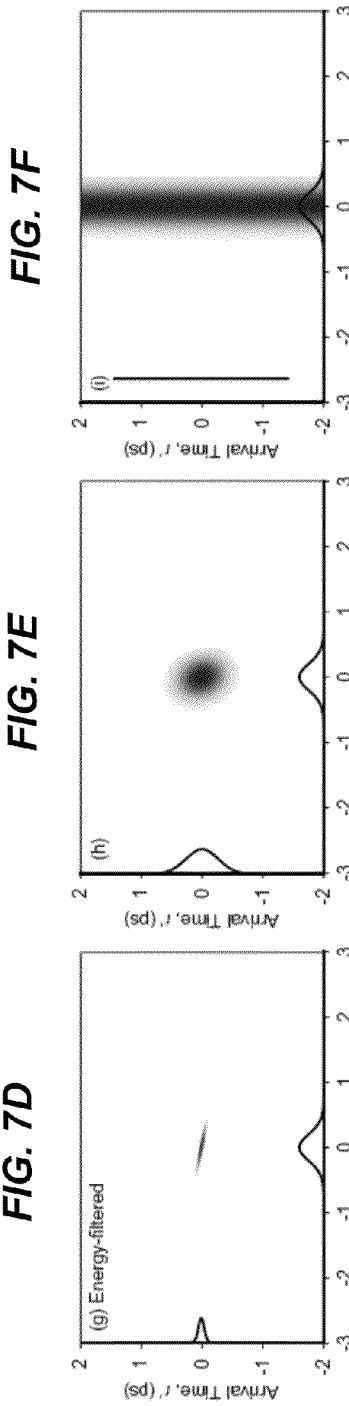
FIG. 7A FIG. 7B FIG. 7C
FIG. 7D FIG. 7E FIG. 7F
FIG. 7G FIG. 7H FIG. 7I

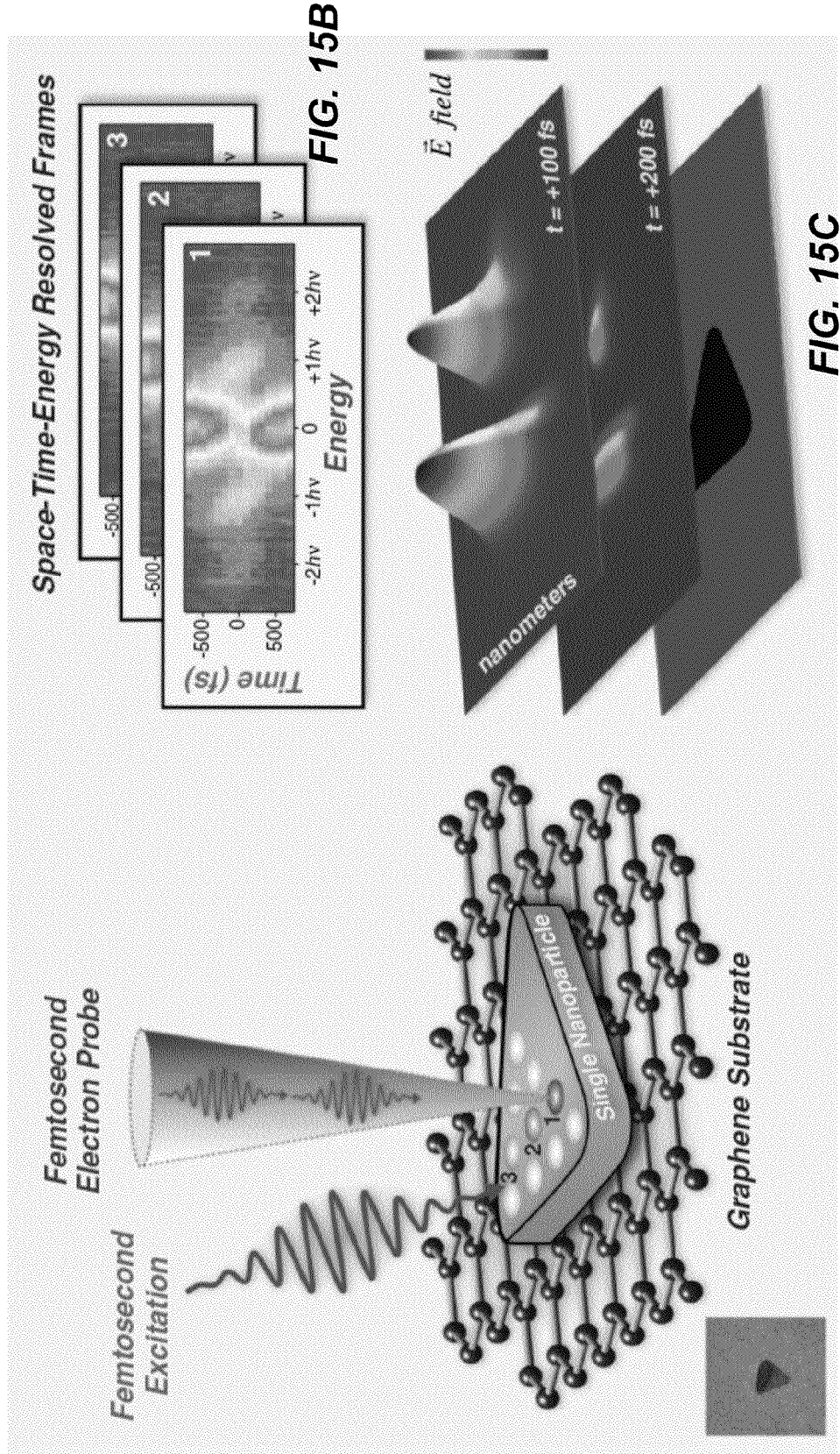

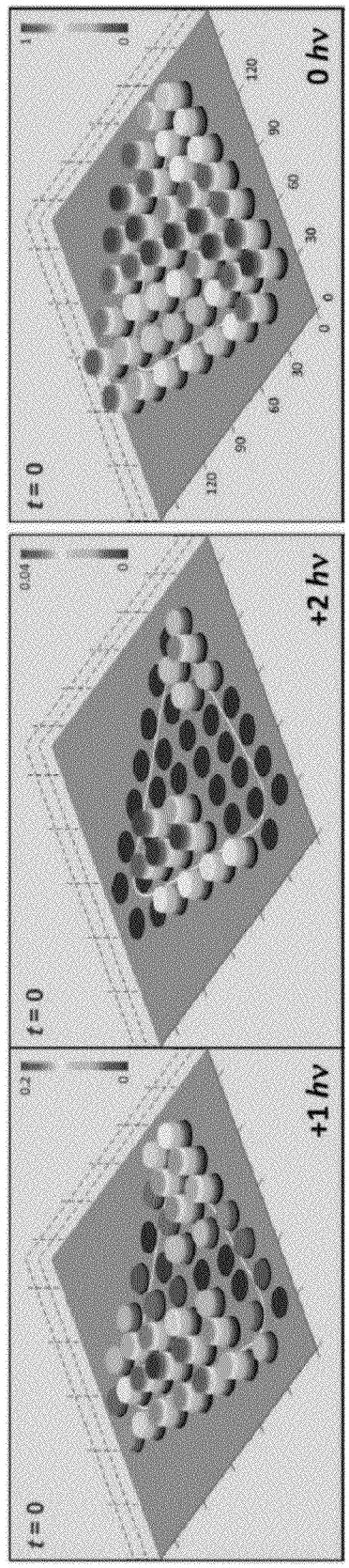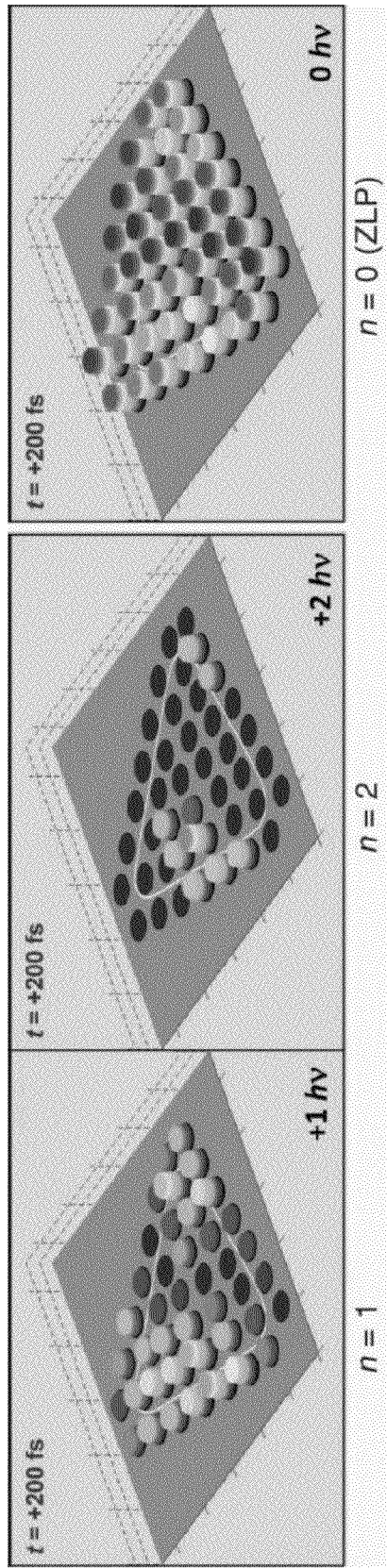
FIG. 16A  FIG. 16C  FIG. 16E
FIG. 16B  FIG. 16D  FIG. 16F

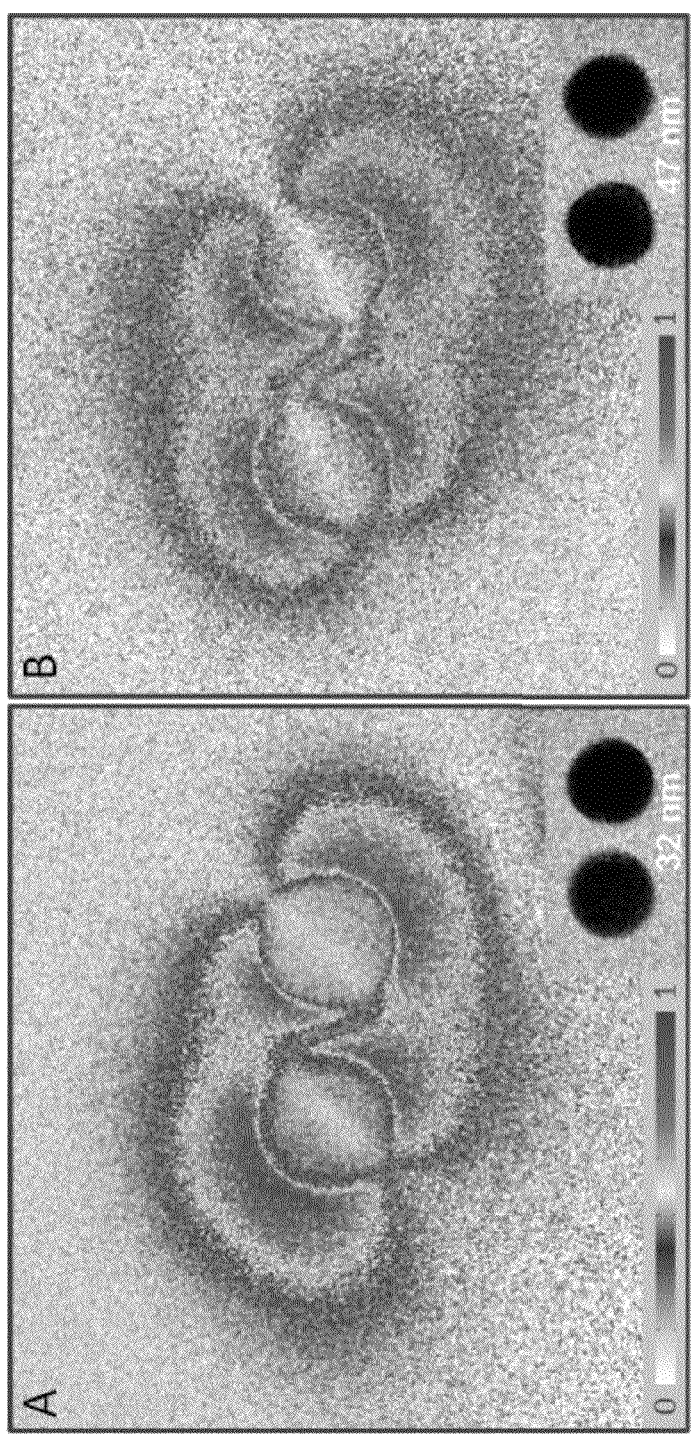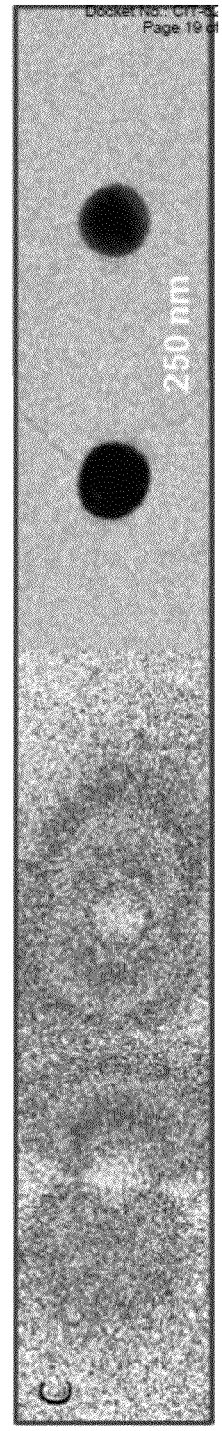
FIG. 19A
FIG. 19B
FIG. 19C

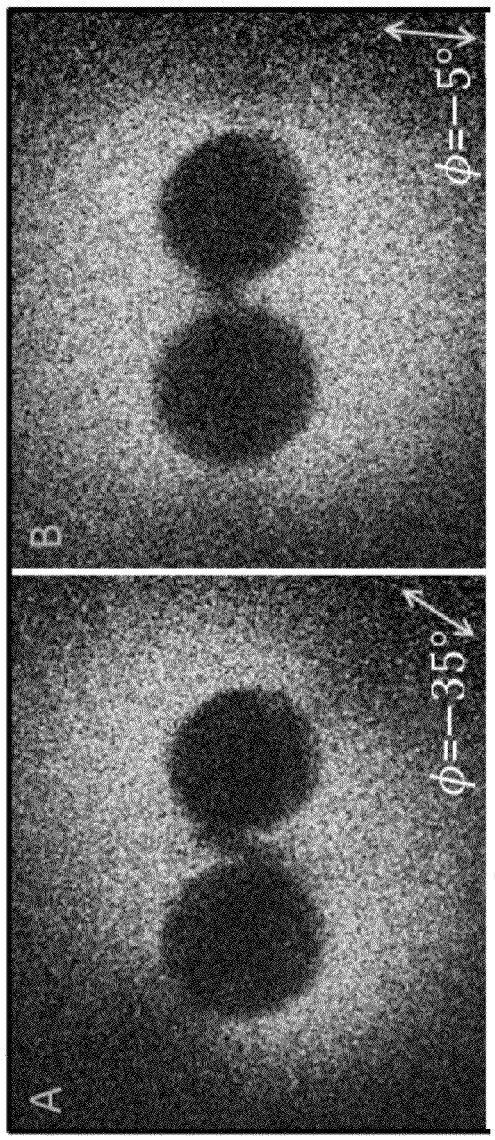
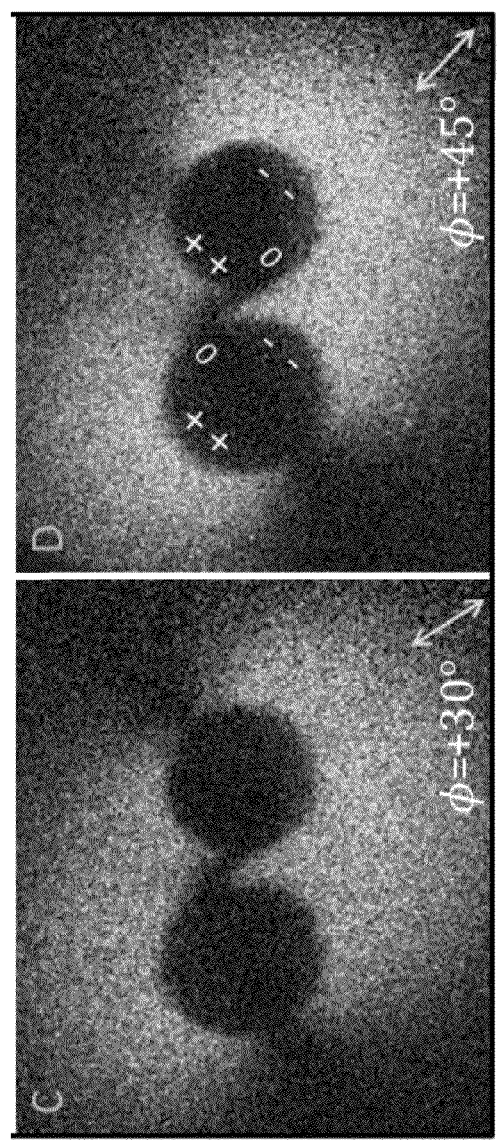
FIG. 20A  FIG. 20B  FIG. 20C  FIG. 20D

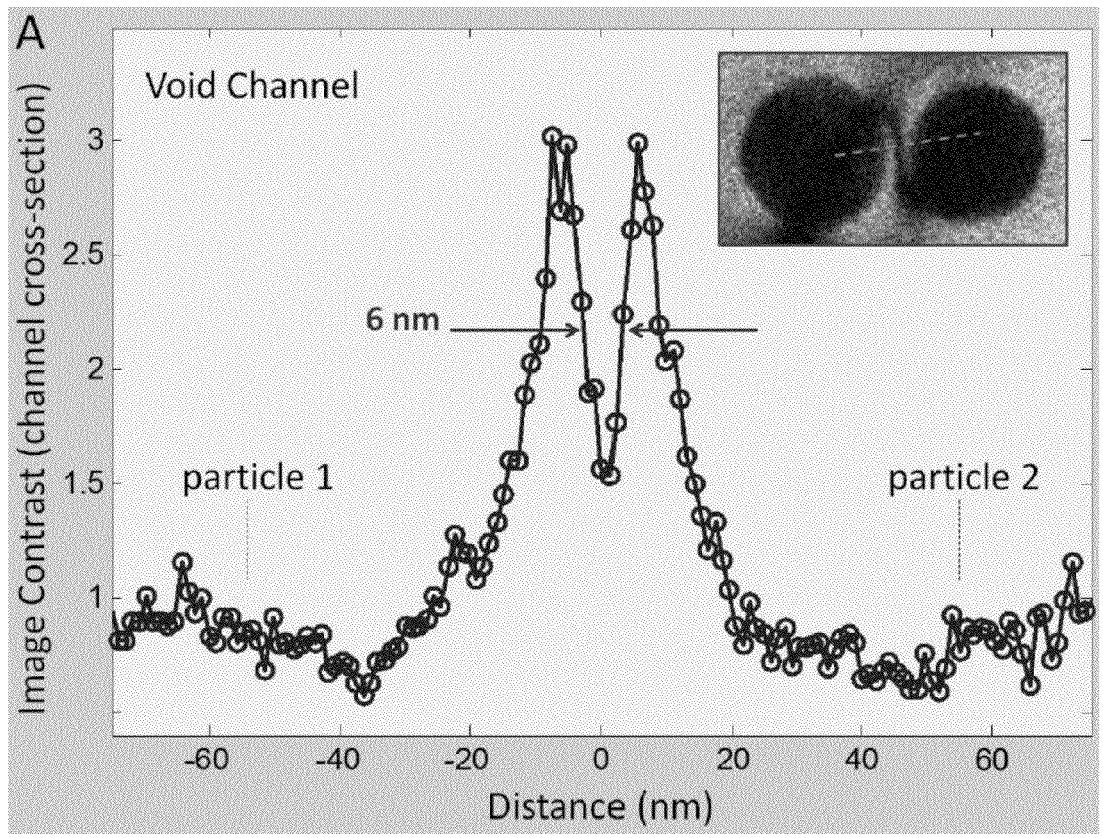
FIG. 21A
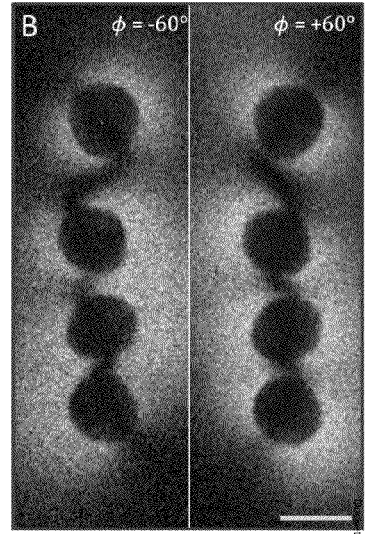
FIG. 21B  FIG. 21C

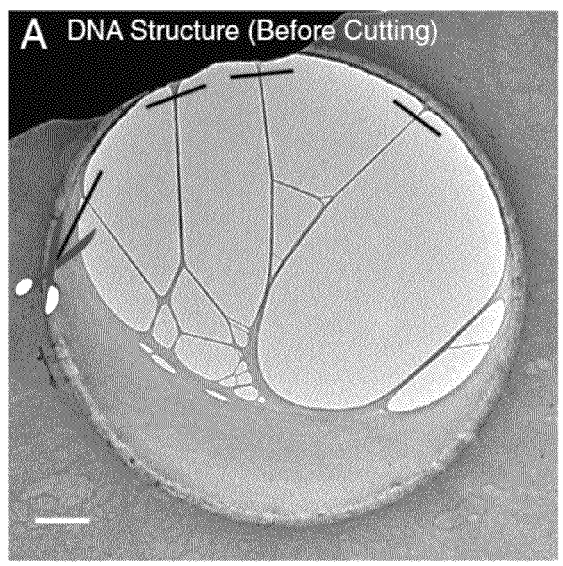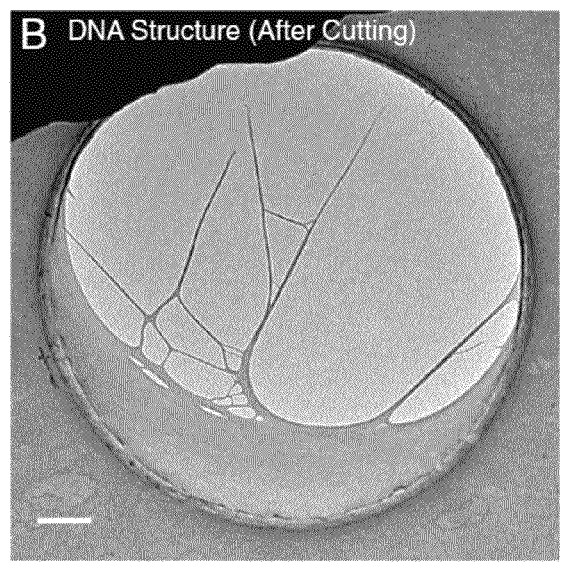
*FIG. 23A*  *FIG. 23B*

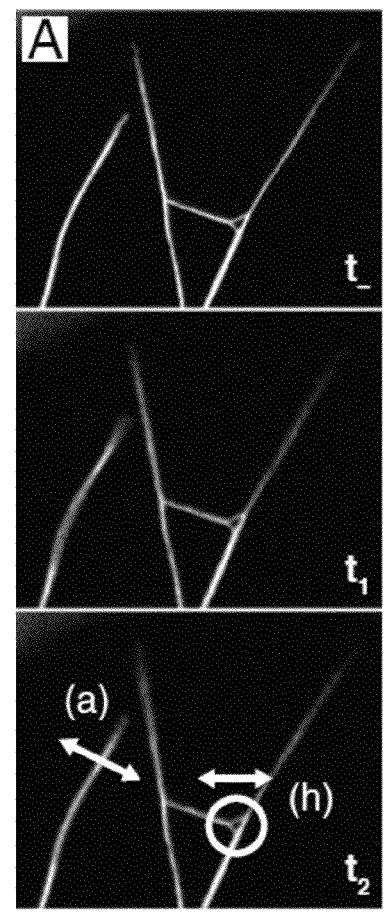
FIG. 24A
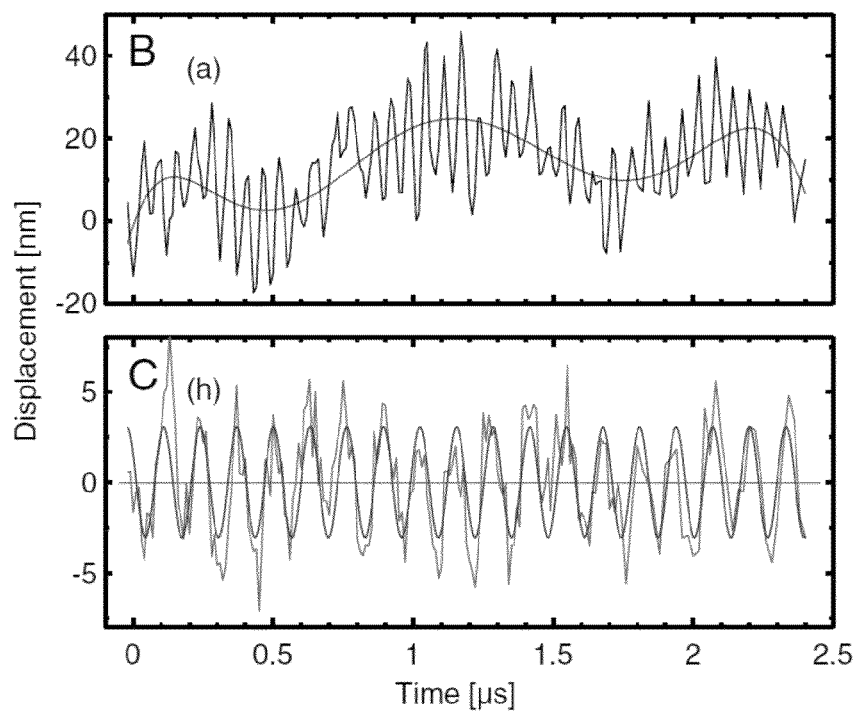
FIG. 24B
FIG. 24C

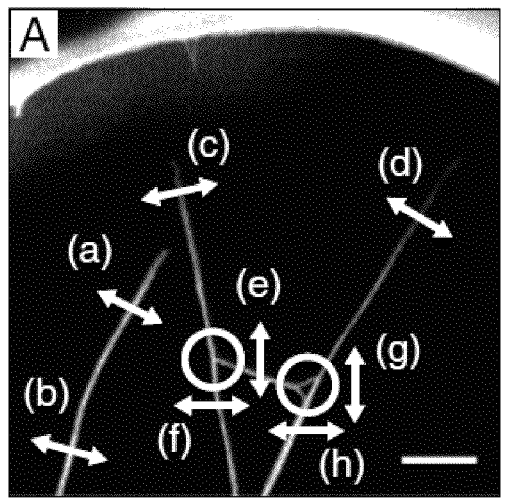
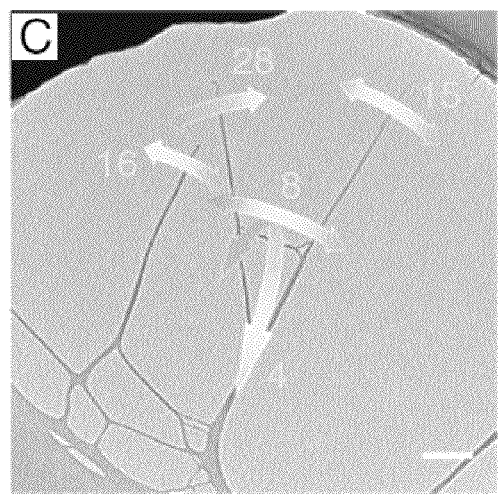
FIG. 25A
FIG. 25B
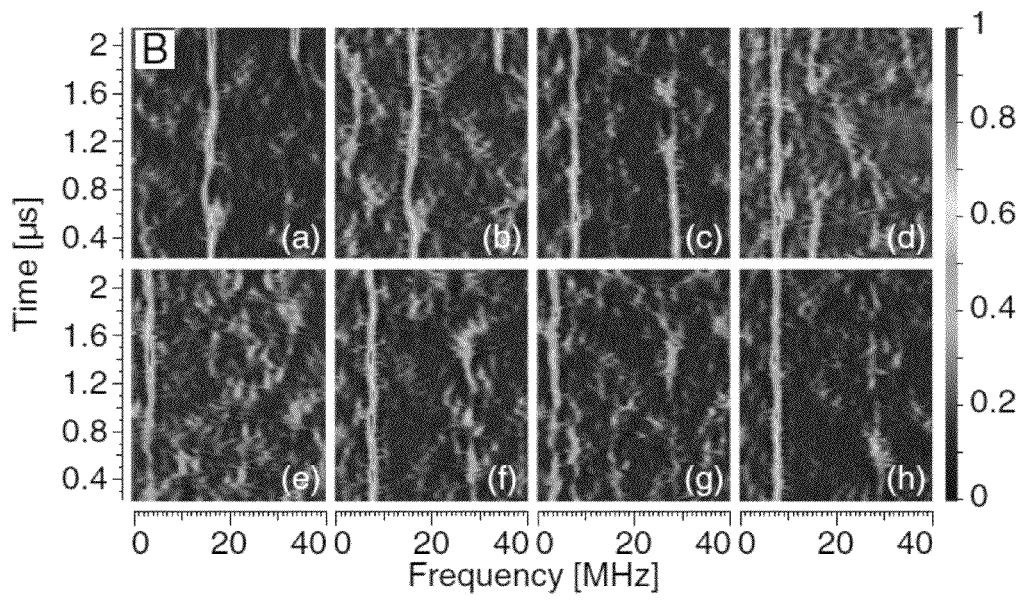
FIG. 25C

CONTROL IMAGING METHODS IN ADVANCED ULTRAFAST ELECTRON MICROSCOPY

CROSS-REFERENCES TO RELATED APPLICATIONS

This application claims the benefit of U.S. Provisional Patent Application No. 61/646,069, filed May 11, 2012, entitled "Imaging Apparatus for Real-Time Tracking and Control of Laser Spatial Distribution and Fluence in an Ultrafast Electron Microscope," and U.S. Provisional Patent Application No. 61/651,467, filed May 24, 2012, entitled "Second-generation 4D Ultrafast Electron Microscope," U.S. Provisional Patent Application No. 61/651,413, filed May 24, 2012, entitled "Gating Chirped-Pulses and Enhancing Contrast in Ultrafast Electron Microscope," U.S. Provisional Patent Application No. 61/651,439, filed May 24, 2012, entitled "Sub-particle Imaging, Particle Entanglement, and Particle Trapping," and U.S. Provisional Patent Application No. 61/661,941, filed on Jun. 20, 2012, entitled "Channels of Entangled Nanoparticles Discovered by Visualization in Space and Time," the disclosures of which are hereby incorporated by reference in their entirety.

STATEMENT AS TO RIGHTS TO INVENTIONS MADE UNDER FEDERALLY SPONSORED RESEARCH OR DEVELOPMENT

This invention was made with government support under FA9550-11-1-0055 awarded by the Air Force and under DMR0964886 awarded by the National Science Foundation. The government has certain rights in the invention.

BACKGROUND OF THE INVENTION

Electrons, because of their wave-particle duality, can be accelerated to have picometer wavelength and focused to image in real space. With the impressive advances made in transmission electron microscopy (TEM), STEM, and aberration-corrected TEM, it is now possible to image with high resolution, reaching the sub-Angstrom scale. Together with the progress made in electron crystallography, tomography, and single-particle imaging, today the electron microscope has become a central tool in many fields, from materials science to biology.

For many microscopes, the electrons are generated either thermally by heating the cathode or by field emission, and as such the electron beam is made of random electron bursts with no control over the temporal behavior. In these microscopes, time resolution of milliseconds or longer, being limited by the video rate of the detector, can be achieved, while maintaining the high spatial resolution.

Despite the advances made in TEM techniques, there is a need in the art for improved methods and novel systems for ultrafast electron microscopy.

SUMMARY OF THE INVENTION

According to embodiments of the present invention, methods and systems related to microscopy are provided. In a particular embodiment, an optical system utilized with an electron microscope enables the excitation laser energy distribution to be monitored and controlled using a replica beam path. More particularly, a set of reflective elements are utilized in the replica beam path which have an optical path length equal to the specimen path.

The second-generation 4D ultrafast electron microscope (4D UEM-2) developed by the inventors features a hybrid 200-kV TEM designed for pulsed imaging measurements by integration of either femtosecond (fs) or nanosecond (ns) laser pulses to the cathode and simultaneously to the specimen, through two ports allowing optical access into the TEM column. It is straightforward to switch (by flipping two mirrors) between the laser systems to cover both the fs and ns domains enabling single-electron and single pulse (millions of electrons) 4D imaging.

The microscope may be equipped for a number of powerful variant techniques of electron microscopy, including real-space imaging, diffraction, Electron Energy Loss Spectroscopy (EELS), Electron Energy Gain Spectroscopy (EEGS), scanning transmission electron spectroscopy (STEM), and environmental, bright (dark) field, imaging. FIG. 28 is a simplified schematic diagram illustrating an advanced ultrafast electron microscope according to an embodiment of the present invention.

Laser light pulses are used to either heat or excite the thin film specimens in the microscope column, and ultraviolet laser pulses directed at the lanthanum hexaboride ($LaB_6$) cathode create electron packets that replace the usual TEM continuous and chaotic electron beam for observing the specimen response. The delay between the optical and electron pulse arrival at the specimen defines the time axis for imaging, and is fixed by a computer-controlled optical delay line (fs mode) or electronic delay generator (ns mode).

Images, diffraction patterns, or energy gain or loss spectra may be constructed stroboscopically, in seconds, by a train of optical and electron pulses, which repetitively excite and probe, respectively, a reversible dynamic process in the nano-film specimen. In the case of irreversible specimen changes, single ns electron pulses may instead be used to capture diffraction images at selected time delays following excitation. The size of the electron packets can be varied from one electron for highest temporal and energy resolutions to enough electrons to provide the capability of single pulse recording. The laser repetition rates are also variable, from single shot to the megahertz range, to allow a balance between the high data acquisition rate required in the single electron limit and the specimen-dependent minimum recovery time following an excitation pulse. The latter ranges from microseconds to milliseconds for typical thin-film specimens.

According to an embodiment of the present invention, an optical system is provided. The optical system includes a beam splitter disposed along an optical axis and a set of mirrors optically coupled to the beam splitter. The set of mirrors are oriented perpendicular to each other. The optical system also includes a turning mirror optically coupled to a second mirror of the set of mirrors and a detector optically coupled to the turning mirror.

According to another embodiment of the present invention, a microscope system is provided. The microscope system includes a microscope column, a laser system operable to provide a laser beam, and an electron beam path disposed within the microscope column. The microscope system also includes a window disposed in the microscope column and a laser beam path disposed within the microscope column. Both the electron beam path and the laser beam path impinge on a specimen disposed in the microscope column at a predetermined position. The microscope system further includes an optical system mounted in a fixed relationship to the window. The optical system includes a beam splitter operable to receive the laser beam, pass a first portion of the laser beam to the laser beam path, and pass a second portion of the laser beam along a detection path, a set of mirrors operable to receive a second portion of the laser beam, a turning mirror coupled to the set of mirrors, and a detector. The detection path impinges on the detector at a second predetermined position correlated to the predetermined position.

According to a specific embodiment of the present invention, a method of imaging a specimen is provided. The method includes providing a stage assembly configured to support the specimen, generating a first train of optical pulses from a first laser source, and directing the first train of optical pulses along an optical path to impinge on a cathode. The method also includes generating a train of electron pulses in response to the first train of optical pulses impinging on the cathode, directing the train of electron pulses along an imaging path to impinge on the specimen, and generating a second train of optical pulses from a second laser source. The method further includes splitting the second train of optical pulses into a specimen path and a detection path. The specimen path and the detection path have equal optical path lengths. Moreover, the method includes directing the optical pulses in the specimen path to impinge on the specimen, directing the optical pulses in the detection path to impinge on a detector, and detecting at least a portion of the train of electron pulses passing through the specimen.

Numerous benefits are achieved by way of the present invention over conventional techniques. For example, embodiments of the present invention provide methods and systems that enable the ability to allow measurement in real-time during experiments—on arbitrary samples—the position, size, shape, and intensity of the laser spot on the specimen, for example, for spot sizes down to and below 20 μm FWHM. Additionally, embodiments enable the accommodation of widely varying laser conditions of wavelength, polarization, power and focus, used for both single pulse and stroboscopic measurements. Moreover, embodiments incorporate positioning adjustment ranges covering all possible laser input alignments, with wide acceptance angle for flexibility and ease of operation. Furthermore, embodiments allow for the removal and reinstallation of the tracking and control system (also referred to as an imaging apparatus) without loss of alignment. These and other embodiments of the invention along with many of its advantages and features are described in more detail in conjunction with the text below and attached figures.

BRIEF DESCRIPTION OF THE DRAWINGS

FIGS. 7A-I illustrate population density plots according to an embodiment of the present invention.

FIGS. 15A-C illustrate a schematic for a system for ultrafast spectrum imaging according to an embodiment of the present invention.

FIGS. 16A-F illustrate USI time and order frames for a plasmonic triangular particle according to an embodiment of the present invention.

FIGS. 19A-C illustrate entangled particles by dipolar fields and nanometer-scale void-channels according to an embodiment of the present invention.

FIGS. 20A-D illustrate the polarization dependence of the entanglement according to an embodiment of the present invention.

FIGS. 21A-C illustrate the spatial extent of entanglement and channels of particle chains according to an embodiment of the present invention.

FIGS. 23A-B illustrate electron micrographs of a DNA nanostructure according to an embodiment of the present invention.

FIGS. 24A-C illustrates the transient behavior of the DNA nanostructure following laser excitation according to an embodiment of the present invention.

FIGS. 25A-C illustrates the vibrational properties of the DNA nanostructure according to an embodiment of the present invention.

DETAILED DESCRIPTION OF SPECIFIC EMBODIMENTS

Embodiments of the present invention provide methods and systems related to microscopy. In a particular embodiment, an optical system utilized with an electron microscope enables the excitation laser energy distribution to be monitored and controlled using a replica beam path. More particularly, a set of reflective elements are utilized in the replica beam path which have an optical path length equal to the specimen path.

In Ultrafast Electron Microscopy (UEM), a specimen with structures of dimensions from Angstroms to microns under observation in a transmission electron microscope (TEM) is subjected to excitation by a temporally short, tightly focused laser pulse, and the structures dynamic response to this excitation pulse is observed and recorded, with time and spatial resolutions appropriate to the dynamics under study (down to femtosecond and Angstrom, respectively). The nature of the response is in most cases strongly dependent on the microscopic distribution of the excitation, or pump energy, on the specimen, relative to the area under observation; hence a knowledge of this fluence distribution is useful to a complete quantitative understanding of the process.

Although embodiments of the present invention are discussed in relation to UEM implementations (particularly 4D UEM), this is not required by the present invention and embodiments of the present invention can be utilized in conjunction with 2D electron microscope systems (including field emission configurations) as well as the UEM systems discussed herein. As an example, the characteristics of an excitation laser beam can be observed and controlled in a variety of electron microscopy implementations. One of ordinary skill in the art would recognize many variations, modifications, and alternatives.

Figure 1:
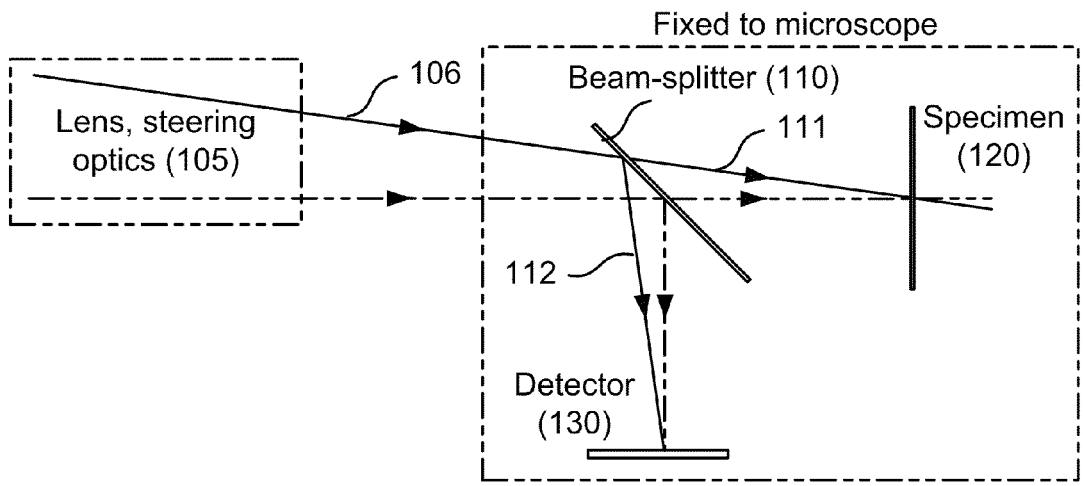
FIG. 1 is a simplified schematic diagram illustrating specimen and detector optical paths according to an embodiment of the present invention.

In order to monitor the laser properties at the specimen, a combination of a beam-splitter and a high-resolution CCD detector are used in embodiments described herein. FIG. 1 is a simplified schematic diagram illustrating specimen and detector optical paths according to an embodiment of the present invention. As illustrated in FIG. 1, the beam-splitter 110 is fixed to the microscope in the excitation beam path of a laser beam 106 after the focusing lens and steering optics (105), and the detector surface (130) is placed in coincidence with the plane which is conjugate to the microscope specimen plane (120) for reflection in the beam-splitter. Each position on the detector then maps a unique position on the specimen, and the detected laser spot replicates the spatial properties of the excitation distribution on the specimen. For direct characterization of the focused spot, a detector pixel size of 4.4 µm was chosen although embodiments can utilize other pixel sizes including smaller or larger pixel sizes.

Referring to FIG. 1, a basic operating principle of embodiments of the present invention is that the spatial relationship between the various system elements is such that the beam splitter 105 that creates two optical paths 111 and 112 extending to the specimen 120 and detector 130, respectively. Optical paths 111 and 112 have equal path lengths (i.e., optical path lengths). As a result, spatial elements imaged at the detector are correlated with the spatial elements associated with the sample. For both alignments of the laser beam illustrated in FIG. 1 (solid and dashed lines), equal path lengths are provided. Additionally, for impingement of the laser beam on different portions of the specimen, impingement on corresponding portions of the detector will be observed. Thus, for varying alignments of the laser beam 106 into the apparatus for a single location on the specimen (also referred to as a sample), the laser beam impinges on a corresponding single location on the detector. Accordingly, a one-to-one spatial mapping is provided between the specimen and the detector.

Typical UEM experiments utilize excitation powers and focusing such that, to avoid saturation and damage to the CCD, the replica image on the CCD detector is many orders of magnitude weaker than the fluence actually applied to the specimen. To achieve this attenuation and preserve the beam focus with minimal sensitivity to the properties of the excitation laser used (for example, wavelength, polarization, incidence angle, and the like) front surface reflections on four uncoated fused silica surfaces, including the beam-splitter, are introduced in the replica beam path (i.e., the path to the detector, which can also be referred to as a detection path). As described more fully herein, using embodiments of the present invention, the spatial distribution of the excitation laser beam on the specimen (as well as other characteristics) can be measured and controlled. Accordingly, temperature profiles (based on the intensity and spatial distribution of the excitation beam, i.e., the fluence) can be predicted, confirmed, and controlled. In particular implementations, the shot-to-shot characteristics of the excitation laser beam can be monitored and controlled, enabling, for example, characterization of phase transitions using temperature information available through embodiments of the present invention. Additionally, the polarization of the excitation beam can be measured and controlled.

Figure 2A:
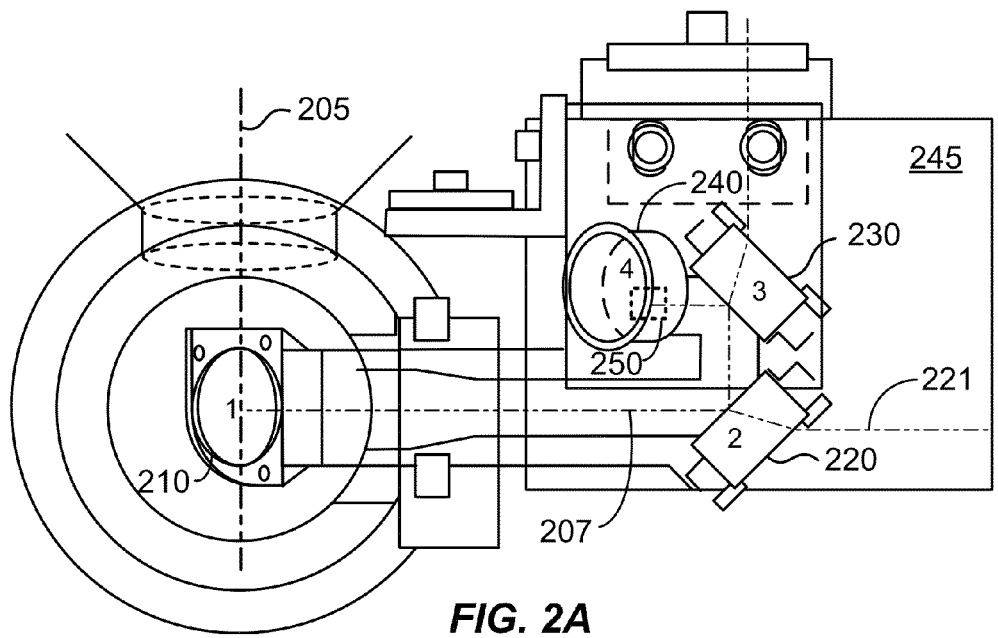
FIG. 2A is a simplified schematic diagram illustrating arrangement of optical elements in a tracking and control system according to an embodiment of the present invention.
Figure 2B:
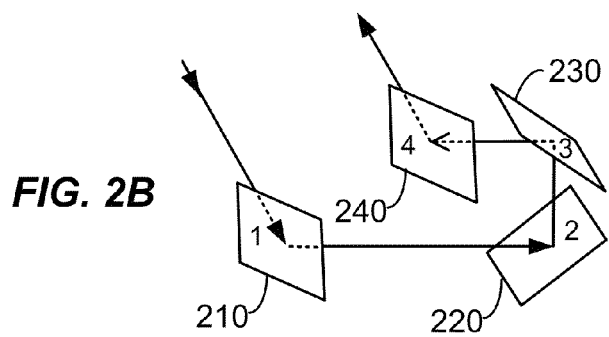
FIG. 2B is a simplified perspective diagram illustrating spatial layout of the optical elements shown in FIG. 2A.

FIG. 2A is a simplified schematic diagram illustrating arrangement of optical elements in a tracking and control system according to an embodiment of the present invention. The view in FIG. 2A is a cutaway view of the assembled apparatus, as viewed looking along the axis of the incoming laser as it passes the beam-splitter 210. FIG. 2B illustrates an off-axis view of the orientation of the four reflecting surfaces chosen to provide compensation for reflected intensity dependence on polarization and incidence-angle as described more fully below. The axial ray of the system is incident at 45° on each surface. Any tilted ray with an angle of incidence >45° on one surface will have an angle of incidence <45° on a second surface.

By utilizing a common optical path length for the specimen and detection paths, the image on the detector is an image of the specimen. In this way, the detector plane becomes a surrogate for the specimen plane. Accordingly, it is possible to map points on the detector and correlate these points to corresponding points or objects in the specimen plane. In other words, the pixels of the detector (e.g., the pixels of a CCD camera) each corresponds to a certain point on the specimen. As a significant benefit, since the size of the laser beam (i.e., the beam waist) at the specimen and the detector are the same, the detector provides information on the beam dimensions, and thereby the intensity at the specimen. As described herein, impingement of the laser beam on the detector represents or correlates with the impingement of the laser beam on a correlated position (e.g., the same place) on the specimen. Accordingly, the characteristics of the laser beam, including the fluence, beam waist, polarization, and the like, can be characterized using the tracking and control system without imaging of the sample. Drifting of the laser beam can be tracked and corrected in real-time using embodiments of the present invention. Thus, in contrast with conventional systems, monitoring and control of the excitation laser properties enables applications of the microscope system, particularly in long-term measurements that benefit from control of drift of the laser characteristics including fluence, polarization, beam size, and the like. As examples, measurements described herein benefit from the capabilities provided by embodiments of the present invention.

Conventionally, a separate imaging system will be used to image the specimen and determine the beam characteristics at the specimen. In contrast, embodiments of the present invention utilize a design in which the spatial relationships and optical distances are the same for both paths, enabling collection of information related to the beam at the specimen without imaging of the specimen, but by observations of the correlated beam at the detector. Calibration of the tracking and control system can be performed by burning or otherwise creating features into a sample while measuring the laser beam at the detector and correlating the features on the sample to the measured images collected using the detector.

In some embodiments, the tracking and control system is referred to as an apparatus or an optical system. Laser beam 205 is incident on beam splitter 210. In an embodiment, the beam splitter 210 is an uncoated fused silica flat with relatively low reflectance (e.g., a few percent such as from about 1% to about 8% depending on polarization among other factors). The thickness of the beam splitter ranges from about 1 mm to about 5 mm, for example, 3 mm although these particular dimensions are not limiting to the present invention. Other suitable beam splitters can be utilized as will be evident to one of skill in the art.

After reflection from beam splitter 210, light propagates along optical path 207 and is incident on mirror 2 (220). Although "mirrors," including mirror 2, mirror 3, and mirror 4 are discussed herein, it should be understood that these mirrors are typically characterized by low reflectances. In some embodiments, materials suitable for windows in other applications, for example, flat pieces of uncoated fused silica, are utilized as the "mirrors" discussed herein. Coatings can also be utilized in some embodiments. One of ordinary skill in the art would recognize many variations, modifications, and alternatives.

Referring to FIG. 2A, since the reflectance of the mirrors is low (e.g., a few percent), most of the light incident on the mirrors passes through the mirrors without reflection as illustrated by light beam 221. In some implementations, the light passing through the mirrors (e.g., light in light beam 221) is utilized in aligning the apparatus and the optical elements of the apparatus. By providing only a few percent reflection at each mirror, the initial beam reflected from the beam splitter is attenuated by the apparatus, providing a low fluence beam at the detector.

After reflections off mirror 2 (220), mirror 3 (230), and mirror 4 (240), the light is incident on detector 250, which is disposed behind the plane of the figure and mounted in detector housing 245.

Referring to FIG. 2A, the thickness of mirror 2, mirror 3, and mirror 4 is selected (e.g., the thickness of the uncoated fused silica windows) such that reflections off of the back surface of the mirror are spatially separated from the reflections off the front surface such that the back reflections are not able to pass through the apertures of the optical system. The thickness of the mirrors ranges from about 10 mm to about 16 mm, for example, 13 mm although these particular dimensions are not limiting to the present invention. Other suitable mirrors can be utilized as will be evident to one of skill in the art.

In some embodiments, the optical elements are mounted in the apparatus in a fixed manner such that they are not individually adjustable after mounting. The apparatus is adjustable with respect to the microscope column. The light passing through mirror 2 and mirror 3 can be used to align these optical elements during the mounting process.

FIG. 2B is a simplified perspective diagram illustrating spatial layout of the optical elements shown in FIG. 2A. The surfaces of the optical elements are illustrated, with a portion of the input beam reflecting off of beam splitter 210, reflecting off mirror 2 (220) at a right angle, then reflecting off mirror 3 (230) in a direction opposite to the direction the light is propagating after reflection off of the beam splitter. Mirror 4 (240) is then used to reflect the beam into the detector. The angle of incidence for the beam splitter, mirror 2, mirror 3, and mirror 4 is 45° in order to provide for polarization compensation as described more fully below.

The four reflections provided by the beam splitter and mirrors 2-4 result in polarization compensation. As illustrated, two S reflections and two P reflections are produced because of the polarization difference. Because 2 S and 2 P reflections are provided, regardless of the input polarization, the same intensity is produced at the detector. The arrangement of the beam splitter and the three mirrors is selected to achieve 2 S and 2 P reflections as well as equal optical path lengths for the specimen and detection paths. The nominal axial alignment is 45° degrees on each of the mirror surfaces (to achieve 2 S and 2 P reflections). However, if the alignment is greater than 45° on one of the S reflection mirrors (e.g., mirror 2), it will be less than 45° on the other S reflection mirror (e.g., mirror 3), which contributes to the polarization compensation since the reflectance is sensitive to angle, especially around 45°, which can be near Brewster's Angle.

Referring to FIG. 2A, if the polarization is S at beam splitter 210 (vertically aligned polarization), then the polarization will be P at mirror 2 (220). After reflection from mirror 2, the polarization will be aligned with the plane of the figure, result in P polarization at mirror 3 (230). After reflection off mirror 3, the polarization will be vertical again, resulting in S polarization at mirror 4 (240). In this example, the polarizations for the four reflections are S-P-P-S, which provides the 2 S and 2 P reflections desired. For an initial P polarization, the four reflections will be P-S-S-P for reasons similar to those explained above. Of course, these are just examples and other configurations achieving 2 S and 2 P reflections are included within the scope of the present invention.

Figure 3:
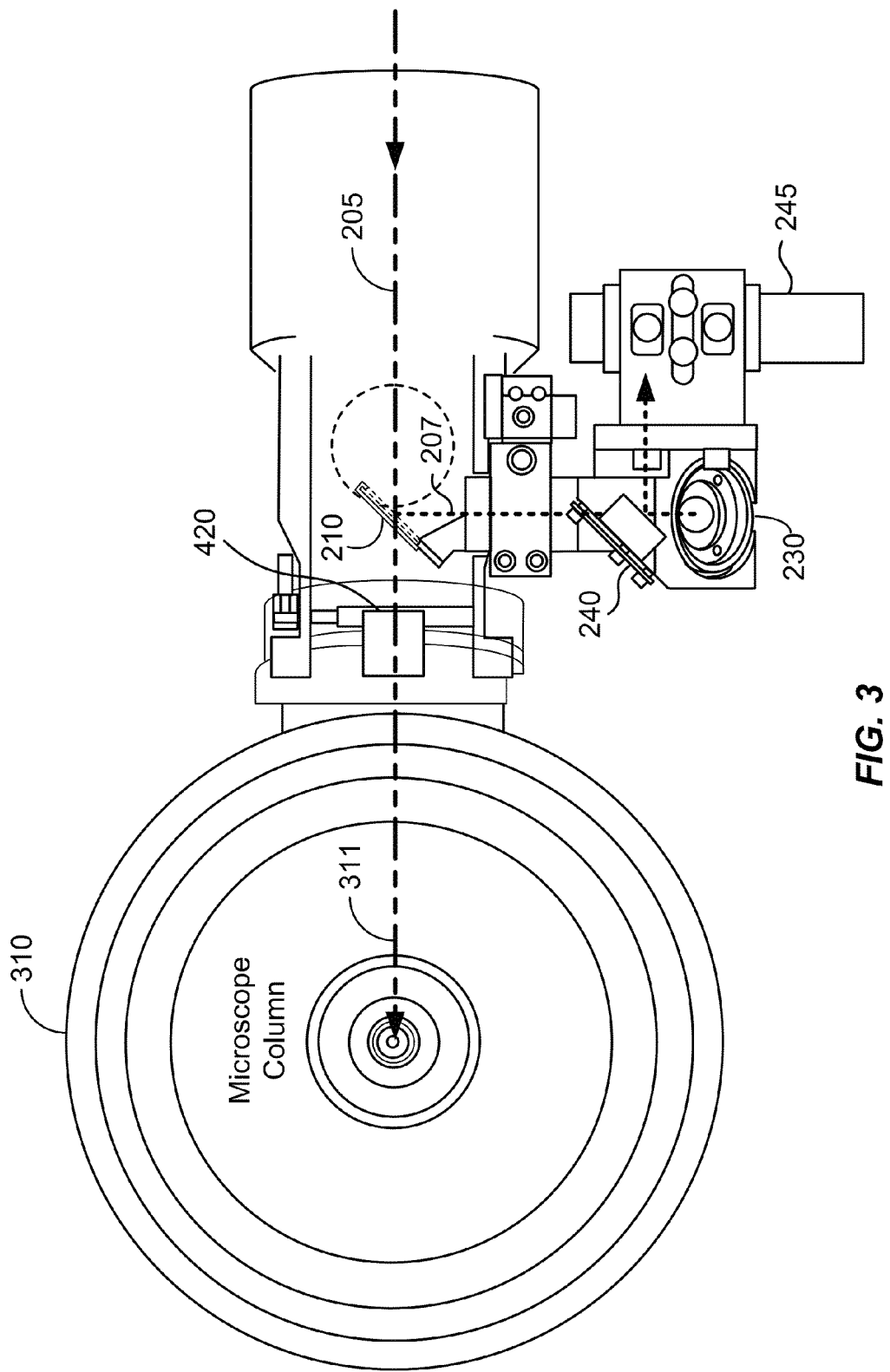
FIG. 3 is a simplified schematic diagram illustrating a tilted plan view of elements of the tracking and control system according to an embodiment of the present invention.

FIG. 3 is a simplified schematic diagram illustrating a tilted plan view of elements of the tracking and control system according to an embodiment of the present invention. This view illustrates a top view at a predetermined tilt angle (e.g., 10° tilt). The microscope column 310 is extending into the plane of the figure. This view can be considered as looking straight down, with the microscope column in a vertical orientation with respect to the plane of the figure.

Figure 4:
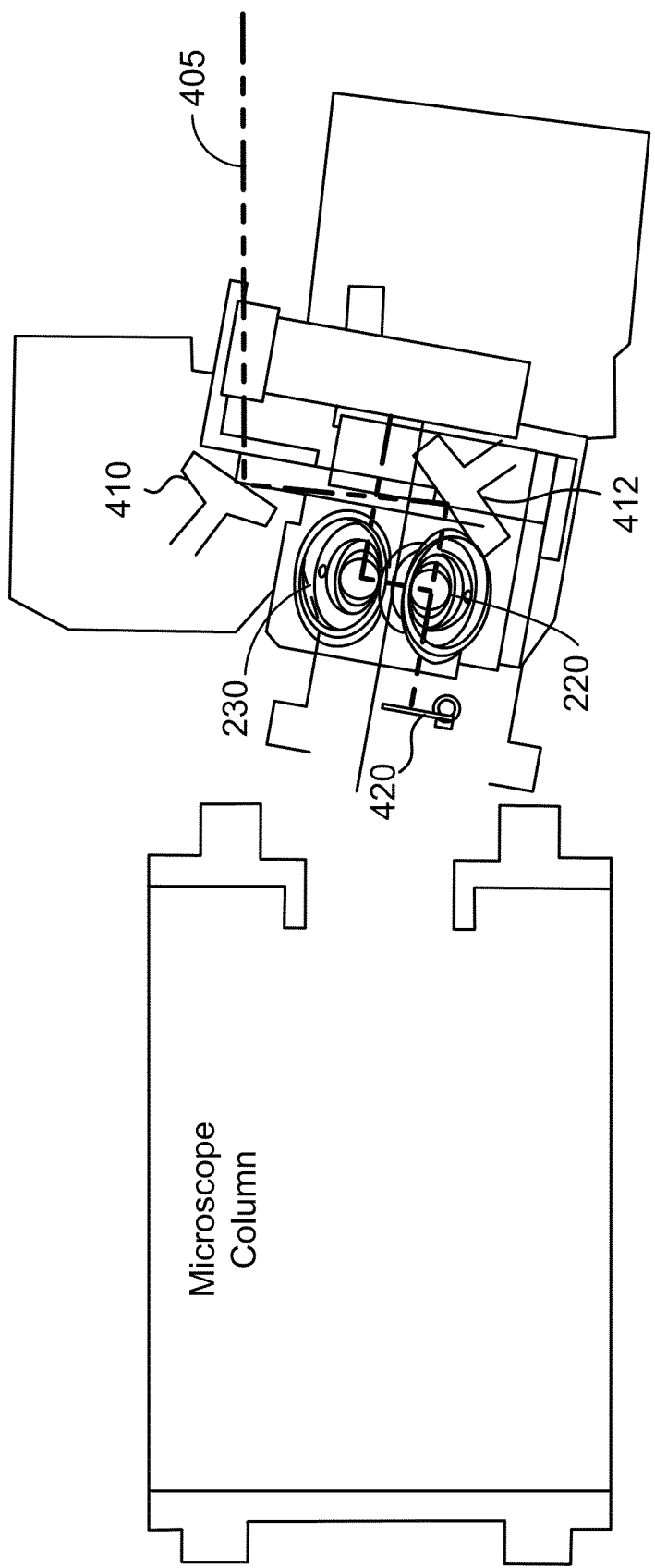
FIG. 4 is a simplified schematic diagram illustrating a side view of elements of the tracking and control system according to an embodiment of the present invention.

The laser beam that is directed to the specimen is illustrated as laser beam 205, propagating to the left into the microscope column and then towards the specimen. In this diagram, and as can be understood by comparison with FIG. 4, the laser beam 205 is not lying in the plane of the image, but is tilted at a predetermined angle (e.g., 10° tilt) with respect to the plane of the figure. Accordingly, in this schematic, distance between the laser beam 205 and the plane of the figure decreases as the laser beam initially propagates to the left towards the microscope column. Referring to FIG. 4 for comparison, and as described more fully below, the laser beam 405 is horizontal before reaching the periscope and then is tilted up as it propagates towards the shutter. One of ordinary skill in the art would recognize many variations, modifications, and alternatives.

As the laser beam 205 enters from the right, beam splitter 210 is used to reflect a portion of the incident beam toward the elements of the tracking and control system. The main portion of the laser beam continues into the microscope column along optical path 311. A shutter 420 (illustrated in the open position) is positioned after the beam splitter, enabling blocking of the beam propagating along optical path 311. Although not shown in FIG. 3, after entering the microscope column, the light along optical path 311 will be directed using mirror(s) and/or lens(es) to impinge on the specimen.

As described more fully herein, the polarization of laser beam 205 is variable, enabling characterization of samples using a variety of polarizations. These polarizations can include various components of linearly polarized light (S and P) as well as circular, elliptical, and other polarizations.

After reflection from beam splitter 210, a few percent of the incident laser light is reflected along optical path 207, which is a portion of an optical path that can be referred to as the detection path, the reference path, or the like. As discussed in relation to FIG. 2A, the light in the detection path, after reflection from the beam splitter, is incident on mirror 2, which is not shown in FIG. 3 because it is disposed behind mirror 3 (230) behind the plane of the figure. Thus, light along path 207 is actually disposed behind the plane of the figure, is reflected along a direction parallel to the surface normal to the figure, and is incident on mirror 3 (230). After reflection off of mirror 3, the light propagates in the plane of the figure and is reflected off mirror 4 (240) towards detector 250, which is mounted in detector housing 245. As an example, the detector can be a CCD detector with high sensitivity over a wavelength range including the wavelength of the laser. Referring back to FIG. 2A, mirror 2 and mirror 3 are oriented at right angles to each other, suitable for directing light parallel to the plane of the figure to propagate in a direction perpendicular to the figure after reflection. Both mirrors are oriented at 45° to the incident beam.

As illustrated in FIG. 3, the apparatus is fixed to the microscope column 310 in order to provide for a fixed spatial relationship between the elements of the apparatus and the microscope column. The apparatus is attached to a window mounted in the side of the microscope column in some embodiments.

FIG. 4 is a simplified schematic diagram illustrating a side view of elements of the tracking and control system according to an embodiment of the present invention. In FIG. 4, a periscope including mirrors 410 and 412 is used to direct light from laser beam 405 onto beam splitter (not shown) that is positioned behind mirror 2 (220). Light passing through the beam splitter can be blocked from entering the microscope column using shutter 420, which is illustrated in the closed position, blocking the beam at the shutter. Light reflected from the beam splitter is then reflected off of mirror 2 (220), as well as mirror 3 (230) and mirror 4 (not shown) before impinging on the detector. The use of the shutter 420 enables experiments in which delicate specimens are utilized. Closing the shutter prevents the laser light from impinging on the specimen while the laser is positioned exactly in a certain position on the detector. The fluence (i.e., energy per unit area) or intensity (i.e., power per unit area) can be monitored and adjusted at the detector, as well as the position of the laser beam on the detector, prior to the shutter being opened so that once the shutter is opened, the impingement of the beam on the delicate sample can be controlled spatially as well as with respect to fluence/intensity. These adjustments can be made without exposure of the sample, enabling placement and control of the laser beam in a pre-exposure manner.

A front-surface and a back-surface reflection from the thin uncoated beam-splitter are both monitored on the detector providing additional information on the beam focus and power and on the beam-splitter reflectivity. The thickness of the other three elements in the replica path is chosen to be large enough 3/8 inch) to ensure that only the front surface reflection may reach the detector. The majority of the beam incident on each of those elements is cleanly transmitted and exits the apparatus to reduce scattered light and serve as alignment guides for installation. The relative mounting of the four reflective elements is fixed, and the entire body is attached to the microscope with the beam-splitter inserted into the path of the focused excitation beam just before the beam enters the TEM column, 190 mm from the specimen plane. The entire replica beam path is thus also required to be 190 mm, divided among four mutually orthogonal arms. The body mounting allows four degrees of freedom for positioning of the beam-splitter, allowing the incident beam to pass through the center of the beam-splitter at an incidence angle of 45° for any possible initial laser alignment into the microscope. The detector is mounted to the body also with three degrees of freedom to allow selection of the area of the 5 mm×7 mm detector surface to be used in the event of damage to the CCD and to accommodate deviations from the nominal 190 mm beam path length. Incorporated in the design is a mechanical shutter beyond the beam-splitter on the path to the specimen to allow the specimen to be shielded from the excitation beam while using the detector image to monitor and/or tune the desired properties of the beam. Mounting holes are available for additional bracing for vibration damping, if needed, or for addition of auxiliary devices or for using the apparatus as a stand-alone device for monitoring laser beams independent of the microscope.

In some embodiments, the energy and time correlation, i.e., the chirp, of imaging electron pulses in dispersive propagation is measured by time-slicing (temporal hole burning) using photon-induced near-field electron microscopy. The chirp coefficient and the degree of correlation can be obtained as well as the duration of the electron pulse and its energy spread.

Figure 27:
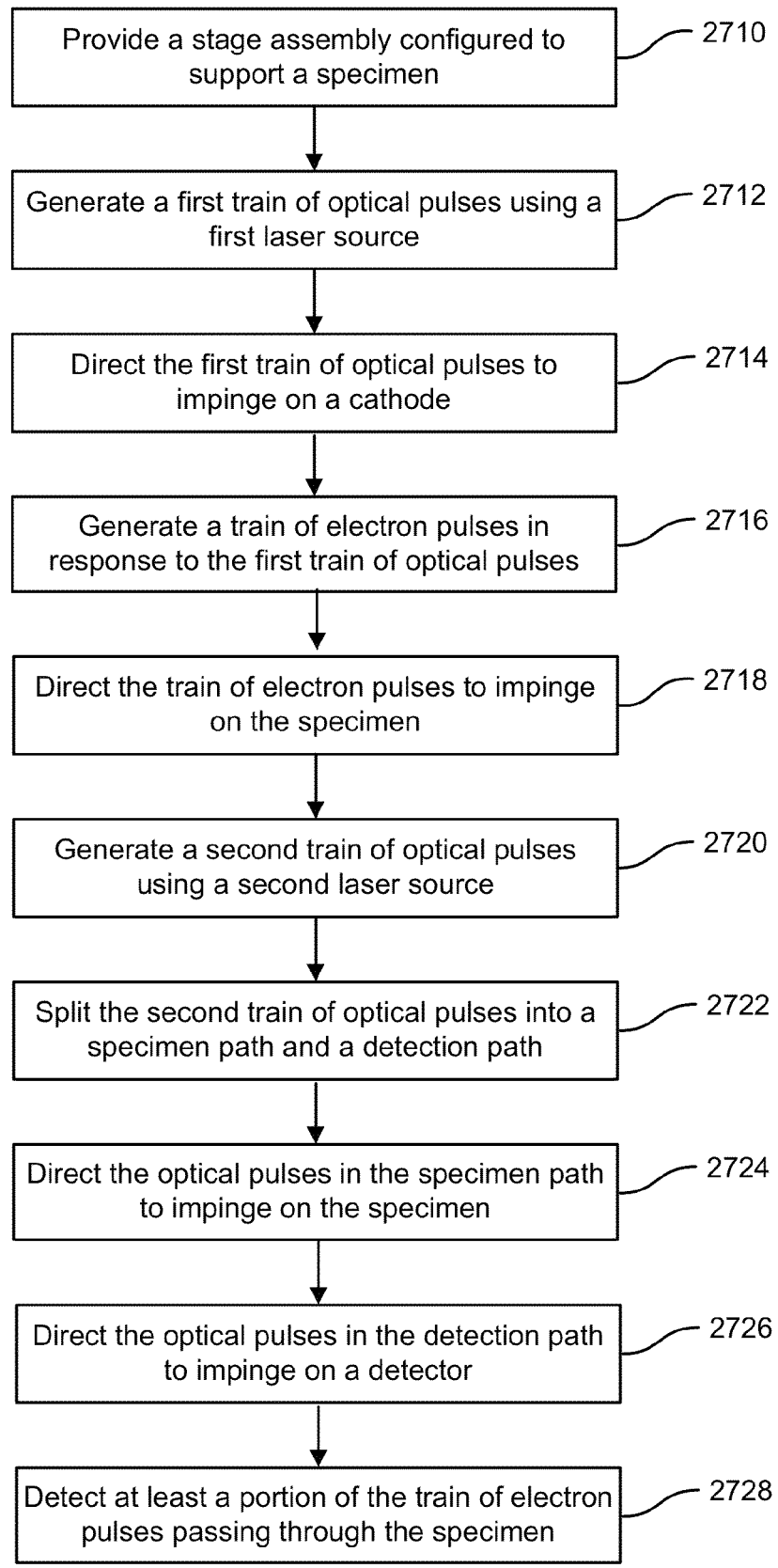
FIG. 27 is a simplified flowchart illustrating a method of imaging a sample according to an embodiment of the present invention.
Figure 28:
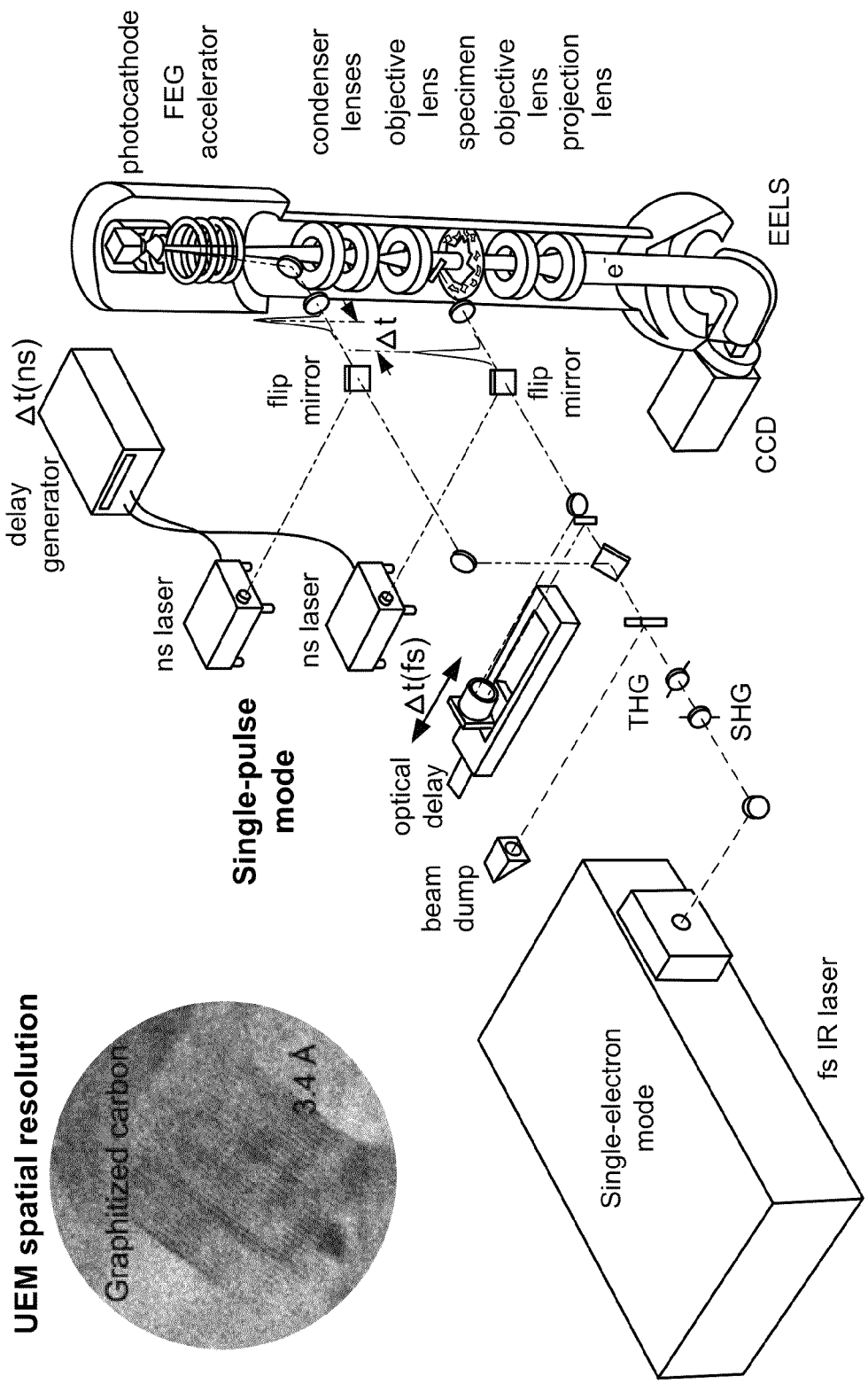
FIG. 28 is a simplified schematic diagram illustrating an advanced ultrafast electron microscope according to an embodiment of the present invention.

FIG. 27 is a simplified flowchart illustrating a method of imaging a sample according to an embodiment of the present invention. The method includes providing a stage assembly configured to support the specimen (2710), generating a first train of optical pulses from a first laser source (2712), directing the first train of optical pulses along an optical path to impinge on a cathode (2714), generating a train of electron pulses in response to the first train of optical pulses impinging on the cathode (2716), and directing the train of electron pulses along an imaging path to impinge on the specimen (2718). The method also includes generating a second train of optical pulses from a second laser source (2720) and splitting the second train of optical pulses into a specimen path and a detection path (2722). The first laser source and the second laser source can be a same laser source. The specimen path and the detection path have equal optical path lengths. The detector in the detection path can be operable to measure a polarization of the optical pulses in the detection path, which can include polarization compensating optical elements.

The method further includes directing the optical pulses in the specimen path to impinge on the specimen (2724), directing the optical pulses in the detection path to impinge on a detector (2726), and detecting at least a portion of the train of electron pulses passing through the specimen (2728). The fluence of the optical pulses in the detection path is typically less than a fluence of the optical pulses in the specimen path.

In an embodiment, the method also includes blocking the optical pulses in the specimen path while concurrently directing the optical pulses in the detection path to impinge on the detector. In these embodiments, the laser parameters can be adjusted without exposure of the specimen and then the specimen path can be unblocked (e.g., by opening a shutter) once the desired parameters are achieved.

It should be appreciated that the specific steps illustrated in FIG. 27 provide a particular method of imaging a specimen according to an embodiment of the present invention. Other sequences of steps may also be performed according to alternative embodiments. For example, alternative embodiments of the present invention may perform the steps outlined above in a different order. Moreover, the individual steps illustrated in FIG. 27 may include multiple sub-steps that may be performed in various sequences as appropriate to the individual step. Furthermore, additional steps may be added or removed depending on the particular applications. One of ordinary skill in the art would recognize many variations, modifications, and alternatives.

The advent of four-dimensional (4D) electron microscopy has made possible the direct study of structural dynamics with atomic-scale spatiotemporal resolutions. The scope of applications is diverse, from the studies of chemical bonding dynamics to macromolecular conformation changes and to nanomechanical vibrations. In these implementations, ultrashort electron pulses are utilized in imaging, diffraction, and spectroscopy, and it is helpful to optimize the spatial and temporal coherence in order to achieve atomic-scale resolutions. In general, the electron pulse may have time-energy phase space correlations which, if realized, could be exploited in the control of the time resolution and energy selectivity in imaging, as shown here.

In conventional microscopes, electrons are generated either by heating a source or by field emission; the beam is a continuous wave made of randomly distributed electrons. With a continuous beam, the structures probed are time-averaged over milliseconds or longer acquisition times and the electrons used are temporally incoherent in these recordings. For the electron pulse, three coherence lengths, which are determined by the longitudinal and transverse momentum spread ($\delta p_i$), are simply given by the following relationship:

$$l_{c,i} = \frac{1}{\delta k_i} = \frac{\hbar}{\delta p_i} \approx \frac{\lambda}{2\pi(\delta p_i/p_z)} \text{ for } i = x, y, z; \quad (1)$$

where the total coherence length is given by:

$$\frac{1}{l_c^2} = \frac{1}{l_{c,z}^2} + \frac{1}{l_{c,x}^2} + \frac{1}{l_{c,y}^2}.$$

It follows that a typical ~1 eV energy spread at a kinetic energy of 200 keV gives rise to a small longitudinal momentum spread ($\delta p_z$), and the electron coherence becomes dominantly determined by the transverse value. However, this transverse coherence for a heated source is relatively poor, and for high resolution, lenses and apertures are introduced in order to reduce the transverse momentum spread and achieve the desired coherence at the specimen. This leads to a loss in the number of electrons, typically with a throughput of $10^{-1}$ to $10^{-4}$ from the source to the specimen.

In 4D electron microscopy, coherence is determined by properties of the electron pulse that is generated by the femtosecond (fs) optical pulse via the photoelectric (or field assisted photoelectric) effect. Unlike the randomly distributed electrons in conventional microscopes, the pulses are timed with fs accuracy. Unless each pulse contains a single electron, the space-charge effect will lead to an energy (and time) spread. In this space-charge regime, transverse coherence may still be manipulated using apertures and condenser lenses, because transverse Coulomb repulsion is negligible at the center of the beam (when considering the integration of interactions over the beam cross section) and its magnitude increases as the distance from the center increases. Thus, only a small portion at the center of the beam can be selected for imaging/diffraction with relatively high coherence.

On the other hand, longitudinal Coulomb repulsion induces a momentum spread which cannot be reduced by lenses, and may become the dominant factor in determining the coherence time and length; for energy spreads larger than ~10 eV in a typical microscope, the longitudinal coherence becomes poorer than the transverse counterpart. To maintain the high spatial resolution in the pulsed mode, the number of electrons per pulse is reduced in what is termed as the single-electron regime. In practice, an electron pulse with up to ~$10^2$ electrons at the source does not suffer significantly from the space-charge effect (temporal spread) whereas the energy spread begins to increase at ~$10^1$ electrons per pulse. The Coulomb repulsion energy, together with the excess energy above the work function, constitutes the total electron-energy spread; for thermionic, Schottky field emission, and cold field emission sources the spreads are typically 1.0, 0.6, and 0.3 eV, respectively. A monochromator can reduce the energy spread down to 0.15 eV, and for pulsed photoelectrons, an energy spread of 0.1 eV has been successfully achieved.

The energy spread in the pulse can develop a chirp, an energy-time correlation, because the electrons with higher energies lead and the ones with lower energies lag, depending on the electron distribution at the source (see below); an energy spread of 1 eV can result in a temporal spread of several hundred fs. The uncertainty in position-momentum is related to such broadening depending on electron speed (v): $\Delta x \Delta p = (\Delta x/v) \cdot (v \Delta p) = \Delta t \Delta E$.

To circumvent pulse broadening, and to compress ultrashort electron pulses, several techniques have been developed, and these include: the lowering of the excess energy above the work function; energy filtering at the detector which limits the energy distribution; and the use of a "reflectron" (an electrostatic mirror) that can reverse the chirp and compress the pulses. Alternatively, radiofrequency (RF) electric fields, a time-dependent acceleration/deceleration, can boost up lagging electrons at the tail of the pulse and retard the leading electrons at the front, leading to a compression of the initial pulse. Using the ponderomotive force of optical pulses, it is possible to design a "temporal lens" (position-dependent acceleration/deceleration) that can push the trailing electrons and pull the leading electrons, and cause an inverse chirp. The aforementioned methods can also be used to reverse space-charge temporal broadenings in multi-electron pulses, and it is even possible to shorten their durations beyond the initial width. It follows that understanding energy-time correlations in electron propagation is essential for maintaining and improving the spatial, temporal, and energy resolutions in imaging.

Herein, direct experimental mapping of phase space (energy-time correlations) is discussed using photon-induced near-field electron microscopy (PINEM) with fs time resolution. Here it is shown that a "hole" can be burned in the energy distribution of the electron pulse. By invoking a nanostructure (silver wire), the optical pulse creates a near field which enables the coupling between the evanescent photons and electrons. It was possible to establish the chirp relationship between time and energy by following the time-dependent shift of the zero-loss peak (ZLP) and PINEM peaks in the energy spectrum. Temporally shorter and energetically narrower coherent electron pulses, from linearly chirped electron pulses, are obtained by exploiting features of the chirp in the electron microscope. The theoretical analysis supports the experimental findings, and here we only highlight the relevant theoretical concepts of PINEM and of pulse slicing. Additional description related to microscope systems suitable for utilization with embodiments of the present invention is provided in U.S. Patent Application Publication No. 2011/0220792, published on Sep. 15, 2011, the disclosure of which is hereby incorporated by reference in its entirety for all purposes.

The experiments were performed on a collection of silver nanowires with a diameter ranging from 50 to 100 nm. The time-resolved electron energy spectra were recorded using Caltech's second generation ultrafast electron microscope (UEM-2). The electron source is equipped with a field-emission gun geometry (Tecnai 20, FEI). The tip is replaced by a 16 μm LaB$_6$ flat cathode, whose work function is ~2.6 eV. A train of 280 fs infrared laser pulses (λ=1038 nm) at a repetition rate of 2 MHz was split into two parts, one of which was frequency doubled to give the 519 nm laser pulses which were used to excite the nanostructures at a fluence of 0.5 mJ/cm$^2$. The other beam was frequency quadrupled to produce UV pulses (259 nm, 4.78 eV) which were directed to the photocathode to generate the electron pulses.

The energy spread of the electron pulse can be manipulated by changing the number of electrons and the excess energy above the work function; here we varied the spread from 1.2 eV to 3.5 eV using the former not the latter. The electron pulses were accelerated to 200 keV in the column and dispersed after transmission through the specimen in order to provide the energy spectra of the electrons which interacted with the photons; a 1 mm entrance aperture was used to retain the optimal energy resolution. The timing between the optical pump/gate pulse and the electron probe pulse at the specimen was controlled by an optical delay line.

PINEM of the Chirped Pulses

In general, electron energy distributions are incoherent due to the emission process in the microscope. This gives rise to velocity distributions that lead to different arrival times at the specimen for electrons with different energy. Accordingly, in the pulsed mode, each single-energy packet will experience different temporal overlap with the optical pulse used to excite the nanostructure. Previously, the theory for this electron-photon interaction (PINEM description) has been reported for a coherent single-energy packet. Herein, we formulate the theory for chirped pulses which have energy distributions. The solution is obtained by solving the time-dependent Schrödinger equation of the electron wavefunction in the space domain and as a function of time. It is, however, more convenient to represent it as the temporal solution as a probability density in the time domain in order to describe the electron dispersion and the temporal coincidence with the optical pulse.

We designate G(x) to be a normalized Gaussian profile along the coordinate, x, with $\bar{x}$ and $\sigma_x$ being the mean value and standard deviation width, respectively:

$$G(x) = G(x; \bar{x}, \sigma_x) = G(x - \bar{x}; \sigma_x) = \frac{1}{\sqrt{2\pi}\,\sigma_x} \exp\left[-\frac{(x-\bar{x})^2}{2\sigma_x^2}\right] \quad (2)$$

The probability density of a propagating electron packet at a single energy (ignoring coherent dispersion) becomes:

$$P_e(z,t) = G(z - v_e t; v_e \sigma t_e), \quad (3)$$

where $v_e$ and $\sigma t_e$ are the velocity and the temporal width, respectively. Equation (3) describes the spatial density at a given time, t, or the temporal profile at a given position, z, such that they can be related by $$P_{e,t=T}(z)|dz| = P_{e,z=Z}(t)|dt|$$

$z - v_e T = Z - v_e t$; it follows that $$t - T = -(z - Z)/v_e,$$

where T is the time at which the spatial distribution is probed and Z is the position where the temporal profile is considered. Similarly, we assume that the optical intensity at z=Z is given by $$I_p(T) \propto I_0 G(t - \bar{t}_p; \sigma t_p).$$

Accordingly, at $$z = Z, \bar{t}_e = \langle t \rangle_e = \int dt\, t P_e(t)$$

and $$\bar{t}_p = \langle t \rangle_p = \int dt\, t P_p(t)$$

become the mean arrival times of an electron packet (moving at $v_e$) and an optical pulse (moving at c), respectively; $\tau \equiv \bar{t}_e - \bar{t}_p$ is then the delay time between the electron and optical pulses. For convenience, we define $z' \equiv z - v_e t$ as the moving frame coordinate system. Similarly, we define $$t' \equiv -z'/v_e$$

which corresponds to an "instantaneous" time that describes the temporal profile of the packet with $$P_e(z')|dz'| = P_e(t')|dt'|.$$

The quantum mechanical derivation is given below, and the definition of terms is listed in Table 1. Here, we present a simple classical picture with a physical interpretation. For a single-energy packet, the PINEM intensity profile can be expressed as, $$P_n(t';\tau) = P_e(t') \cdot Q_n(t';\tau), \quad (4)$$

where $P_e(t')$ is the electron probability density in the time domain (temporal profile or intensity flux) and $$Q_n(t'; \tau) = |J_n(\Omega(t'; \tau))|^2$$

is the n th order transition probability of PINEM. $J_n$ is the Bessel function of the first kind with the argument given by $$\Omega(t';\tau) = -\frac{e|\tilde{F}|}{\hbar\omega_p}\exp\left[-\frac{(t'+\tau)^2}{4\sigma t_p^2}\right].$$

This separation of $P_e$ and $Q_n$ has significant consequences. Since $Q_n$ is independent of the electron profile, $P_e$, it can be regarded as the efficiency of a temporal filter, or a pulse slicer; a time domain analogue to an electron energy filter. Here, we only consider the weak interaction limit to derive analytical expressions for the chirp coefficient, pulse slicing, and energy refinement. The strong interaction case was treated elsewhere using numerical integration. In the weak interaction regime, $Q_n$ can be approximated and becomes linearly proportional to $$|I_p(t')|^n,$$

for n>0. It follows that the PINEM intensity profile becomes:

$$P_n(t';\tau) \propto P_e(t') \cdot |I_p(t';\tau)|^n. \quad (5)$$

Figure 5A:
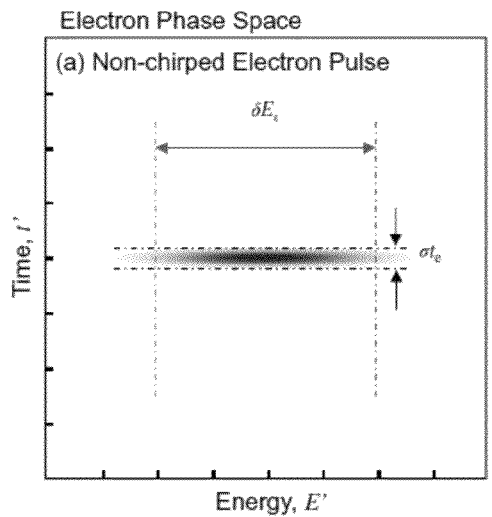
FIGS. 5A-F illustrate characteristics of electron pulses and PINEM spectra according to an embodiment of the present invention.
Figure 5D:
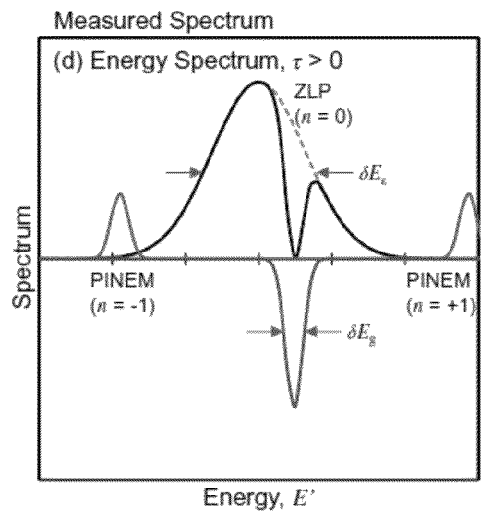
Figure 5B:
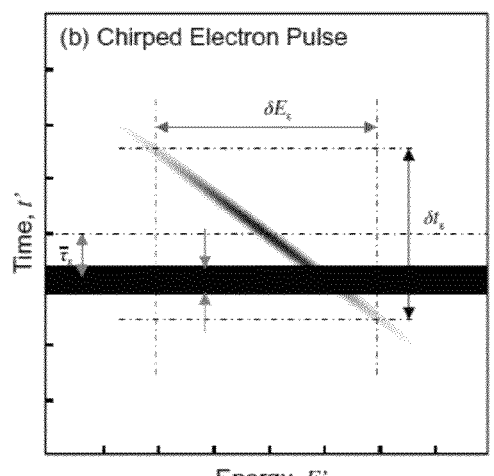
Figure 5E:
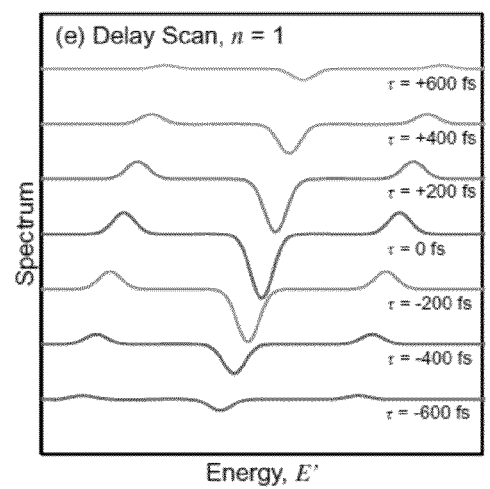
Figure 5C:
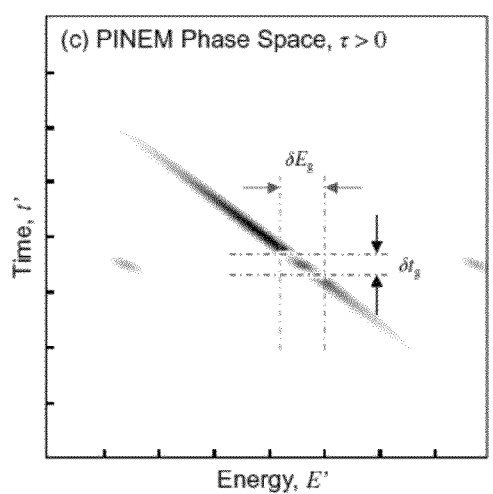

Given the results for a coherent single-energy packet, we can then consider the incoherent energy distribution associated with a chirp. The electron ensemble ($\in$) has a mean energy value of $\overline{E}_\in$. Therefore, we redefine $z' \equiv z - \overline{V}_\in t$ and $t' \equiv -z'/\overline{V}_\in$ with respect to the electron ensemble. The PINEM intensity of the individual energy component becomes:

$$P_{E,n}(t';\overline{\tau}) \approx P_E(t';\Delta\overline{t}_E) \cdot Q_n(t';\overline{\tau}_E), \quad (6)$$

where $\Delta\overline{t}_E \equiv \overline{t}_E - \overline{t}_\in$ accounts for the energy-dependent arrival time difference for the electron packet of energy E within the pulse (FIGS. 5A and 5B). Equation (6) has the same form as equation (4), except the distribution of $P_E(t';\Delta\overline{t}_E)$ includes the temporal shift as a parameter, because t' is defined with respect to the ensemble average and the single-energy packet at E is displaced from (not coincident with) it. We note that $Q_n$ only depends on the pump (in this case the hole burning or gating pulse) laser profile and $P_E(t';\Delta\overline{t}_E)$ depends on the energy distribution of the electron pulse. Consequently, the electrons will exhibit an energy-dependent temporal overlap with the gate optical pulse (FIG. 5B), with an energy selection that depends on the characteristics of the chirp (FIGS. 5C and 5D).

FIG. 5 illustrates population density plots of energy-time phase space before (FIG. 5A) and after (FIG. 5B) developing chirp. Energy spread ($\delta E_\in$), temporal width ($\sigma t_e$) and temporal duration ($\delta t_\in$) are indicated with dotted lines. Optical duration ($\sigma t_p$) and electron-photon time delay ($\overline{\tau}_\in$) are also indicated in green for chirped electrons. FIG. 5C illustrates population density plot in energy-time phase space and FIG. 5D illustrates a line plot in the energy domain (integrated along the time domain) of the temporally gated electron. ZLP depletion and PINEM peak gain are shown. FIG. 5E illustrates electron energy spectra (EES) at different time delays. FIG. 5F illustrates a line plot of the fractions of electrons in the n th state as a function of time delay.

Figure 5F:
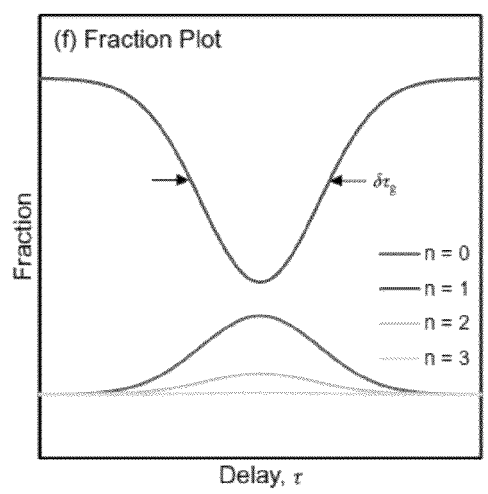
Figure 6A:
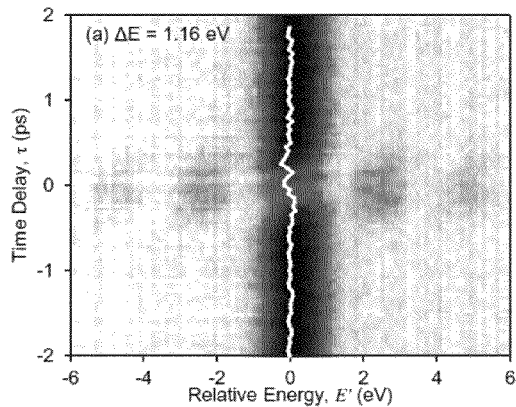
FIGS. 6A-F illustrate measured characteristics of electron pulses and PINEM spectra according to an embodiment of the present invention.
Figure 6D:
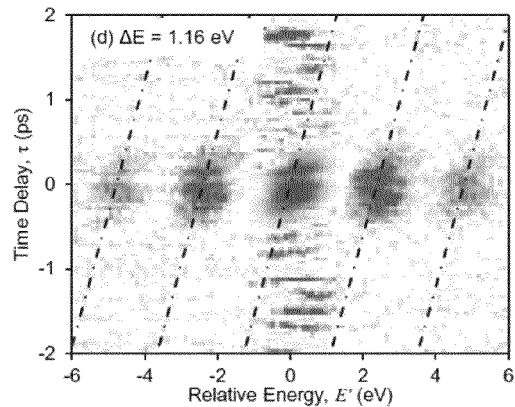
Figure 6B:
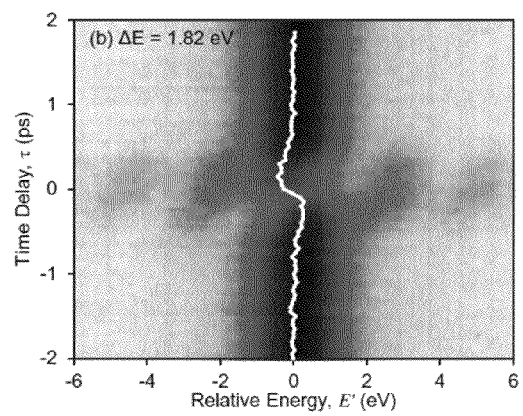
Figure 6E:
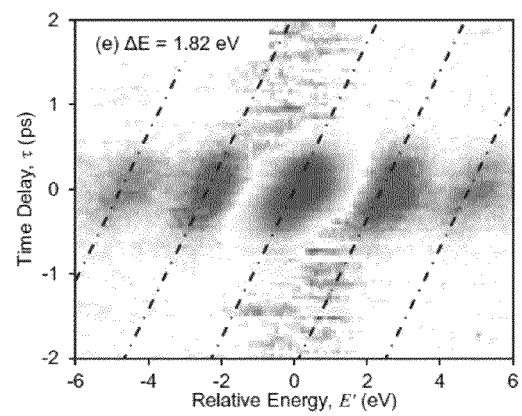
Figure 6C:
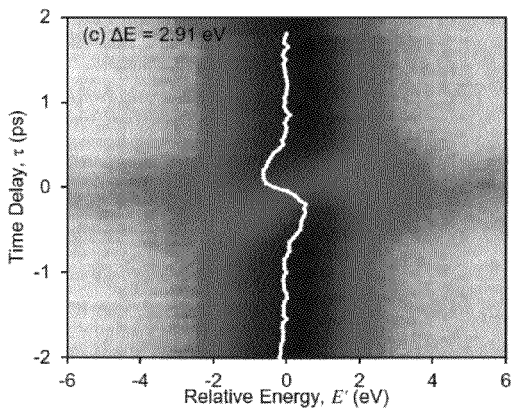
Figure 6F:
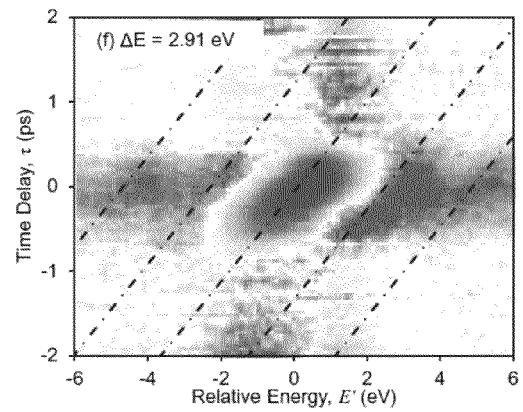

Assuming Gaussian profiles for the initial time and energy distributions, we can formulate the phase-space evolution of the chirped electron ensemble, which provides the temporal duration and energy spread following PINEM gating or conventional energy filtering. For time-slicing, we can express the experimental observable, i.e. the energy distribution of PINEM electrons at the given electron-photon nominal temporal delay, $\overline{\tau}_\in$, as $$P_g(E';\overline{\tau}_\varepsilon) \propto G[\overline{\tau}_\varepsilon;\delta\tau_g] \cdot G[E' - \Delta\overline{E}_g(\overline{\tau}_\varepsilon);\delta E_g], \quad (7)$$

where the product is that of two Gaussians for the temporal overlap efficiency and the energy profile of the entire distribution of the pulse, with $\delta\tau_g$ being the duration of the observed PINEM profile, such that $G[\overline{\tau}_\in;\delta\tau_g]$ results from the convolution of electron and photon temporal profiles (FIG. 5F). We note that $E' \equiv E - \overline{E}_\in$ is the relative energy (coordinate), $\Delta\overline{E}_g(\overline{\tau}_\in)$ is the delay-dependent mean energy shift of gated electrons (FIG. 5E), and $\delta E_g$ is the time-sliced electron energy spread (FIG. 5D). The apparent slope (mean energy shift per time delay, $d\overline{E}_g/d\overline{\tau}_\in$) is related to the intrinsic chirp coefficient (arrival time shift per energy, $\partial\overline{t}_E/\partial E$) (FIG. 5B), and the temporal duration and energy spread of the chirped electrons; the optical pulse length also affects the apparent slope.

FIG. 6 illustrates experimental population density plots of (left) absolute and (right) difference spectra of electron energy as a function of time delay for the electron energy spreads of (top) 1.16 eV, (middle) 1.82 eV, and (bottom) 2.91 eV. The mean energy of ZLP is indicated as white solid lines on the left column. The apparent slopes of energy shift as a function of time delay are indicated as a dotted line for ZLP depletion and PINEM growth on the right column.

FIG. 6 shows the density plots of the experimentally measured $P_g(E;\overline{\tau}_\in)$, the time-sliced energy-distributions of chirped electron ensembles at the given time delay ($\overline{\tau}_\in$) between the electron and photon pulses for three different energy spreads of the ZLP ($\delta E_\in$); the energy spread was varied using the laser fluence at the photocathode. The density plots of absolute values are given in the left column, whereas those of the differences with respect to a reference frame at negative time delay are shown in the right column. Only when electron and photon pulses are temporally overlapped ($\overline{\tau}_\in \approx 0$), was the ZLP depleted (FIG. 6, right column) and new PINEM peaks populated (red in FIG. 6, right column) at the energy of $\overline{E}_n = \overline{E}_\in + n\overline{E}_p$. FIG. 6 clearly displays manifestations of electron chirp; the ZLP depletes whereas the PINEM grows, and their energy values increase as a function of time delay. The apparent slope of the energy shift increases as the energy spread increases. It also can be seen that the energy spread of PINEM peaks is smaller than the initial electron energy spread (see Table 2).

The density plot of difference data was fitted by a least square method using equation (7) in order to obtain the time-sliced energy spread ($\delta E_g$), PINEM temporal resolution ($\delta\tau_g$), and the apparent slope ($d\overline{E}_g/d\overline{\tau}_\in$). The initial energy spread ($\delta E_\in$) was determined from the energy profile of ZLP at negative time delays. The fitted slopes are also plotted in FIG. 6, right column. The higher-order PINEM peaks should exhibit a nonlinear dependence on photon pulse length ($\sigma t_p$). However, here, for simplicity, we fitted the data with the same $\delta\tau_g$ for every PINEM peak, since the deviation becomes smaller when the apparent electron duration, $\delta t_\in$, is longer than the photon pulse length. From the data we determined the intrinsic temporal width of the electron pulse ($\delta t_\in$) and the intrinsic chirp coefficient ($\partial\overline{t}_E/\partial E$) as a function of $\delta E_\in$, using the optical pulse width value corresponding to 280 fs in full width at half maximum (FWHM). The fitted parameters are listed in table 2, and the calculated parameters are compared to the observed ones in FIG. S1 of supporting information.

The intrinsic chirp coefficient, $\partial \bar{t}_E/\partial E$, (slightly) decreases as a function of the energy spread (Table 2). The (differential) temporal width, $\sigma t_e$, is substantially longer than the nominal optical duration, and (slightly) increases as a function of energy spread. Consequently, the calculated $\delta t_\in$ (electron duration) and $\delta \tau_g$ are largely determined by $\sigma t_e$, rather than by the energy spread term, and the apparent slope, because $$\frac{d\bar{E}_g}{d\bar{\tau}_\varepsilon} = \frac{\delta E_\varepsilon^2}{\delta \tau_g^2}\left(-\frac{\partial \bar{t}_E}{\partial E}\right),$$

increases as $\delta E_\in$ increases. On the contrary, if the electron pulses were highly correlated $$\left(\sigma t_e^2 \ll \left(\frac{\partial \bar{t}_E}{\partial E}\right)^2 \delta E_\varepsilon^2\right)$$

and, therefore, $$\delta \tau_g \approx \delta t_\varepsilon \approx \left(-\frac{\partial \bar{t}_E}{\partial E}\right)\delta E_\varepsilon,$$

one would observe $$\frac{d\bar{E}_g}{d\bar{\tau}_\varepsilon} \approx \left(-\frac{\partial \bar{t}_E}{\partial E}\right)^{-1}.$$

At low laser fluences, the temporal width and the intrinsic slope seem to deviate from those in the space-charge regime. This may be because the two sources of energy spread (excess energy above work function and the space-charge effect) lead to different behavior in the propagation dynamics.

With the electron pulse fully characterized using the temporal gating method, we can now investigate the coherence of imaging electrons. The origin of the coherence degradation is of particular interest, being either the photon excess energy or the space-charge effect. The analytical expression of the temporal spread due to an energy spread can be derived from the equation of motion. For the space-charge effect, a classical trajectory Monte Carlo simulation can be employed to examine the temporal broadening. However, it is understood that Coulomb repulsion is strongest in the early stages of acceleration and/or propagation where the electron pulse is small in size, but vanishes as the electron pulse disperses. Therefore, we may approximate that the space-charge effect induces an instantaneous energy spread by which the electron pulse spreads.

It follows that within the impulse model, we can theoretically estimate the intrinsic chirp coefficients. For a simple field-free drift, it becomes $$\frac{\partial t_l}{\partial E} = -\frac{l}{\gamma^3 m_e \bar{v}^3} = -\frac{l}{\bar{\gamma}(1+\bar{\gamma})}\frac{\bar{t}_l}{\bar{E}}, \qquad (8)$$

where l is the distance, and $m_e$, v, and $\gamma$ are the electron mass, the velocity, and the associated relativistic factor, respectively, such that $$\bar{t}_l = l/\bar{v}, \ \bar{p} = \bar{\gamma} m_e \bar{v}, \ \bar{E} = \frac{\bar{p}^2}{(1+\bar{\gamma})m_e}, \ \frac{\partial E}{\partial p} = \bar{v},$$

and $$\frac{\partial p}{\partial v} = \bar{\gamma}^3 m_e.$$

Here, E refers to the kinetic energy, not the relativistic energy. For a linear acceleration, we obtain $$\frac{\partial t_d}{\partial E} = \frac{d}{q_e V}\left(\frac{1}{\bar{v}_f} - \frac{1}{\bar{v}_i}\right) \approx -\left(\frac{d}{\bar{v}_i}\right)\frac{1}{\bar{E}}, \qquad (9)$$

where d is the distance of acceleration, $q_e$ is the electron charge, and V is the acceleration voltage, such that $\bar{E} \approx q_e V$. Equation (9) is in a form similar to that of the field-free drift, except that $d/\bar{v}_i$ is a fictitious duration as if electrons were to travel with the initial velocity. Assuming l=500 mm for $\bar{E}$=200 keV, we get $\bar{t}_l$=2.4 ns, and $\bar{\gamma}$=1.39, and therefore $$\frac{\partial t_l}{\partial E} = -0.004$$

ps/eV, which is much smaller than what we observed in this study $$\left(\frac{\partial \bar{t}_E}{\partial E} \sim -0.2 \text{ ps/eV};\right.$$

see table 2.). Using V=1000 V and d=0.5 mm for the first acceleration stage in UEM-2, and $\bar{v}_i$=5×10$^{-4}$ mm/ps from $\langle E_i \rangle$=0.7 eV at $E_p$−W=2.1 eV, we can estimate $$\frac{\partial t_d}{\partial E} = -1 \text{ ps/eV},$$

which is an overestimation when compared with what is observed. Dispersive propagation with a given energy spread increases the intrinsic chirp coefficient as the electron pulse propagates, whereas (instantaneous) Coulomb repulsion decreases the chirp slope as it broadens the energy with the given temporal spread. The fact that the observed intrinsic chirp coefficient is somewhat smaller than the estimated value may suggest that the space-charge effect is not instantaneous, but rather gradual. Another mechanism may be that a chirp develops during the acceleration due to the initial kinetic energy spread; then its slope is reduced by the space-charge effect during the field-free drift, during which electrons can further repel each other, but hardly spread.

Besides the temporal dispersion, electron pulses may suffer from an inhomogeneous temporal broadening. There are three contributions in temporal broadenings in UEM, which are beam path inhomogeneity, initial kinetic energy spread, and the space-charge effect: (a) The electron pulse is generated in a finite size and with a transverse momentum spread. Due to the diffusive lensing effect of the acceleration source in FEG, and the compensating and condensing lenses, electrons at the center of a pulse and those at the perimeter go through different beam paths, thus creating a temporal lag as a function of the radial (transverse) position; (b) The time spent by an electron in acceleration is a nonlinear function of the initial kinetic energy, between 0 to 2 eV, particularly near 0 eV, and the chirp, therefore, exhibits a nonlinear behavior. Namely, the initial kinetic energy spread not only increases $\delta t_E$ (dispersion), but also deteriorates $\sigma t_e$ (nonlinear chirp). Although time-of-flight is practically a linear function of the initial momentum, neither the final momentum nor the energy is a linear function of the initial momentum; (c) In a simplified model of the space-charge effect, where the repulsive force was assumed to be linearly proportional to the relative position, it would conserve longitudinal emittance, and consequently decrease $\sigma t_e$, while it increases $\delta E_\in$. However, a real electron pulse is not a continuous charge density; it consists of discrete charged particles randomly distributed in space. The discrete randomness induces statistical noise in the space-charge effect, which deteriorates the longitudinal emittance.

To further investigate the electron acceleration/propagation dynamics, we conducted electron trajectory simulations (not shown here), which confirm that the path length inhomogeneity is the dominant factor for increasing $\sigma t_e$ as well as $\delta t_\in$, whereas other contributions are relatively small over a few eV of the energy spread range (low current regime). We also found that the space-charge effect increases the energy spread in three steps: after birth (4%), during acceleration (8%), and during drift at crossovers (88%). Temporal dispersion is dominantly determined in the first step, where the velocity is slowest, and the initial chirp coefficient is determined by acceleration dynamics. The final chirp coefficient decreases as a function of charge density, because the space-charge effect increases energy spread during the field-free drift without further dispersion, thus lowering the chirp coefficient. The more energy is spread, the lower the chirp coefficient becomes. Our trajectory simulations indicate that the space-charge effect is fairly linearly proportional to the charge density for energy spread, temporal width, temporal duration, and the intrinsic slope of chirped electrons. Therefore, we attribute the observed deviations at low current limits to uncertainties in measurement and/or analysis.

In table 2, it is shown that the energy spread reduction ($\delta E_g/\delta E_E$) is not too profound, especially for a small initial energy spread. This is due to the fact that the degree of chirp, or degree of correlation between energy and time, is rather poor ($\rho = -0.4$ to $-0.6$ or $R^2 = \rho^2 = 0.1$ to 0.4), namely $\delta t_\in$ is not greater than $\sigma t_e$, as $$\delta E_g = \frac{\sigma \tau_g}{\delta \tau_g} \delta E_\varepsilon = \frac{\sqrt{\sigma t_p^2 + \sigma t_e^2}}{\sqrt{\sigma t_p^2 + \delta t_e^2}} \delta E_\varepsilon.$$

In order to observe a significant energy spread reduction, one needs to satisfy the condition, $$\sigma t_p^2 + \sigma t_\varepsilon^2 \ll \left(\frac{\partial \bar{t}_E}{\partial E} \delta E_\varepsilon\right)^2.$$

Since $\sigma t_e$ is largely deteriorated by beam path inhomogeneity during the acceleration, it is difficult to reduce $\sigma t_e$ to improve the chirp.

$\left(\frac{\partial \bar{t}_E}{\partial E}\right)$ is initially determined by acceleration only, and then reduced by the space-charge effect. Furthermore, the space-charge effect also deteriorates $\sigma t_e$ via the statistical noise. Note that UEM-2 adopted the FEG-TEM design with a modification for photoemission; the conventional microscope is designed without considering temporal dispersion due to its continuous nature. In order to improve the degree of chirp, the electron source will have to be optimized to reduce beam path inhomogeneity and space-charge effect. Transverse momentum spread also needs to be minimized by reducing the photon energy above the photocathode work function, e.g., 460 nm excitation for a 2.6 eV work function instead of a 258 nm excitation. However, the photoemission efficiency (current density) is exponentially reduced as excess energy is reduced. Apertures and lenses may be used to filter out transverse momentum spreads, and this will of course reduce the number of electrons.

FIG. 7 illustrates the populations density plots of phase space of (top) ZLP, (middle) time-selected, and (bottom) energy-selected electrons with (left) highly correlated chirp, (middle) poorly correlated chirp, and (right) pseudo-continuous beam. Integrated energy and time distributions are plotted on the bottom and the left sides of each panel, respectively.

The analytical expressions for temporal and energy distributions of chirped electron pulses after temporal gating or energy filtering allow us to investigate the effect of the degree of chirp on the temporal and energy resolution. FIGS. 7A, 7B, 7D, and 7E compare energy resolutions by temporal gating for cases of good and poor chirps, where $\sigma t_e$ correspond to 0.05 ps and 1 ps in FWHM, for $\sigma t_p$ of 0.05 ps in FWHM, $\delta E_g$ of 2 eV in FWHM and $$\frac{\partial \bar{t}_E}{\partial E} = -0.22$$

ps/eV. When time and energy are well-correlated (FIG. 7A, $\sigma t_e$ corresponding to 0.05 ps in FWHM), the energy spread of PINEM electron becomes 0.32 eV, whereas it becomes 1.83 eV for poor correlation (FIG. 7B, $\sigma t_e$ corresponding to 1 ps in FWHM). It should be noted, however, that the temporal shortening of PINEM electrons is ~0.05 ps for both cases, which is essentially the photon duration, as $$\delta t_g = \frac{\sigma t_p}{\delta \tau_g} \delta t_\varepsilon \approx \sigma t_p.$$

Temporal selection is always possible with PINEM, but energy selection can only be achieved with well-correlated electron beams, as $$\delta E_g = \frac{\sigma \tau_g}{\delta \tau_g} \delta E_\varepsilon \approx \frac{\sigma t_e}{\delta t_\varepsilon} \delta E_\varepsilon,$$

which requires an ultrashort initial electron pulse and little deterioration of the longitudinal emittance.

FIG. 7 also compares time-filtering and energy-filtering for pulsed and pseudo-continuous electron beams. When the degree of chirp is very high (left column) both time-selection and energy-filtering can generate temporally and energetically highly-coherent electron pulses. Temporal selection is only limited by the pulse duration of the laser employed. For energy-filtering, a very fine energy analyzer/selector is required to generate an electron pulse comparable to time-selection. When the degree of chirp is poor (middle column), temporal selection can still produce an ultrashort electron pulse with a modest energy coherence. If there is no chirp relation (right column), such as the case for a pseudo-continuous electron beam, energy-filtering does not improve the pulse length of the electron beam, whereas time slicing can pick the ultrashort electron pulse with the energy spread unchanged.

Here, we demonstrated that the chirp coefficient, as well as the duration of chirped electron pulses, $\delta t_\in$, can be directly measured in both time and energy domains using the PINEM effect, which allows us to evaluate the intrinsic temporal width, $\sigma t_e$. Because PINEM utilizes the electron-photon interaction via a nanostructure at the specimen position, the measured values are made in situ and are direct when compared to other methods that employ a deflector, the ponderomotive force, or a transient electric field. Since the interaction is through light scattering, the temporal response is instantaneous, allowing a direct measurement of the temporal profiles of the electron and photon pulses.

Similar to the notion that an aperture and an electrostatic sector are a spatial filter and an energy filter, respectively, PINEM acts as a temporal filter for electrons with its efficiency given by $Q_n(t', \bar{\tau}_\in)$. Besides the characterization of electron pulses, it is shown that ultrashort and highly coherent electron pulses can be obtained by selecting PINEM electrons, once a chirp is established. The degree of temporal resolution is mainly determined by the pump (gate) laser employed, regardless of the electron pulse characteristics. The degree of energy resolution, on the other hand, strongly depends on the degree of chirp.

In advancing ultrafast electron microscopy, one of the main goals has been to minimize the space-charge effect and the electron dispersion, and ultimately to achieve a time resolution as short as that of the optical pulse duration. Linear space-charge effect pushes leading electrons forward and lagging electrons backward, and thus induces a position-dependent momentum shift, acting as a temporal diffusive lens. With a temporal focusing element, the longitudinal dispersion can be reversed and the ultimate time resolution depends on the final energy spread and the longitudinal emittance. Many schemes of temporal compression of electron pulses depend on the existence and modification of a chirp relation between time and energy. By measuring the chirp of the electron pulses, we can calculate the longitudinal emittance of the electron packet, from which we can estimate the temporal focusability. Furthermore, those quantities can be used to devise/examine/improve the electron pulse compression scheme.

A reflectron can temporally focus electrons down to $\sigma t_e$, as it creates energy-dependent time shift in the chirp, and $\sigma t_e$ and $\delta E_\in$ are conserved. A ponderomotive temporal lens (and a RF compressor), which induces position (time) dependent momentum (energy) shift, changes $\delta E_\in$ and consequently $\sigma t_e$, while conserving the longitudinal emittance. The (temporal) focal length, and the (temporal) focus size are inversely proportional to the induced energy spread. However, while the linear space-charge effect without the statistical noise conserves the longitudinal emittance, statistical noise due to discrete randomness in the space-charge effect, as well as inhomogeneity in the beam path, spoils $\sigma t_e$ and consequently the longitudinal emittance; these need to be avoided to achieve the ultimate in ultrafast temporal resolution.

Figures 8A, 8B, 8C:
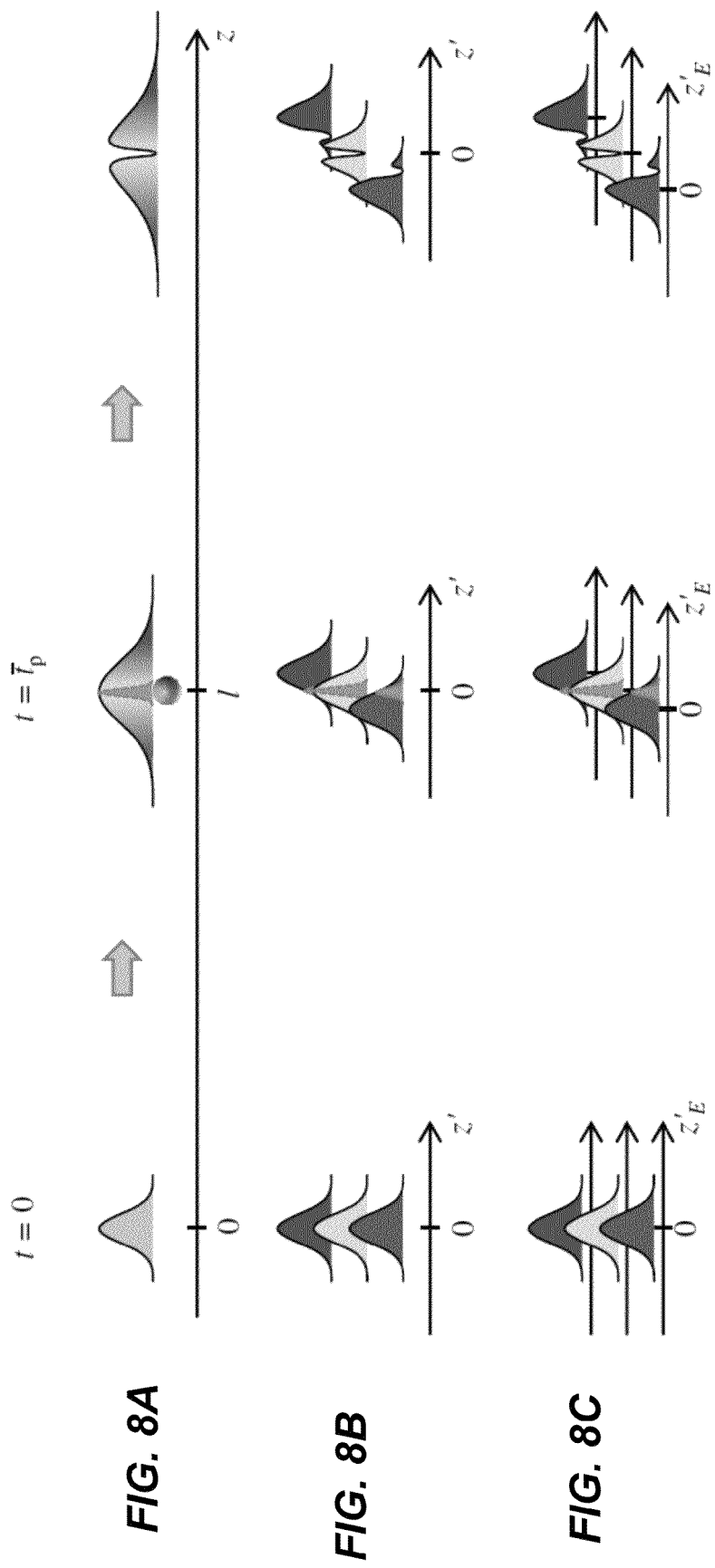
FIGS. 8A-8C illustrate spatial properties of electron pulses at predetermined times according to an embodiment of the present invention.

FIG. 8A illustrates (Top) spatial probability of an electron pulse along the coordinate, z, at three different times, t=0, $\bar{t}_p$, and later. Due to inhomogeneous energy distribution, electron pulse disperses as it propagates. A nanoparticle is at z=l, and PINEM transition due to interaction with photon is shown in green. (FIG. 8B-M*iddle*) spatial probability of three different energy electron packets in the pulse along the ensemble moving coordinate, z', at different times. (FIG. 8C—Bottom) spatial probability of three different energy electron packets in the pulse along their individual packet moving coordinate, $z'_E$, at different times.

TABLE 1

| Term | Description |
|---|---|
| z | position in a fixed spatial coordinate system |
| t | time |
| $\bar{t}_p$ | mean arrival time of photon pulse at z = Z |
| $\sigma t_p$ | temporal width of photon pulse |
| e | subscript used for a coherent electron packet |
| $\sigma t_e$ | temporal width of electron packet |
| E | energy of electron packet |
| $v_E$ | energy-dependent velocity of electron packet |
| $\bar{t}_E$ | energy-dependent mean arrival time of electron packet at given z |
| $\tau_E \equiv \bar{t}_E - \bar{t}_p$ | energy-dependent time delay of electron packet at z = l |
| $z'_E \equiv z - v_E t$ | energy-dependent moving frame coordinate system for electron packet |
| $\in$ | subscript used for an incoherent ensemble of electron with energy distribution by $P_\in(E)$ |
| $\delta t_\in$ | temporal duration of electron ensemble |
| $\delta E_\in$ | energy spread of electron ensemble |
| $\bar{E}_\in$ | mean energy of electron ensemble |
| $\bar{v}_\in$ | mean velocity of electron ensemble |
| $\bar{t}_\in$ | mean arrival time of electron ensemble at given z |
| $\bar{\tau}_\in \equiv \bar{t}_\in - \bar{t}_p$ | time delay of electron ensemble at z = l |
| $z' \equiv z - \bar{v}_\in t$ | position in a moving frame coordinate system for the electron ensemble |
| $t' \equiv -z'/\bar{v}_\in$ | relative arrival time for electron ensemble |
| $E' \equiv E - \bar{E}_\in$ | energy difference of electron packet with respect to ensemble averaged value |
| $\Delta v_E \equiv v_E - \bar{v}_\in$ | velocity difference of electron packet with respect to ensemble averaged value |
| $\Delta \bar{t}_E \equiv \bar{t}_E - \bar{t}_\in$ | arrival time difference of electron packet with respect to ensemble averaged value |
| $\Delta \tau_E \equiv \tau_E - \bar{\tau}_\in$ | time delay difference of electron packet with respect to ensemble averaged value |
| $\Delta \bar{E}_g (\bar{\tau}_\in)$ | shift of mean energy of gated electrons as a function of the delay |

TABLE 2

Observed and calculated parameters.

| | Observed | | | | Calculated | |
|---|---|---|---|---|---|---|
| $U^b$ (nJ) | $w\delta E_\in{}^c$ (eV) | $w\delta E_g{}^c$ (eV) | $w\delta\tau_g$ (ps) | $d\bar{E}_g/d\bar{\tau}_\in$ (eV/ps) | $w\sigma t_e$ (ps) | $\partial \bar{t}_E/\partial E$ (ps/eV) |
| 0.13 | 1.16 ± 0.02 | 1.00 ± 0.01 | 0.58 ± 0.01 | 0.64 ± 0.03 | 0.478 ± 0.007 | −0.148 ± 0.007 |
| 0.25 | 1.45 ± 0.02 | 1.21 ± 0.01 | 0.70 ± 0.01 | 0.97 ± 0.02 | 0.556 ± 0.005 | −0.209 ± 0.004 |

TABLE 2-continued

Observed and calculated parameters.

| | Observed | | | | Calculated | |
|---|---|---|---|---|---|---|
| $U^b$ (nJ) | $w\delta E_e{}^c$ (eV) | $w\delta E_g{}^c$ (eV) | $w\delta\tau_g$ (ps) | $d\bar{E}_g/d\bar{t}_e$ (eV/ps) | $w\sigma t_e$ (ps) | $\partial\bar{t}_E/\partial E$ (ps/eV) |
| 0.37 | 1.82 ± 0.03 | 1.45 ± 0.01 | 0.77 ± 0.01 | 1.15 ± 0.01 | 0.610 ± 0.004 | −0.205 ± 0.003 |
| 0.55 | 2.47 ± 0.04 | 1.93 ± 0.01 | 0.70 ± 0.01 | 1.94 ± 0.02 | 0.518 ± 0.005 | −0.166 ± 0.002 |
| 0.67 | 2.91 ± 0.05 | 2.06 ± 0.02 | 0.76 ± 0.01 | 1.88 ± 0.02 | 0.585 ± 0.004 | −0.153 ± 0.002 |
| 0.82 | 3.49 ± 0.06 | 2.31 ± 0.02 | 0.80 ± 0.01 | 2.02 ± 0.02 | 0.638 ± 0.004 | −0.138 ± 0.002 |

The width discussed reported here is the full-width-half-maximum (FWHM) of a Gaussian profile, evaluated by multiplying the standard deviation width with a factor of w=

$$2\sqrt{2\log 2}.$$

Laser pulse energy estimated from the known relation to electron energy spread. Deconvoluted values taking the detector resolution of $w\sigma E_a$=0.25 eV in FWHM. For calculation, $w\sigma t_p$=0.280 ps (FWHM) is invoked. For other calculated quantities, we employ $$\delta t_\varepsilon \sqrt{\sigma t_e^2 + \left(\frac{\partial \bar{t}_E}{\partial E}\delta E_\varepsilon\right)^2} \text{ and } \rho^2 = 1 - \left(\frac{\sigma t_e}{\delta t_\varepsilon}\right)^2.$$

Embodiments utilize photon-induced near field electron microscopy (PINEM) to reach new limits of temporal and spatial resolutions. Two optical femtosecond pulses are used, one of them is for the usual clocking of dynamical change but the second one is for gating (slicing) the third, imaging-electron continuous or pulsed beam. It is shown that in both cases the resolution becomes that of the optical gating pulse and not of the electron one. We also show that by using the near field of a nanoparticle it is possible to enhance contrast in imaging of materials and including biological structures.

In recent years, 4D ultrafast electron microscopy (UEM) and diffraction (UED) have been developed for the study of structural dynamics of isolated molecules, surfaces, and nanostructures. Because single-electron imaging is introduced, it is possible to reach the atomic-scale resolutions, spatially and temporally. In principle, the temporal resolution is determined by three main contributions; the excitation laser pulse duration, the electron packet duration, and the velocity mismatch between them. In practice, high voltage fluctuation and electronic jitter may also contribute. Optical pulses with duration below 10 fs are now commercially available, and a generation of attosecond extreme ultraviolet (XUV) pulses has been demonstrated. Group velocity mismatch can be overcome in reflection electron diffraction geometry, using a tilted optical pulse arrangement, and when the transmission geometry of UEM is utilized, it is not of concern; for a specimen thickness of up to 100 nm, the mismatch in time is one femtosecond (fs). Accordingly, further improvement of the time resolution requires control of the electron pulse duration.

Electron packets in ultrafast diffraction and microscopy are generated by femtosecond photoemission and acceleration to the kinetic energy of 30-200 keV, typically with an extraction electric fields of ~$10^6$ V/m. An initial emission energy spread of more than 0.1 eV results from the laser-pulse energy width and the distribution of energies determined by the work function of the cathode material. This energy distribution is directly related to the width of the electron packet:

$$\Delta t \approx \frac{d\Delta E}{v_i E_f},$$

where ΔE is the energy spread and $v_i$ and $E_f$ are the initial velocity and final energy, respectively; d is the distance of the cathode from the anode. For example, for ΔE=0.1 eV, and typical d of 0.5 mm and $E_f$ corresponding to 1 kV, the pulse width is 300 fs, and for larger ΔE, the width further increases [11].

Here, the behavior of electron packets in the near field of a nanostructure is exploited for slicing the pulses and enhancing image contrast. The strong interaction of free electrons and photons, mediated by a nanostructure (such as carbon nanotube, silver nanowire, protein vesicle, or E-coli cell) is the key for the success of photon-induced near field electron microscopy (PINEM). Herein, we discuss the concept of gating in PINEM, which makes the temporal resolution limited only by the optical pulse profile, and the near field spatial localization which leads to the enhancement of contrast in imaging.

Free electrons generally do not interact with light in vacuum as the coupling is not permitted due to momentum-energy mismatch. The mismatch condition can be overcome in certain circumstances such as inverse Cerenkov radiation, inverse Smith-Purcell radiation, Kapitza-Dirac effect, laser-assisted electron/atom scattering, among others. These effects have their origin in different interaction terms of the Hamiltonian ($\vec{A}\cdot\vec{p}$ or $A^2$, where $\vec{A}$ is the vector potential and $\vec{p}$ the momentum); for the latter effect ($\vec{A}\cdot\vec{p}$ term) the electron scatters from the potential of the atom modified by the photon interaction. In these various schemes, neither the ultrafast temporal resolution was introduced nor the spatial imaging can reach that of UEM. Moreover in PINEM, the nanostructure is central to mediating the electron-photon interaction.

When light is scattered by a nanostructure, the near field component exhibits a momentum spread, due to its spatial confinement ($\Delta x \Delta p \approx \hbar$). Furthermore, the scattering gives rise to a longitudinal component of the electric field resulting in acceleration/deceleration of the electron packet. This component at the spatial frequency that corresponds to the electron momentum change makes possible the coupling and the exchange of many quanta of photon energy. The PINEM field is given by:

$$\tilde{F}\left(\frac{\omega_p}{v_e}\right) = \int_{-\infty}^{+\infty} dz'' \tilde{E}_z(z'', 0) \exp\left[-i\left(\frac{\omega_p}{v_e}\right)z''\right], \quad (10)$$

which is the Fourier transform component of the longitudinal electric field of scattered light wave at the spatial frequency of $$\Delta k_e = k_e^f - k_e^i = \frac{\Delta p_e}{\hbar} = \frac{\omega_p}{v_e}.$$

In eqn. (10), $\tilde{E}(\vec{r},t)$ is the complex representation of the electric field of scattered light, $\omega_p$ is the angular frequency of photon, and $v_e$ is the electron velocity. The near field is relatively huge when compared with far-field detections; it is determined by the spatial geometry of the nanostructure and strength of the electric field of the incident wave, and its dielectric response in the material. It follows that due to this field the imaging electron will display in the energy domain quantized gain/loss peaks with different orders (n) i.e. ±n $\hbar\omega_p$. It can be shown that the n th order intensity is directly related to $$|\tilde{F}|^{2n},$$

in the weak interaction limit. In the strong interaction limit, the intensity is expressed in terms of a Bessel function. We note that the integration is over z which is the direction of the electron propagation, and an image in the x-y direction, obtained in parallel beam illumination, maps the field distribution of the object. Conversely, an electron beam convergent at a given (x, y) point gives the field at this particular point in space.

Because the interaction is via a particular component of scattered light, the degree of interaction depends on the distance of electron trajectory from the scattering center (electron impact parameter, b), and the incident polarization angle with respect to electron propagation trajectory. The polarization changes according to a cosine function. The PINEM field decreases exponentially as the impact parameter increases, with the decay length being on the nanoscale. With PINEM imaging, we can map the spatial profile of the field by selecting only electrons that have gained photon energy and recording the energy-selected, dark field, image. The contrast is strongest at the projected nanoscale interface and when the field is captured prior to its decay on the fs time scale. Light scattering and energy exchange are instantaneous, and, therefore, the temporal profile of the entire response is determined by the convolution of the two beams, the optical pulse and electron packet.

In order to illustrate the effect of gating electron packets using optical pulses and the role of the near field, we use the solution of the time-dependent Schrödinger equation for a free electron under the influence of a scattered electromagnetic wave. The final, post-scattering wavefunction is given as a summation over discrete momentum/energy states:

$$\Psi(z, +\infty) = g(z - v_e t, -\infty) \sum_{n=-\infty}^{\infty} \left(-\tilde{F}/|\tilde{F}|\right)^n J_n(\Omega) \exp[i(k_n z - \omega_n t)], \quad (11)$$

where $J_n(\Omega)$ is the Bessel function of the first kind, whose argument is given by $$\Omega(z'; \tau) = \frac{e}{\hbar \omega_p} |\tilde{F}| \exp\left[-\frac{(z' - v_e \tau)^2}{4 v_e^2 \sigma_p^2}\right].$$

Here, $z'=z-v_e t$, and $\sigma_p$ and $\tau$ are the photon pulse duration and time delay between electron and photon pulses, respectively. The frequencies and momenta are simply given by: $\omega_n = \omega_e + n\omega_p$ and $k_n = k_e + n(\omega_p/v_e)$, which express the energy and momentum of the electron after a net n photon absorption/emission. Finally, the envelope function of the initial state, which is taken to be of a Gaussian profile, can be written as:

$$g(z - v_e t, -\infty) = \left(\frac{1}{\sqrt{2\pi} v_e \sigma_e} \exp\left[-\frac{(z - v_e t)^2}{2 v_e^2 \sigma_e^2}\right]\right)^{\frac{1}{2}}.$$

It is more convenient to transform $I(z)$, $\psi\psi^*$, the propagating wavepacket intensity spatial distribution at given time, into $I(t')$, flux or the temporal profile at a fixed position. Using $I(z)dz=I(t')dt'$, where the arrival time, $t'\approx -z'/v_e = -(z-v_e t)/v_e$, is defined with respect to the center of the packet, we obtain the n th state (sub-packet) intensity as:

$$I_n(t') = I_e(t') Q_n(t'; \tau), \quad (12)$$

where $$I_e(t') = v_e |g(v_e t', -\infty)|^2 = \frac{1}{\sqrt{2\pi} \sigma_e} \exp\left[-\frac{t'^2}{2\sigma_e^2}\right]$$

is the electron total intensity (temporal) profile and $$Q_n(t'; \tau) = |J_n(\Omega(t'; \tau))|^2$$

is the n th order transition probability density. The properties of Bessel function, $J_n(\Omega) \to 0$ as $\Omega \to 0$ for $n \neq 0$, dictates that the PINEM intensity becomes significant only during the optical pulse duration, i.e. when $$|t'| < \sigma_p \ll \sigma_e \text{ at } \tau = 0.$$

therefore, the pulse duration of the electron packet that has gained energy becomes comparable to that of the photon pulse duration, and it even becomes shorter than the optical duration for higher n. This is the basis of the slicing concept; one optical pulse is used for the gating of the electron packet and another for the clocking of the event.

Figure 9:
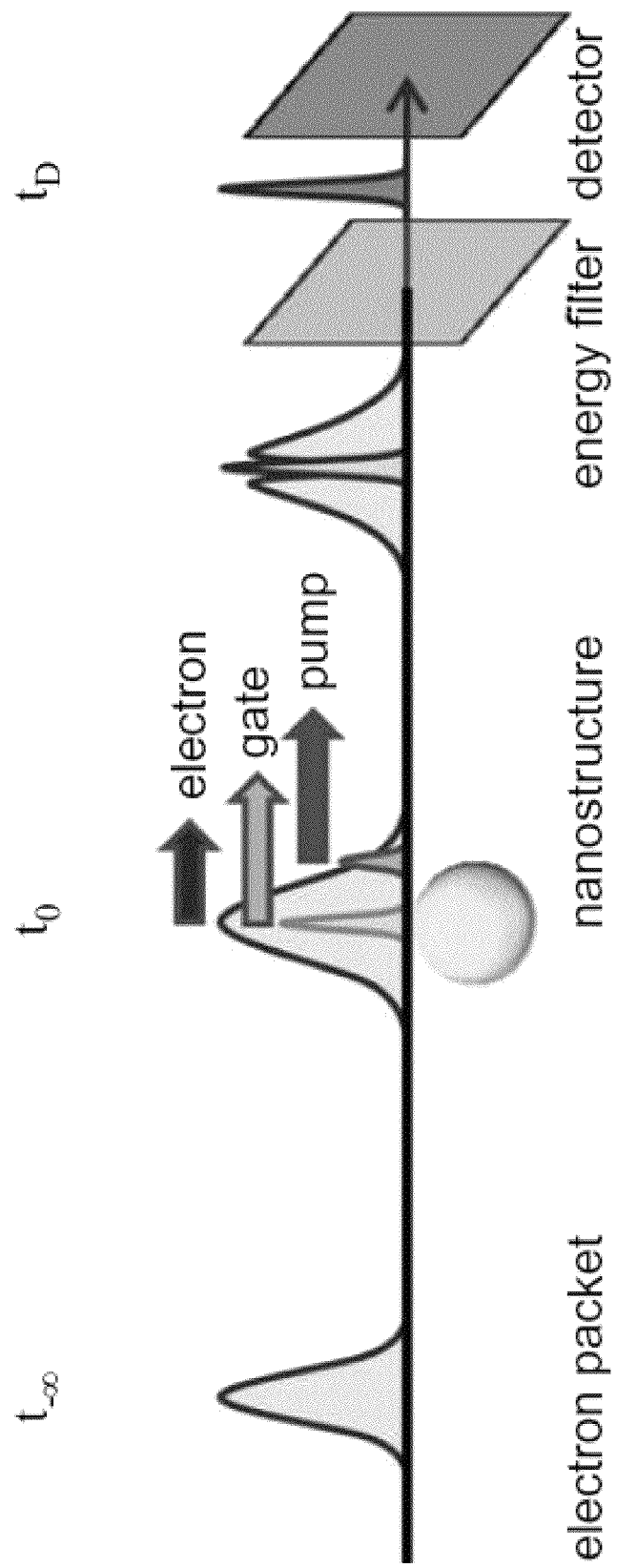
FIG. 9 illustrates a schematic of an experimental slicing mechanism according to an embodiment of the present invention.

The temporal gating scheme is illustrated in FIG. 9, which shows a schematic of experimental slicing mechanism. The initial electron packet overlaps with the optical gate pulse at the nanostructure. The optical pump pulse initiates the dynamics with a time delay from the gate pulse. The arrows depict relative propagation velocities. The zeroth order (n=0) state is depleted as a result of photon-electron energy exchange but with a duration comparable to that of the gate pulse. The cut-off energy filter is for selection of PINEM intensities for electrons which gained energy from the photons.

An electron packet is generated in UEM and arrives at the nanostructure where it overlaps with the optical gate pulse. The "sub-packet" of the electron which temporally coincides with the optical gate pulse will either gain or lose kinetic energy that equals to multiples of photon energy. Since the electron-photon energy exchange occurs only when the electron, photon, and the particle are at the same time and in the same place, we can use this concept of PINEM to ultrafast-gate the electron packet with a very narrow temporal and spatial window. This gating results in the slicing of the electron packet and in that sense can be likened to slicing, using wigglers, of femtosecond X-rays from synchrotron radiation. However, our approach utilizes the nanostructure for slicing and the electron packet is not required to be relativistic as in the case of synchrotron radiation.

Figure 10A:
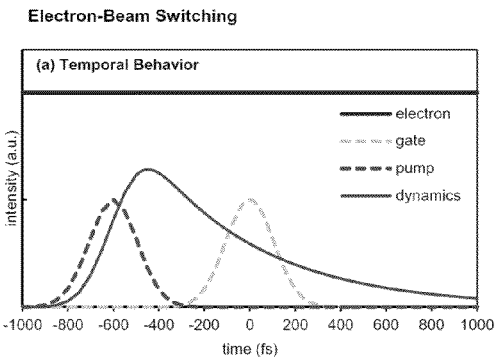
FIGS. 10A-C illustrate electron continuous-beam switching according to an embodiment of the present invention.
Figure 10B:
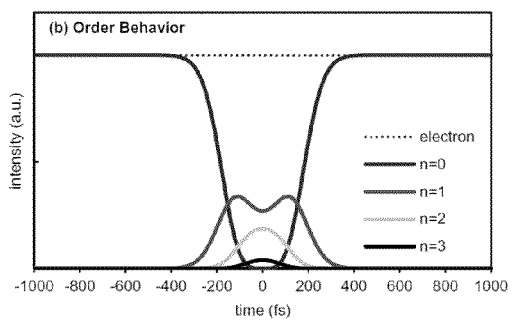
Figure 10C:
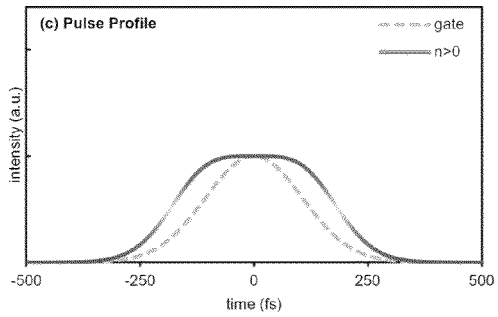

The above described approach can be used to switch a continuous electron beam or to slice a pulse. FIG. 10 illustrates electron continuous-beam switching. FIG. 10A illustrates the temporal behavior of the gate and pump optical pulses ($\sigma$=106 fs), and the continuous electron beam ($\sigma_e \to \infty$). FIG. 10B illustrates the order behavior of the temporal profiles of the populations of electrons for different orders (n=0, 1, 2, 3, . . . ). FIG. 10C shows the comparison of the gated electron packet and the gate optical pulse profile. The saturation feature is due to the large depletion of n=0 peak.

FIG. 10A shows the case of continuous beam gated by a fs pulse, following a fs pump pulse, and with a system decay time of 500 fs. In FIG. 10B, the individual sub-packets of the electron which gained multiple photon energies, and the zeroth order sub-packet, which is depleted by the optical gate pulse, are displayed. The full width half maximum (FWHM) of the optical pulse is 250 fs ($\sigma$=106 fs). For this case, where the electron beam is continuous ($\sigma_e \to \infty$) i.e., not pulsed, the gate actually creates a pulsed beam. By adjusting the delay time between the gate pulse and the optical pump pulse, the dynamics clocked by the pump pulse can be investigated with an ultrafast temporal resolution when selecting those electrons with a higher kinetic energy. FIG. 10B compares the temporal profiles of the optical gate pulse and the electron sub-packet (rainbow) with higher kinetic energies, i.e., $$I_+(t'; n>0) = \sum_{n=1}^{+\infty} I_n(t').$$

It is to be noted that higher n energy exchanges have a narrower width, of course with a decrease in intensity; in the weak interaction limit $$\sigma'_n \approx \sigma_p/\sqrt{n}.$$

In FIG. 10C, shown is the switching of the continuous beam into a pulsed beam with duration comparable to the width of the gating pulse; the saturation is because of the large depletion at the fluence used.

Figure 11A:
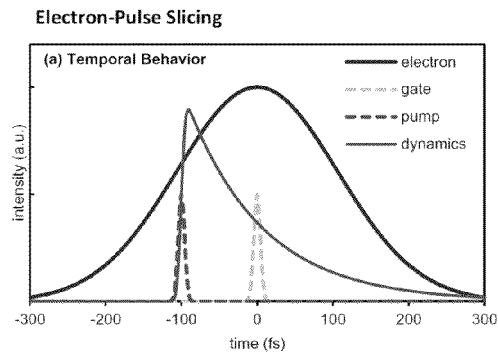
FIGS. 11A-C illustrate electron pulse slicing according to an embodiment of the present invention.
Figure 11B:
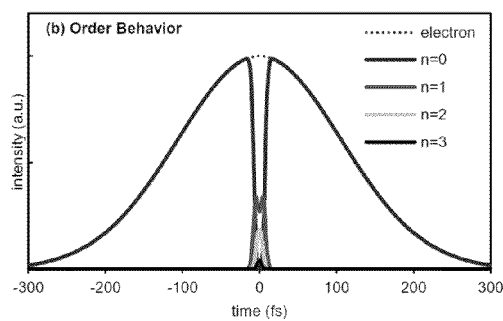
Figure 11C:
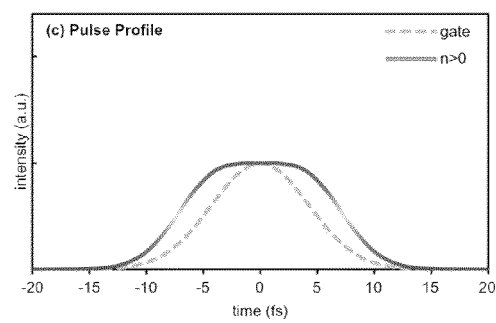

Next we considered a broad electron packet and used the optical pulses and nanostructure for slicing it. FIG. 11 illustrates electron pulse slicing. FIG. 11A illustrates the temporal behavior of the gate and pump optical pulses ($\sigma_p$=4 fs), and the pulsed electron beam ($\sigma_e$=106 fs). FIG. 11B illustrates the order behavior of temporal profiles of the populations of electrons for each order (n=0, 1, 2, 3, . . . ). FIG. 11C illustrates the comparison of the gated electron packet and the gate optical pulse. The saturation feature is due to the large depletion of n=0 peak.

In FIG. 11, we show the results for $\sigma_e$=106 fs and $\sigma_p$=4 fs. In this case, we expect effective shortening of the electron pulse down to the optical pulse width. The results in FIG. 11 confirm this hypothesis and provide a novel methodology for reaching a few femtosecond and possibly attosecond, resolution, in UEM. FIGS. 11A and 11B give the temporal and order behavior whereas FIG. 11C depicts the pulse profile.

Several advantages are worth noting. First, although the temporal resolution becomes limited by the duration of the optical gate pulse, no band pass filter is needed. In other words, a high pass filter is enough in this approach; the energy-gained electrons, n≥1, are selected. In this case, when n=1, $\hbar \omega_p$=2.39 eV at 519 nm. A band pass filter whose energy width is chosen according to the temporal resolution desired can, in principle, improve the temporal resolution, but in PINEM higher temporal and spatial resolutions are controlled by the near field of the nanostructure. Another advantage of the approach is the elimination of jitter, because gating is done optically and fluctuation in electron energy and in electronics, which result in a temporal broadening, becomes irrelevant. A third one is that the scheme is also spatially selective as it is possible to image on the nanoscale, because the field integral, $\tilde{F}$, decays exponentially with distance from the nanostructure with a decay length of nearly a, the radius of nanosphere.

Even though the effect is strong enough to completely deplete the n=0 peak (see FIGS. 10 and 11), the optical gate pulse overlaps the envelope for a very short time, leaving unchanged portions of the electron packet which do not coincide with the optical gate pulse. The efficiency of conversion can be written as ½ ($\sigma_p/\sigma_e$), where a factor of half arises from the fact that we only select the sub-packet that gained energy. Naturally, care has to be taken to make sure that the optical gate pulse does not induce unwanted dynamics and the excitation clocking pulse does not cause any photon energy exchange with the electron packet. The tunability and fluence of fs optical pulses are two parameters that can be varied for these selectivities.

Light scattering by nanostructures is treated using the Mie equation, but when the particle size is much smaller than the optical wavelength, Rayleigh dipole approximation is invoked. The PINEM field, $\tilde{F}$, can be evaluated numerically using the Mie solution and analytically using the Rayleigh (near field) approximation. For a sphere, $\tilde{F}$ outside the particle (b>a) is given by:

$$\tilde{F} = -i(\tilde{E}_0 \cos\phi)\chi_s 2a^2 \Delta k_e \{\Delta k_e a K_1(\Delta k_e b)\}, \qquad (13)$$

where $E_0$, $\phi$, $\chi_s$ are, respectively, the electric field amplitude, the laser polarization angle, and the spherical susceptibility defined as $\chi_s=(\tilde{n}^2-1)/(\tilde{n}^2+2)$. The impact parameter is b, and a is again the radius of the particle. $K_1$ is the modified Bessel function of the second kind. The curly bracket in eqn. (13) exhibits an exponentially decaying function of the impact parameter, and the 1/e decay length, $\delta$, of the PINEM field in the exponential decay regime is given by $$-\frac{1}{\delta} = \lim_{b \to a} \frac{\partial \log F}{\partial b}.$$

For small spheres, the decay length reaches the radius value, $\delta$=a. Therefore, the PINEM field in this case is only significant within a length scale that is comparable to the particle size.

When the electron propagates through the material (b<a), the integration for the PINEM field, $\tilde{F}$, needs to be done piecewise for the regions outside and inside the material. An analytical expression for the field for such a case cannot be obtained, and it has to be numerically evaluated. Nevertheless, it is expected that the field should decrease as the electron trajectory approaches the center of the particle, due to the symmetry of the scattered wave.

Figure 12:
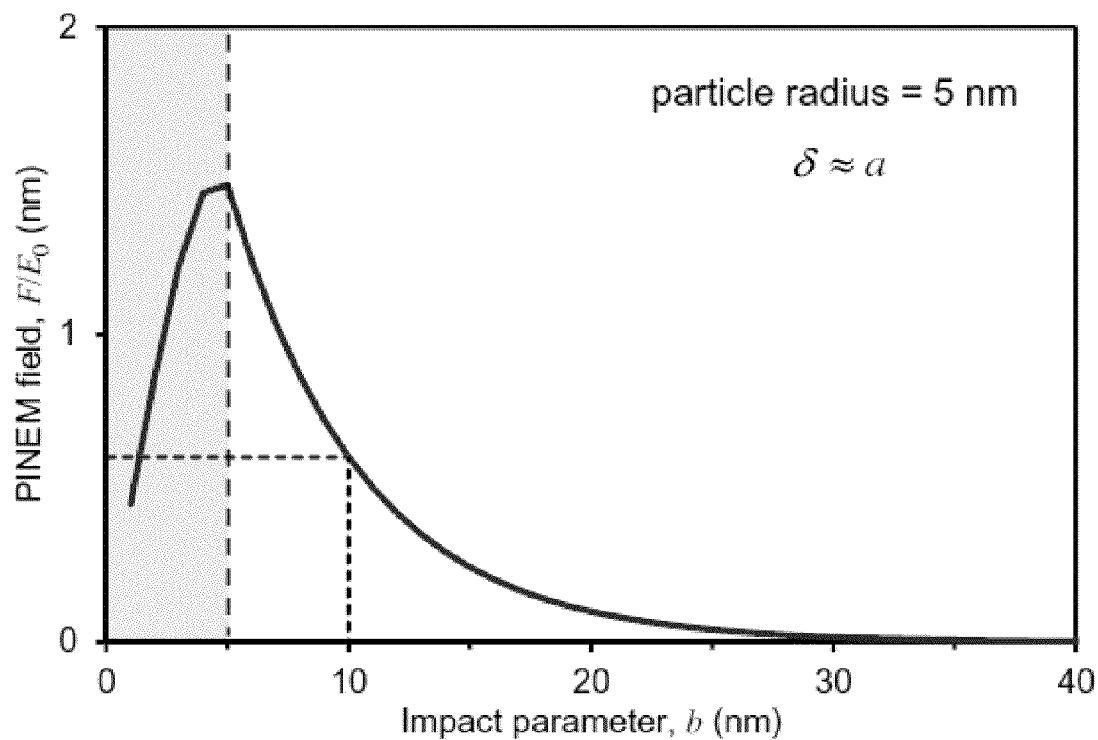
FIG. 12 illustrates spatial location on the nanoscale according to an embodiment of the present invention.

FIG. 12 illustrates spatial localization on the nanoscale. Shown is the dependence of the PINEM field on the impact parameter, b, inside and outside of a 5 nm radius nanoparticle of gold. Note the exponential behavior outside the particle interface, in this case vacuum.

FIG. 4 shows the PINEM field (divided by the incident electric field amplitude, $E_0$) for 5 nm radius gold particle at 519 nm illumination. (Unlike the case of the three pulse scheme described in the previous section, here we only employ one laser which is coincident with the electron pulse.) It indicates that the PINEM field is (almost linearly) proportional to the impact parameter for b<a, and exponentially decays for b>a, as indeed expected physically. The decay length scale is similar to that of the particle radius.

Figure 13:
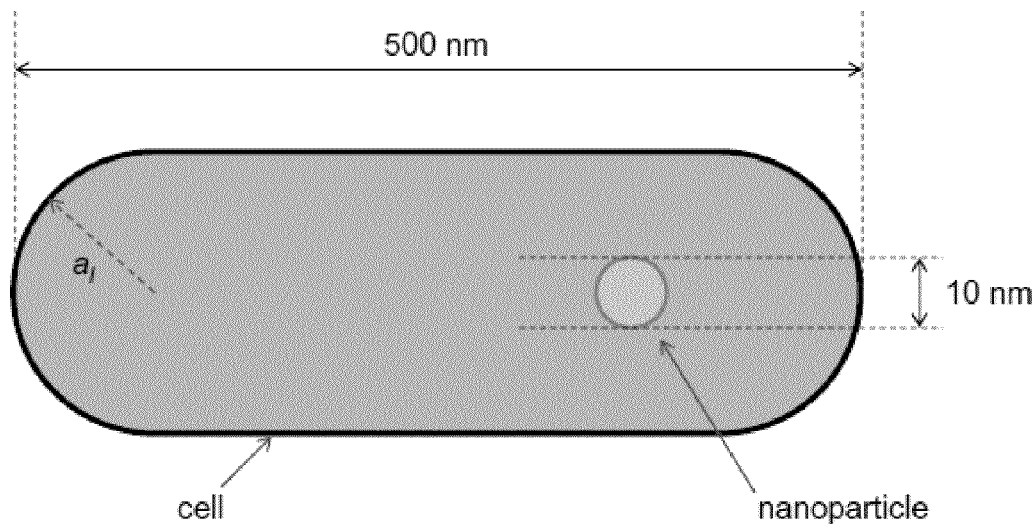
FIG. 13 illustrates PINEM imaging of a single particle in a dielectric medium according to an embodiment of the present invention.
Figure 14A:
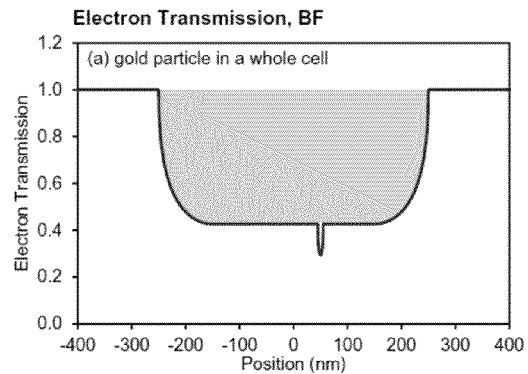
FIGS. 14A-F illustrate electron transmission and PINEM imaging according to an embodiment of the present invention.
Figure 14D:
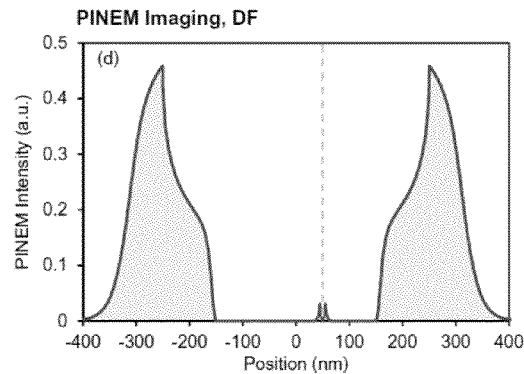
Figure 14B:
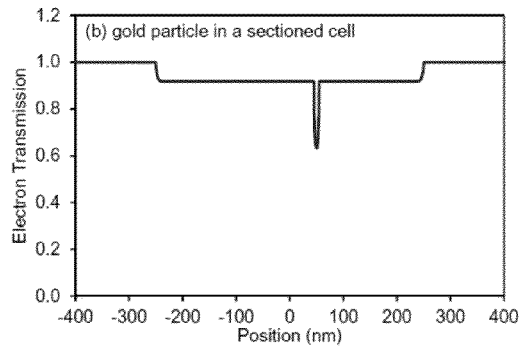
Figure 14E:
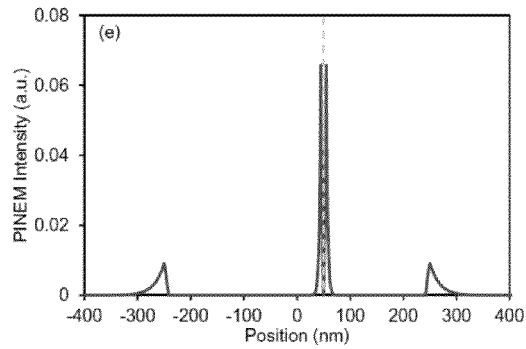
Figure 14C:
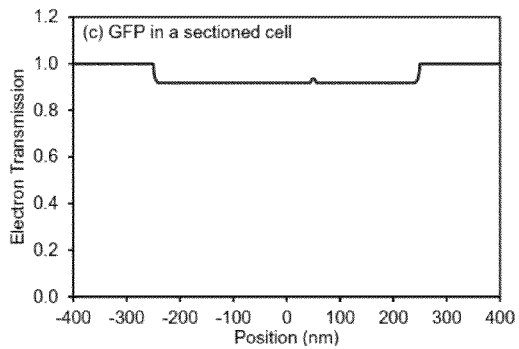
Figure 14F:
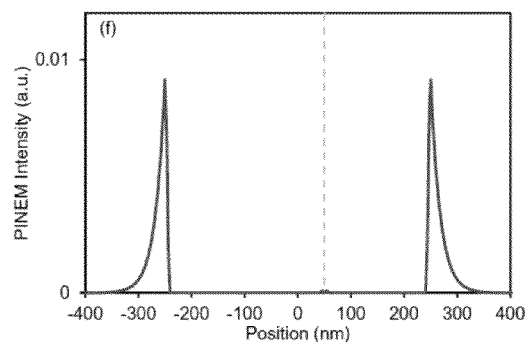

This feature of spatial localization here we exploit for contrast enhancement and for PINEM imaging that may be relevant to immunolabeling of cells. FIG. 13 illustrates the scheme where a nanoparticle inside a cell is imaged by PINEM. FIG. 13 illustrates PINEM imaging of a single particle in a dielectric medium. Schematic of the gold nanoparticle in a cell. The dimension of the cell is not to scale. A cell (either native or frozen) is placed in vacuum (or dielectric medium). A 10 nm diameter gold particle attached to an antibody specific to an antigen is placed inside the cell. The cell is then illuminated with a femtosecond laser light, of which a fraction is transmitted and is scattered by the nanoparticle inside. Depending on the geometry of the cell, the transmitted light wave inside the cell may be refracted and/or slightly converged. However, the wave can be still approximated as a planar one, with a refracted angle, for a relatively small particle.

FIG. 14 depicts the results for the spatial profiles of bright-field (electron transmission) and dark-field (PINEM image) intensities using a 10 nm gold (or protein) particle in 500 nm whole or sectioned cell. The PINEM signal is generated by the particles (gold or protein) and by the cell membrane due to their evanescent scatterings, and these are the interface areas that will "light up". As illustrated in FIG. 14, electron transmission (bright field) and PINEM (dark field) imaging are shown. Bright-field (left) and PINEM (right) images of FIG. 14A the gold particle in a whole cell, FIG. 14B shows the gold particle in a sectioned cell, and FIG. 14C shows the green fluorescent protein in a sectioned cell. Note the contrast difference and the background-free feature of PINEM, DF imaging.

For the gold particle ($\tilde{n}=0.64+2.05i$), the wavelength of 519 nm is near the Fröhlich resonance at 2.53 eV, which enhances absorption and scattering. In the case of the green fluorescence protein ($\tilde{n}=1.5$), light is off resonance with the absorption at 479 nm (the stronger absorption peak is at 395 nm). Because of the spatial localization discussed above, the PINEM image exhibits a bimodal intensity profile with sharp maxima at the interfaces. Such profile enables one to precisely locate the particles (interfaces) from the PINEM images. More importantly is the enhanced PINEM contrast at the particle position (green dotted line) inside the cell.

One significant advantage of PINEM imaging is that it is background free, the analogue of dark field imaging but without conventional diffraction selection. This feature greatly enhances the contrast, as can be seen in the results of FIG. 14, especially for sectioned cells when the thickness is relatively small. Another useful feature results from the fact that the pulsed light enhances the contrast without necessarily involving externally staining, as long as there is refractive index difference. The wavelength on-resonance tuning may be used to further enhance the magnitude of the PINEM field, particularly for "light particles" as in the case of GFP. The PINEM signal is roughly proportional to the fourth power of the particle size, $I_+ \propto a^4$, and consideration of the particle size and photon fluence will determine the overall sensitivity. Finally, the light polarization may be exploited to obtain tomographic images for different positions and interfaces.

Thus, embodiments provide an approach for electron microscopy imaging using the near field characteristic of nanostructures. By introducing a gating optical pulse to the pump-probe configuration of UEM the temporal resolution of the electron packet can reach the commercially available 10 fs resolution of optical pulses, and possibly the attosecond domain. When using nanoparticles, it is shown that their localized, nanoscale near field enhances imaging contrast which enables the visualization of material interfaces and provides dark field positioning of single particle in cellular system. These temporal and spatial localization features are made in situ with the zero of time being well defined for dynamical studies and maintaining robust the various domains of ultrafast electron microscopy. Our slicing scheme can be utilized not only for gating, but also to directly measure the electron pulse duration with optical precision and in situ at the probing region.

Single-particle imaging of structures has become a powerful methodology in nanoscience and molecular and cell biology. Here, the development of sub-particle resolved imaging with space-time-energy resolutions of nanometers, femtoseconds and milli-electronvolts, respectively, is discussed. By using scanning electron probes across an optically excited nanoparticle and interfaces, we simultaneously construct energy-time and space-time maps. Spectrum images are then obtained for the nanoscale dielectric fields, with the energy resolution set by the photon rather than the electron, as demonstrated here with two examples (silver nanoparticles and the metallic copper/vacuum interface). This development thus combines the high spatial resolution of electron microscopy with the high energy resolution of optical techniques, both with the ultrafast temporal response, opening the door to various applications in elemental analysis, and for mapping of interfaces and plasmonics.

Substantial progress has been made in the imaging of matter at the smallest length scale and shortest time response, using a range of optical and electron-based methods. Recent developments in electron microscopy have enabled studies of nanostructures with remarkable spectral and spatial resolutions.

Embodiments provide ultrafast spectrum imaging (USI), with sub-particle spatial resolution, in electron microscopy. The electron beam is focused down to the nanometer scale, the electron packet has femtosecond (fs) duration, and the energy resolution, optically induced, is in the meV range; the energy and temporal resolutions are no longer limited to those of conventional microscopy imaging. At every probe position across a nanoparticle, or at an interface, the electron energy gain spectrum can be acquired as a function of time delay between fs optical and electron pulses, and imaging is complete when simultaneously the focused probe is scanned.

The potential of the technique is demonstrated using two cases. For plasmonic Ag particles we observe the polarized electric field distribution, the fs dielectric response and the nm spatial localization of the particle. For the Cu metal-vacuum interface, we determine the effective decay length (nm scale) and the evolution (fs resolution) of the plasmonic field, and identify the strong and weak regions of the field by scanning the probe away from the interface. We anticipate a broad range of applications of USI because of the dimensions it simultaneously enables for imaging in space, time and energy.

Knowledge of the dielectric response of materials and biological systems to an optical excitation is essential to the determination of the strength and extent of interaction between electromagnetic waves and systems under study. For example, bulk materials' reflection and absorption are dictated by such responses at the incident wavelengths. At the nanoscale, where the boundaries can have a dramatic effect on the way light manifests itself, the response can include spatially localized plasmonic fields. It follows that an understanding of the dynamics at the microscopic level, with combined spatial, spectral and temporal resolutions, would be indispensable, both at the fundamental level as well as for various applications.

For bulk systems, there exist various optical techniques for measuring the dielectric response, and these include ellipsometry, Fourier transform infrared and Raman spectroscopy. In the frequency domain, these techniques can readily reach the energy resolution necessary to differentiate vibrational and rotational modes in molecules (meV and sub-meV) and collective vibrational excitations in solids (phonons). In the spatial domain, however, these techniques are limited by diffraction effects and, hence, they exhibit a typical resolution of several hundreds of nanometers at the visible wavelengths. Modern optical methods have enabled improvement of resolution beyond the diffraction limit in certain circumstances but they cannot provide the spatial resolution of electron microscopy which is currently in the sub-angstrom regime.

Converged (focused) semi-relativistic electrons, with their picometer wavelength, provide the means to study time-averaged images of single particles, molecules and interfaces. When these probes are combined with the scanning and spectrometric capabilities of electron microscopes, detailed analysis of a specific energy loss with very high spatial precision is possible. The rich applications of this methodology in (sub)nanoscale science began with the mapping of charged states of silicon and carbon atoms across interfaces. Subsequently, single atoms inside nanotubes, solids and atomic columns of crystals were visualized with spectrum imaging of a specific core loss, and recently localized surface plasmons on a silver nanoparticle were mapped by employing the low-loss region of the electron-energy-loss-spectra (EELS). The development of aberration-corrected microscopes has provided electron probes with enough sensitivity to achieve spectrum imaging with sub-angstrom resolution and sub-minute acquisition time.

Although the combination of real-space imaging and EELS formed the basis of a powerful technique, both the time and energy resolutions are still dictated by limitations of the microscopes used. The temporal resolution is controlled by the speed of the acquisition time of the detector (~30 milliseconds), rendering many phenomena that occur on the fast/ultrafast time scale inaccessible to such microscopes. The energy resolution in EELS is typically limited to 0.4 eV to 1 eV, depending on the type of the electron gun used. With the advent of monochromated microscopes, it became possible to improve the resolution to 100 meV. Even with this impressive improvement, the energy resolution is still far below that of optical techniques. Moreover, the important visible-infrared spectral region is difficult to study, especially because this region is usually obscured by the tail of the large zero-loss-peak (ZLP). The ideal imaging technique would, therefore, combine the spatial characteristics of electron microscopy with the spectrum characteristics of optical microscopy, simultaneously with ultrafast temporal resolution.

Adapting the ultrafast convergent beams has enabled Kikuchi diffraction and dark-field real-space imaging. For near-field imaging, applied parallel-beam illumination with very wide energy selection has been used; in contrast, here we invoke a focused scanning beam and energy is specified by the photon frequency. There were some concerns about the temporal resolution of a tightly focused ultrafast probe, because the focused area is very small and space-charge effects may broaden the pulse. Here it is shown that there is no loss of the temporal resolution even in a 10 nm probe. The spectral resolution is set by the photons, not the electrons, as discussed below.

The USI setup is displayed schematically in FIG. 15A, which shows the schematic setup for ultrafast spectrum imaging. A femtosecond nanoscale electron probe (here 10 nm in diameter) is scanned across a graphene-supported plasmonic Ag nanoparticle that has been optically excited by a green laser pulse at 2.4 eV. At every probe position and femtosecond time delay, electron energy gain spectra are acquired to map the space-time-energy coordinates, as shown with typical frames in the top-right. Shown also are the bright-field image of the particle (with edge length 130 nm) (FIG. 15C—left-bottom), and the field distributions in three dimensions together with projections at two time delays.

Following optical excitation, the fs electron packets were focused onto a nanoparticle placed on a graphene substrate. At every spot position, a temporal scan was performed with 100 fs step duration and the electron energy gain and loss were recorded for every time step, relative to the time zero defined by the initial excitation. The probe was then scanned across and in the vicinity of the particle. This way it was possible to form phase-space (time-energy) images as a function of the probe position and with sub-particle spatial precision (FIG. 15B, right). The data were then analyzed for all frames defined by their time, energy and spatial coordinates to make USI movies, as shown in FIGS. 16A-F.

FIGS. 16A-F illustrate USI time and order frames of the plasmonic triangular particle. Energy gain images at +1hv (left column), +2hv (middle column) and zero energy gain (right column) are obtained for the Ag particle from the gain intensity at different time delays and probe positions (for energy gain spectra see FIG. 17A). The bottom row shows the temporal evolution after 200 fs, which maps the dynamics of evanescent electric fields excited by the linearly polarized laser pulse. The intensity behavior of the ZLP is reversed compared to energy gain images (see text). The intensities are proportional to the height of the cylinders which are false-color mapped. Top and bottom rows share the same color scale designated by the bar. The spatial dimensions (nm units) in the lateral plane are indicated on the axes of the ZLP (n=0) at t=0 and are the same for all frames.

From these frames, it was possible to visualize the spatiotemporal dielectric response of the plasmonic particle following excitation with visible light. We emphasize that the observed behavior is at the exact pump energy of 2.4 eV with the energy spread limited only by the few meV width of the initiating (pump) optical pulse. This is to be compared with the un-pumped EELS studies where the energy resolution is typically 1 eV. Moreover, when the pump-laser wavelength is scanned, USI has the potential of mapping changes in the plasmonic fields with the energy and spatial resolutions respectively set by optical and electron microscopy characteristics.

The inelastic loss and gain features seen in the energy-time images (FIG. 15, right and figures discussed below) at the multiples of the pump-laser energy (±nhv, where n is the order number) are a direct result of photon exchange between the electron packets and the localized evanescent electric field of the particle. In the absence of external electromagnetic excitation, the inelastic interaction between electrons (pulsed or continuous) and matter exclusively involves energy-loss. Once the structure is illuminated by external photons, the electrons may also gain energy from these photons, offsetting the collisional energy-loss phenomenon. Moreover, the cross section of electron energy gain (EEG) events depends on the pump laser fluence and is typically much higher than that of conventional energy loss processes, such as those due to collective and single valence electrons. This ultrafast phenomenon has recently been experimentally observed in our laboratory and was theoretically investigated by several groups. When it was invoked for real-space imaging it was dubbed photon induced near field electron microscopy (PINEM).

Photons and electrons (near-relativistic) do not effectively couple in free space because the difference between their wavevectors (momenta) is so large. One way to increase the coupling efficiency is to introduce a spatial confinement, or photon field distribution, along the direction of electrons' propagation. Nanoscale objects with their localized fields provide the necessary momentum conservation requirement for electrons to effectively interact with photons through the reciprocity of the uncertainty principle ($\Delta x \Delta p \sim h$). Because these interactions are inelastic, there is a force acting on the electron and the confined electric field has to be parallel to the electrons' trajectory. In the classical picture, the process can be understood as acceleration (energy-gain) and deceleration (energy-loss) of electrons in the spatiotemporal field. It is these confined fields that USI explores.

In FIG. 16, the reconstructed USI frames at +200 fs and at time-zero are shown for the gain of one quantum (+1hv), two quanta (+2hv), and for no energy gain, i.e. zero loss peak. The probe position, diameter and nanoparticle boundaries are all measured from the bright field images and are shown to scale on the axes of FIG. 16. Examining the time-zero frame for (+1hv) mapping reveals that the strongest energy gains are localized at the left edge and at the right vertex of the triangular particle with almost none occurring in the middle. The (÷2hv) frame further confirms this observation. More importantly, because it is a two photon gain (n=2) process, the (+2hv) frame maps the electric field at its strongest locations, in analogy with pulse clipping, hence improving spatial localization. The field is concentrated around the apex, within a ~20 nm diameter area, and at the opposite left edge, within an area of ~40 nm diameter. The ZLP frame shows a complementary behavior to the energy gain frames with reversed intensity distribution, as expected, although there is less observed localization because this frame contains contributions from all n. This detailed spatial behavior is accessible because of the resolution inherent in USI and its sensitivity to capturing images before the field decays on the fs time scale.

After 200 fs have elapsed following excitation, the intensities of both one photon and two photon mapping have dropped as a result of the temporal response of the evanescent field and the excitation laser. The (+2hv) image diminishes faster than the (+1hv) image, rising and decaying in σ=220 fs vs. 290 fs for the first order response. This improvement in temporal resolution of higher orders has been observed in PINEM studies. However, individual orders were not used for imaging due to the use of parallel beam illumination and the large window of energy filtering. The temporal narrowing is understood because higher order energy gains have a power-law dependence on the excitation pulse intensity, and, hence, they effectively reduce pulse duration; for instance, two photon gain with a Gaussian pulse reduces the width by √2, in accordance with taking the square of the Gaussian. This improves the temporal resolution of the higher order USI frames, beyond the original pulses used.

The observed spatial behavior of the Ag nanoparticle can first be qualitatively understood by considering the linear polarization of the excitation light and the pertaining length scales. The triangular particle has a thickness of 20 nm (measured by low-loss EELS) and an edge length of 130 nm which are smaller than the wavelength of the incident green photons (518 nm). This implies that the quasi-static approach of the Rayleigh limit can be invoked as a first order approximation of light-matter interaction. In this regime, the conduction band charge density of the metallic particle exhibits a dipole-like behavior (for spherical particles) with a well-defined polarization direction, but the triangular shape may force charge redistribution towards the vertices through repulsion. These surface charge oscillations create an evanescent electric field (as described by the Poisson's equation) which is imaged using USI, as shown in FIG. 16. The more complete Mie theory extends the dipolar behavior by including retardation effects and damping mechanisms.

Figure 17A:
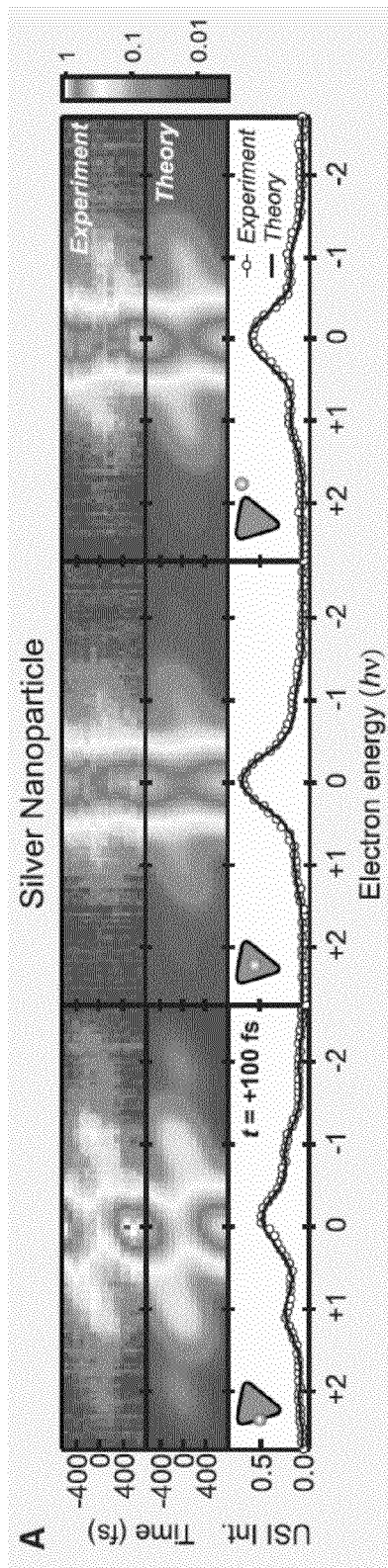
FIGS. 17A-B illustrate experimental and theoretical phase-space (time-energy) images according to an embodiment of the present invention.
Figure 17B:
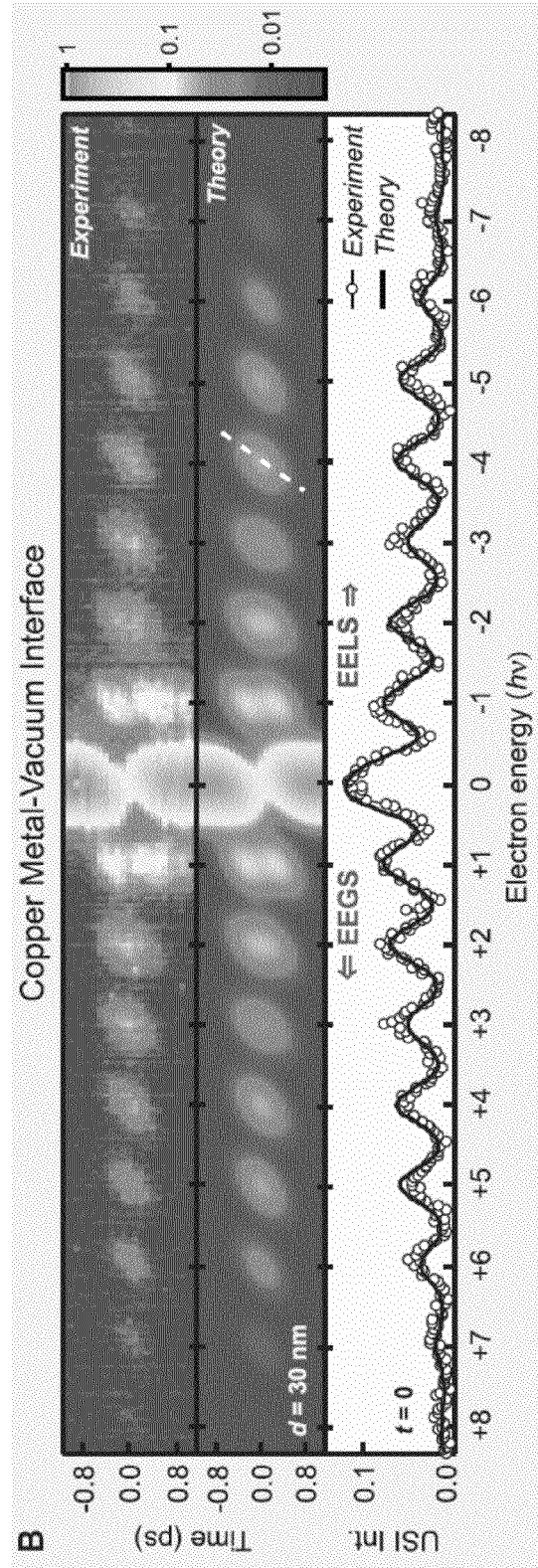

To quantify the nature of the field, we performed theoretical calculations and compared the results with the experimental phase-space images for three different probe positions (FIG. 17A). FIG. 17A shows experimental and theoretical phase-space (time-energy) images as a function of probe position. A single spectrum at t=+100 fs is shown at the bottom of each image; experimental (circles) and theoretical (solid lines). The theory reproduces the experimental results very well; the time dependent Schrödinger equation is used for the theoretical calculations without prior knowledge of the shape or strength of the field. The false color scale is logarithmic and the schematic insets show the probe position relative to the particle in space. FIG. 17B shows phase-space images and time-zero energy spectrum (bottom) of the Cu metal-vacuum interface. The data is taken at 30 nm distance from the interface and in the vacuum. Seven energy-gain (EEGS) and loss (EELS) orders, in the units of hv=2.4 eV, are clearly visible in both the experimental data and the theoretical calculations. The inclination with varying slopes for each order is indicated by a dashed line.

The theory reproduces the experimental results remarkably well, further confirming that the strongest fields are close to the apex and edge of the particle and the weakest one is at the center of it. The time-dependent Schrödinger equation is solved for the three body (electron-photon-nanostructure) interactions, giving an analytical relationship between the EEGS intensities and the electric fields involved. The experimentally measured EEGS signal is related to the integrated z-component of the electric field given by eq. 14:

$$U(\vec{r}_{xy}) = \frac{q_e}{hv} \left| \int_{-\infty}^{+\infty} E_z^n(z, \vec{r}_{xy}) \exp(-tz/b) dz \right|, \quad (14)$$

where b, the characteristic impact parameter in EELS, is given by $\hbar v_e/hv$; hv is the photon energy of the excitation pulse, $v_e$ the speed of semi-relativistic electrons, $q_e$ the unit electric charge, and $E_z^m$ the complex electric field parallel to the trajectory (z) of the electron. Here, we introduce the $\vec{r}_{xy}$ vector to account for the different probe positions that are in the x-y plane. It follows that using the USI results and employing a least-square fit procedure, the field strength, $U(\vec{r}_{xy})$ can be obtained as a function of probe position. These dimensionless quantities have the values: $U(\vec{r}_1)=1.88$; $U(\vec{r}_2)=0.93$; and $U(\vec{r}_3)=1.24$. Thus, without prior knowledge of the particle's shape or the excitation laser's polarization, the electric field can be quantified with sub-particle spatial resolution.

Figure 18A:
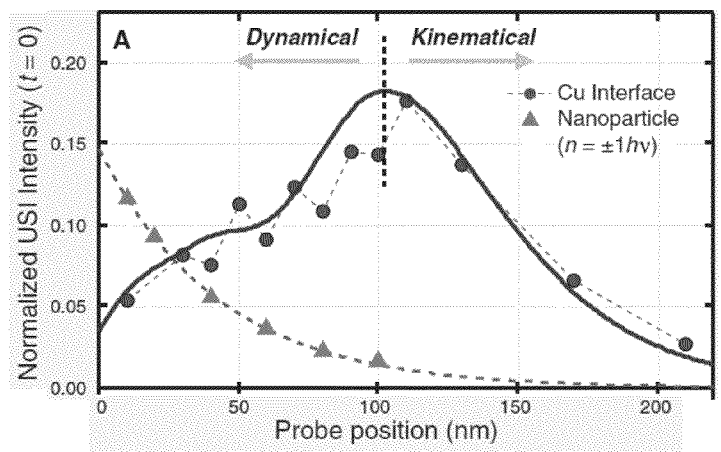
FIGS. 18A-D illustrate probe scans at the Cu metal-vacuum and Ag nanoparticle-vacuum interfaces according to an embodiment of the present invention.
Figure 18B:
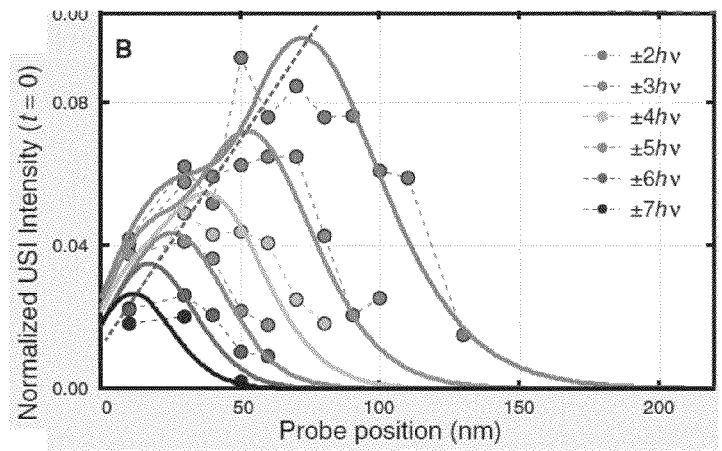
Figure 18C:
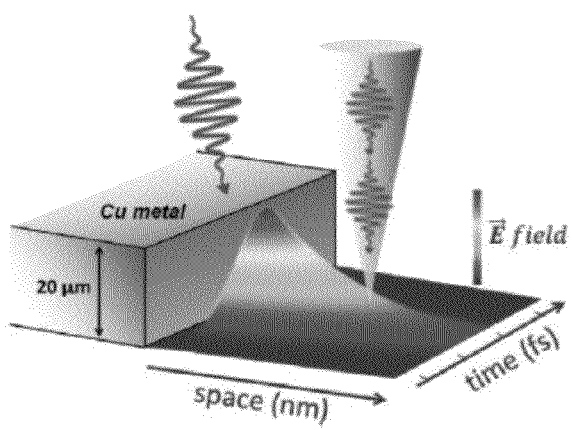
Figure 18D:
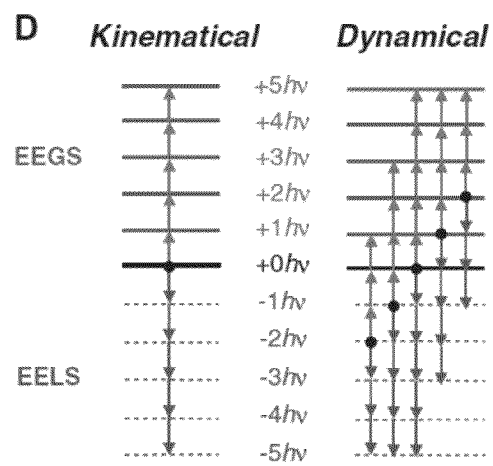

The phenomena discussed so far involved weak electric fields. In order to go beyond this regime, we have also studied the Cu metal-vacuum interface, for which the plasmonic field is strong in the vicinity of the interface. Compared to the Ag nanoparticle, the Cu slab is semi-infinite in the lateral direction and, therefore, higher charge (and field) densities are expected to accumulate at the interface upon excitation with linearly polarized light. Regions that were in close proximity to the interface were inaccessible before, but with the convergent ultrafast electron probes, they can now be studied. FIG. 18 shows probe scans at the Cu metal-vacuum and Ag nanoparticle-vacuum interfaces. FIG. 18A illustrates a schematic of the fs electron-probe scanning following the excitation of the Cu slab together with 3D field behavior. FIG. 18B illustrates the energy level diagram in the kinematical and dynamical photon-electron exchange regimes. FIG. 18C illustrates the normalized USI intensity (at t=0) vs. probe distance from the interface for the two systems studied; note the distinct difference between the particle and slab behavior. The Ag nanoparticle scan was taken outside and away from the highest-intensity edge of the particle. The dashed line is an exponential fit to the particle data. FIG. 18D illustrates the intensity profile for the different orders studied; the origin of spatial confinement as the order increases is shown, as observed experimentally (circles) and calculated theoretically (solid lines). The intensity of experimental data points were normalized to the total integrated intensity of their respective spectra.

FIG. 18A depicts schematically the probing arrangement of the interface. We note that cathodoluminescence can provide spectral responses with nanometer spatial resolution, however it is limited to radiative emission modes and, more importantly, the processes are caused by electron impact, not photon excitation.

Unlike the case of the Ag nanoparticle, we observed two regimes of interaction at the Cu-vacuum interface, which we term "dynamical" and "kinematical" EEGS; these dominate in the strong and weak field regimes, respectively. The analogy with diffraction terminology reflects the number of particles involved; for our case here it is a single photon process and in diffraction it is a single electron scattering event. The strong field limit can be seen in the results shown in FIG. 17B, where seven EEGS and EELS peaks were observed for the Cu metal-vacuum interface. This is in contrast to the Ag nanoparticle case where at most two orders were observed. FIGS. 18C and 18D show the probe position dependence of several EEGS orders, experimentally and theoretically, together, for comparison, with the interface-behavior of the Ag nanoparticle which has a decay length of 55 nm into the vacuum. When the USI intensity of the first order (+1hν) peak is plotted against the position of the probe we clearly observe a buildup and decay with a peak 100 nm away from the interface. The theory outlined above predicts such behavior for the first and higher orders (solid lines in FIGS. 18C and 18D). Physically, this behavior is due to the collective exchange of photons (see FIG. 18D) when the field is strong at the interface; 100 nm away, the field reaches the threshold intensity for the kinematical regime, i.e., the single photon-electron exchange. Thus, the buildup is due to the depletion of the n=1 process with a concomitant rise in higher order n≠1 processes, till reaching the threshold at 100 nm. Another feature that is prominent for higher orders is the inclination in time-energy maps (FIG. 17B, dashed line). This feature is a result of the chirp of electron pulses but we do not analyze it in detail here.

Thus, embodiments provide methods and systems related to ultrafast spectrum imaging in 4D electron microscopy. Both the spectral and temporal resolutions are now determined by the laser field, not the microscope-limited values of ms and sub-eV, respectively. The spatial resolution, which is nanometer scale, can be extended further to the atomic scale. High-order gain imaging can be exploited to further enhance the spatial localization and temporal response, as demonstrated above. These combined dimensions of USI enable applications in various domains, including those of molecules, particles and cells.

Embodiments provide for the visualization of entangled particles, separated by as large as 70 nm, and the discovery of channels in their near-fields. For silver nanoparticles, the induced field of each particle extends to 50-100 nanometers, but when particles are brought close in separation we observe channels as narrow as 6 nm, a width that is two orders of magnitude smaller than the incident field wavelength. The field gradient in the channels reaches $10^5$ V/cm per nm, and their direction can be controlled by the polarization of the incident field, particle size, and separation. Thus, embodiments enable the direct visualization of these nanoscopic near-fields, with the high spatial, temporal, and energy resolutions provided by the methodology given here.

Nanoparticles at nanoscale separations can, in principle, interact with each other, and if this interaction is coherent, constructive or destructive interferences may result in an entanglement through their fields. Visualization of such entanglement of electric fields on the nanometer scale is a nontrivial task, mainly because the wavelength of the optical field used is hundreds of nanometers whereas the scale for the interference is only a few nanometers. Moreover, it is essential that the resolution in both space and time be appropriate for visualization to be achieved. If realized, however, the imaged electric potentials with a high field gradient can be manipulated for different particle shape and orientation, with implications for various applications such as, e.g. trapping with ponderomotive force, optical tweezers, design of photonic and plasmonic devices, and even biological communications. It is, therefore, fundamental to observe these fields when particles approach each other and to uncover the nature of interactions between them.

Here, we report the visualization of particle-particle interaction and the discovery of particle entanglement with void-field channels in the observed electric field between them. The induced near-fields of nanoparticle pairs and chains were imaged using 4D electron microscopy, thus enabling the nanometer precision and femtosecond time resolution for visualization. Since the response of the nanoparticle system is to the linear polarization of the incident field, it was possible to control the dipolar particle polarization. For nanoparticles of typically 50 nm radius, the entanglement, despite the diffuseness of the field, results in very narrow channels, as narrow as 6 nm in width, an order of magnitude smaller than the spatial extent of the field for individual particles and two orders of magnitude smaller than the wavelength of the incident field. The channel orientation and shape can be tuned with the linear polarization of the exciting field, the size of the particle, and separation between them.

The above mentioned visualizations are not possible without the technique of photon-induced-near-field-electron-microscopy (PINEM). When convergent nanoscale electron beams are used, instead of parallel beams, it is possible to form ultrafast spectrum images to map out the near-fields with sub-particle resolution. Both methods provide the very high spatial (nm) resolution, but with the energy resolution and selectivity of optical techniques (meV), and with the temporal resolution being in the femtosecond (fs) domain. By comparison, light-based methods, such as near-field scanning optical microscopy, have spatial resolutions in the hundred nanometer range. On the other hand, electron microscopic techniques, such as energy-filtered (parallel beam) imaging and spectrum (convergent beam) imaging, have the needed spatial resolution, down to the atomic scale, but without the capabilities of polarization, ultrafast temporal, and selective-excitation control.

Here, an ultrashort (fs) optical pulse excites the material and induces near-fields in the vicinity of nanoparticles. Synchronously, an ultrashort (fs) electron pulse images the induced field that rises and falls on the fs time scale. It is this femtosecond time scale that enables the arresting of the field at high peak amplitudes. An inelastic energy exchange between the temporally-arrested field and the ultrafast electron results in electron energy-gain (absorption) or energy-loss (emission) at integer multiples of the photon energy. Since these inelastic scatterings take place only in the presence of the near-field, it is possible to map out the spatial distributions of these fields by recording the scattered electrons. This is achieved by a post-column spectrometer in our microscope, where only the energy-gained electrons are selected to form the image; see supporting online material for the experimental methods. We note that in PINEM, the excitation and polarization of the field are controllable features, unlike in conventional electron microscopy methods where the fields are induced by the imaging electrons. For this electron excitation case, all modes of the near-field may be produced, and entanglement may be obscured.

When two nanoparticles are brought in close proximity to each other, as shown in FIGS. 19A-C, entanglement may take place through their fields. FIGS. 19A and 19B illustrate entangled particles by dipolar fields and nanometer-scale void-channels. Shown are the near-fields of a nanoparticle pair with an edge-to-edge distance of 32 nm (FIG. 19A), 47 nm (FIG. 19B), and 250 nm (FIG. 19C) with false-color mapping. The well separated particles in (FIG. 19C) exhibit dipolar-like fields and at this 250 nm separation they do not interact. In contrast, when the separation is reduced to 32 nm or 47 nm a "channel" is formed between the particles as seen in (FIG. 19A) & (FIG. 19B). The bright field images of the nanoparticle pairs (obtained in UEM) are shown in the inset at the bottom right of (FIG. 19A) & (FIG. 19B); PINEM images are displayed at a higher magnification than the bright-field UEM images in order to emphasize the particles entanglement. The magnification in (FIG. 19C) is half of that in (FIG. 19A) & (FIG. 19B), and it is the same for both the PINEM and UEM images. The false-color bars are shown at the bottom left of (FIG. 19A) & (FIG. 19B); white (left) indicates the lowest intensity and red (right) the highest. Polarization of the exciting laser field is at 45° counterclockwise for (FIG. 19A) & (FIG. 19B), and it is horizontal for (FIG. 19C).

The total electric field at any point in space (x, y, z) and at time (t) is the coherent vectorial sum of the particles' fields; i.e., $$E'^{coherent}_{total} = E'_1(x,y,z;\tau) + E'_2(x,y,z;\tau). \tag{15}$$

It follows that interference of the particles' fields described vectorially in Eq. (15) will result only when phases are preserved, the coherent regime $|E_1+E_2|$, as oppose to the case of the incoherent addition of fields, $|E_1|+|E_2|$. At separations larger than the field decay length of a single particle, the electric fields do not interact significantly, and the observed images are those of two separate dipoles. This is shown in FIG. 1 C, in which the particles are separated by 250 nm. It is evident that the two dipolar lobs of each particle are similar in size, which demonstrates that the near-field interaction is nearly absent.

On the other hand, when particle separation becomes comparable to or less than the decay length, the near-fields interfere and channels open up between the particles, as shown in FIG. 19A and FIG. 19B. The shape and width of this unique channel depend on the particle separation and polarization. As the edge-to-edge distance increases from 32 nm to 47 nm, the width of the channel was observed to increase from 11 nm to 20 nm; the channel eventually disappears at large separations. Importantly, these channels are formed in the space between the two particles. As seen in the bright field images (insets in FIGS. 19A and 19B), there is nothing in the space between the particles, yet, in the PINEM images high contrast is observed in the in-between space.

In FIG. 20, the polarization effect and the change of the channel orientation for various angles is shown. FIG. 20 illustrates the polarization dependence of the entanglement. When the exciting optical pulse is polarized vertically, the channel is only along the horizontal direction and the resulting structure looks like a "dumbbell" (FIG. 20B). When the linear polarization is rotated on either side, the channels observed in FIG. 1 are retrieved, (FIG. 20A) & (FIG. 20C). Induced electric charge distributions on the nanoparticles are indicated in (FIG. 20D), and it is seen that the void-channel is "attached" to the particles near the zero-charge points. Particle separation is 20 nm (edge-to-edge). Intensities are shown in a gray scale. The intensity values for each image are normalized/stretched to fit the same intensity scale (0-255) after correcting for the top and bottom 1% intensity-outliers.

The change in contrast for all polarizations can be understood by considering the interference (or superposition) of the electric fields from the two particles, Eq. (15). Contrast is formed as a result of an energy exchange between the ultrafast electrons and the near-field component along the electron trajectory ($E_z$). At the center point between the dipoles, the $E_z$ contributions from the two particles are the same in amplitude and of opposite sign (i.e. they are out of phase) and, hence, they cancel each other. For the rest of the points on the axis of the nanoparticle pair (that is along the line connecting the two particles), the $E_z$ contributions are unequal (except for the case of FIG. 20B as discussed below) and, hence, the total $E_z$ is non-zero. Therefore, for the induced polarizations depicted in FIGS. 19A and 19B, and FIGS. 20A, 20C, and 20D, the channel is not a straight connection between the two particle edges but rather turns and follows the orientation of the linear polarization, as discussed below. We note that the contrast inside the nanoparticle is determined mostly by the diffraction loss of the transmitted electrons through the nanostructure; see supporting online material.

Further insight into the mechanism of channel formation can be gained by analyzing their polarization dependencies. In FIG. 20, the linear polarization of the excitation pulse was rotated in the lateral plane, and the figure shows the entanglement at four different polarization angles (particle separation is 20 nm). When the electric field of the 519 nm laser is aligned vertically (ϕ=0°), the channel stretches between the nearest points of the particles, and the resulting shape resembles a "dumbbell", very similar to the experimental observation close to ϕ=0° (ϕ=−5°). When it is rotated by ϕ=−35° (clockwise) and ϕ=+30° (counter-clockwise), shapes similar to those presented in FIG. 1 are retrieved, with the twist of the void-channel following the direction of the polarization vector.

This observed polarization behavior can be understood by considering the induced electric charge distributions, which are shown schematically at the peak of one optical cycle in FIG. 20D for the ϕ=+45° polarization. Because the particles are small compared to the wavelength of the exciting field, its electric field drives the conduction band electrons of the silver particle to create plus (+) and minus (−) charge accumulations at the opposite surfaces of the particle, while the plane that is orthogonal to the polarization vector (and passes through the center of particle) remains without any net charge. We call points on this latter plane at the boundary of the particle the zero-charge-points, one of which for z=0 is shown for each particle in FIG. 20D. Both particles in the pair have the same symmetry in their charge distributions; here the effect of the induced field of one particle on the charges of the other particle is not considered.

As we rotate the polarization, the zero-charge-points move on the perimeter of the disc defined by the lateral cross section of the particle. Importantly, the motion of the points on the adjacent edges of the two particles will be in opposite directions. In the dipole approximation, which is satisfied here, the $E_z$ of individual particle fields are null on their zero-charge-points. Therefore the total $E_z$ field approaches zero at these points. Since $E_z$ also equals zero at the high-symmetry point mentioned above (the center point between the two particles), it follows from the continuity of the fields that a void-channel connecting these three points will be formed. Indeed, this is what is experimentally observed—the joining points of the channel to the particles are near the zero-charge points. As for the polarization dependence, since the two points (the zero-charge points) move with the polarization direction while the third point (center of the two particles) remains the same, the channel rotates with the rotating polarization.

The striking very narrow width of the channel, as a result of the entanglement, is displayed in FIG. 21A. FIG. 21 illustrates the spatial extent of entanglement and channels of particle chains. The cross section across the channel of two entangled particles (separated by 14 nm, edge-to-edge) is shown in FIG. 21A, where the image intensity is plotted as a function of distance along the dashed line shown in the inset; the centers of the two particles involved are given as dashed lines. It is evident that the width of the channel is only 6 nm, implying large electric field gradients. The near-fields and their interactions for a chain of four particles are shown in FIG. 21B; the scale bar in FIG. 21B is 100 nm.

Shown together with the PINEM image in FIG. 21 is a cross-section of the channel taken at its center and in the perpendicular direction (see the dashed line in the inset); the nanoparticle separation in this case is 14 nm. The cross-sectional plot depicts the width of the channel, 6 nm, which is only 1% of the excitation wavelength (519 nm) that creates the near-fields. At our incident fs-pulse peak fluence (3 mJ/cm$^2$) at the specimen, the field is 3·10$^6$ V/cm, giving a maximum field gradient of 10$^5$ V/cm per nm for the channel.

For a chain of particles, FIG. 21B shows the near-fields observed at two different polarizations. The presence of entanglement is apparent in the gaps between the particles. Again, the polarization dependence is consistent with the results of the two-particle entanglement discussed above.

From the fields between the top two particles it is evident that the channels are observable even when the particle separation is 70 nm. As importantly, for an assembly of particles one can manipulate their directions and presence by controlling the polarization and/or particle separation.

For quantification of the observed experimental images, we calculated the electric fields expected as well as the PINEM fields. The results are given in FIG. 22, which shows the theoretical calculations of fields of single and interacting particles. The exciting photon propagation is along z and its polarization is at 45° along the (++) and (−−) charges shown. Near field spatial distribution of $|E_z|$ of a nanoparticle in the lateral plane is shown at the top row of (A) for different height (z) values. The bottom row presents the fields of two interacting nanoparticles, where the formation of void-channels is clearly visible. The PINEM fields and their cross-section along the inter-particle axis are shown in FIG. 22B for single and interacting particles. These fields are connected to the electric fields shown in FIG. 22A through a Fourier transformation. Importantly, when the individual PINEM fields of two particles are summed incoherently (bottom-left) the void-channels are absent. They are formed only when the superposition is coherent (bottom-middle). The cross sections of F(x,y) of the individual particles (top-right) indicate that the real parts of the fields are out-of-phase between the particles, and the coherent superposition of these fields results in the void-channel (bottom-right). Image intensities are given in a gray scale. Particle positions are shown with zero-intensity (black) discs in all images.

Because the dipole mode is dominant in the image, the particle can be replaced in the calculations with a point dipole placed at its center. Other modes and fields are inherently excluded in the dipole (Rayleigh) case; for the more general treatment Mie theory can be invoked. The field component relevant here ($E_z$) and its spatial extent in the image (x-y) plane, at various height (z) values, can be written as, $$E_z(x, y, z; t) \approx E_0 a^2 \chi(\omega) \frac{3xz}{r^2} e^{-i\omega\Lambda_z} \quad (16)$$

for x-polarization and with r=(x$^2$+y$^2$+z$^2$)$^{1/2}$. In Eq. (16), $E_\in$ is the amplitude of the incident field, a the particle radius, and χ(ω)=[∈(ω)−1]/[∈(ω)+2] where ∈(ω) is the complex dielectric function of the material (silver in this case) at the incident field's frequency (ω). Note that since ∈(ω) is in general a complex quantity, $E_z$ (even at t=0) will be complex as well, having a well-defined amplitude and phase.

Figure 22A:
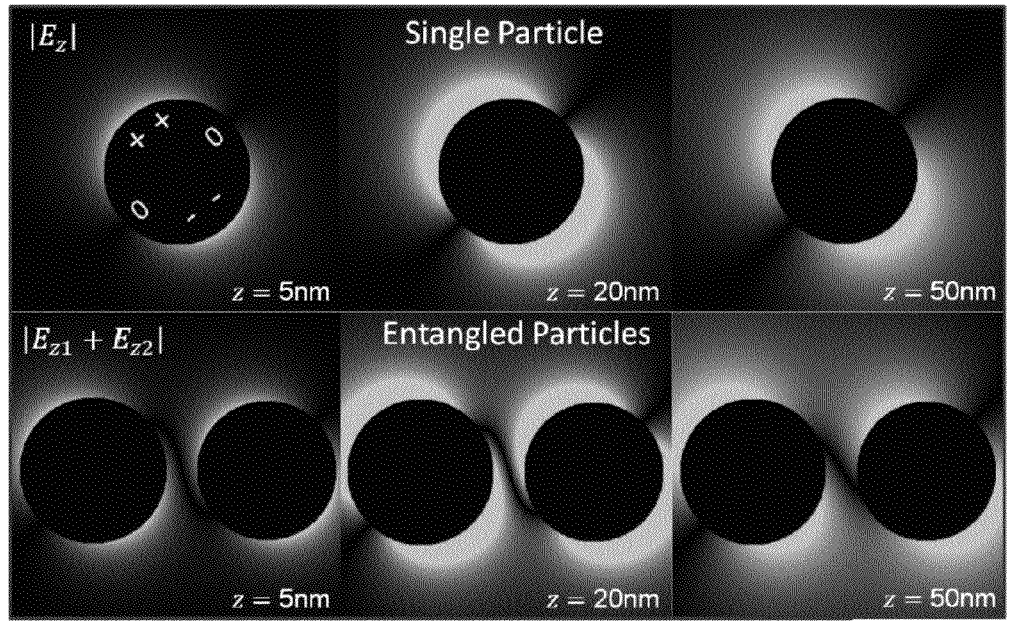
FIGS. 22A-B illustrate theoretical calculations of fields of single and interacting particles according to an embodiment of the present invention.
Figure 22B:
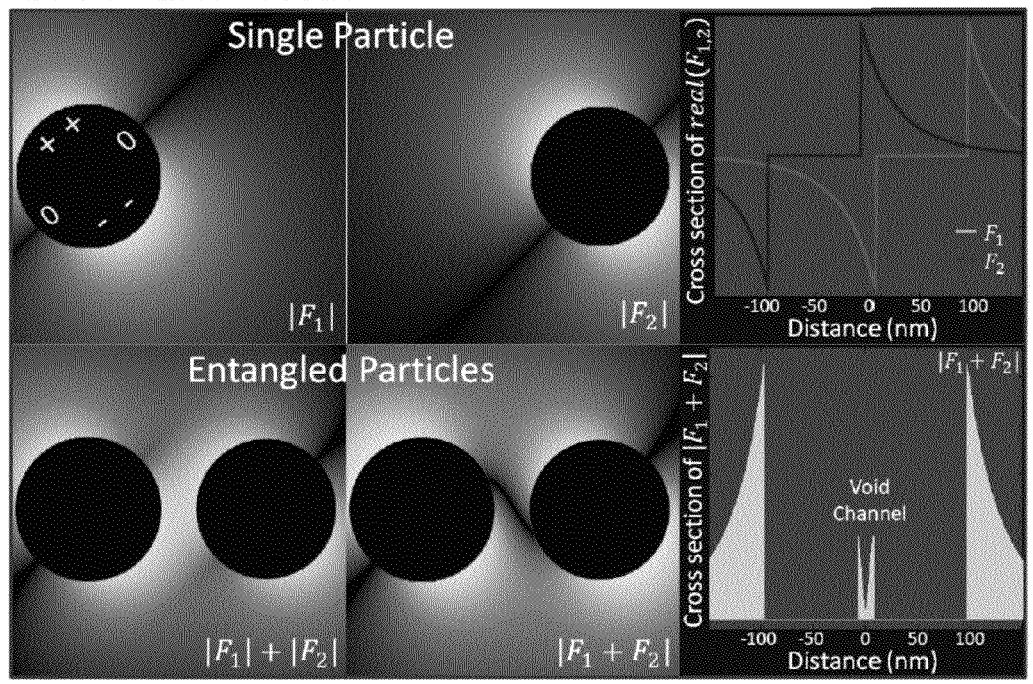

FIG. 22A gives the calculated $E_z$ value in the x-y plane for three different z values, and for a single and pairs of interacting particles. Fields are calculated using Eq. (16) at =0, and when the polarization is rotated from the vertical axis (ϕ=+45°). The last term in Eq. (16) represents the temporal cycling of the field; the experimental delay time is incorporated in $E_0$ and defines the t=0 for imaging in PINEM. Single particle images show the dipolar lobs and their strength is minimum when z is close to zero (z=0 is the plane that passes through the center of the particles and is orthogonal to the trajectory of incident photons and electrons along z). As the z value increases, the lob intensity increases (z=20 nm) but then falls for larger values (z=50 nm); the same behavior is reproduced in the lower half-space, i.e. for z<0, due to the symmetry in z, Eq. (16). Interaction of the two particles is calculated from the single particle dipole fields but using the superposition of the fields. The results are presented in the bottom row of FIG. 4A. Indeed, the channels emerge in the near-field region between the particles.

In order to compare the fields to the observed images we evaluated the PINEM field, which can simply be obtained by integrating $E_z(x,y,z,;t=t_e)$ along z, from $-\infty$ to $+\infty$. This is equivalent to the work done on the electron by the induced electric field. Because $E_z$ oscillates in time (the $e^{-i\omega t}$ term) the field couples to the electron's motion during its transit time, i.e. when $t_e=(z/v)$, where v is the speed of the electron, in this case 0.7 c at 200 keV. This substitution enables calculation of the PINEM field, and in this dipole case it is simply, $$F(x, y) \approx \int_{-\infty}^{+\infty} E_z(x, y, z) e^{-i\frac{\omega}{v}z} dz, \quad (17)$$

which states that PINEM fields are the Fourier transform of $E_z(x,y,z;t=0)$ at a fixed component of $\omega/v$, a consequence of momentum conservation in the scattering process. The PINEM intensity is simply given by the square of $F(x,y)$.

FIG. 22B (top row) depicts the field $F(x,y)$ for two single particles together with the cross sections along the horizontal axis through the centers of the particles. The images depict the magnitude of $F(x,y)$, and they closely follow the x-y distribution of the electric fields (FIG. 22A). Shown in the bottom row of FIG. 22B is the case of two interacting particles. The channel is evident only when the coherent superposition is appropriately calculated with the phases included $|F_1+F_2|$, not the incoherent sum $|F_1|+|F_2|$. To elucidate the origin of the channel narrowness it is helpful to plot the cross-sectional real parts. The panel on the right (FIG. 22B) indicates the opposite sign for each particle's field (top), and the very narrow spatial change of the field sign (between particles) to yield the narrow channel, as observed experimentally. When the incoherent summation is performed, $|F_1|+|F_2|$, the channels are no longer present and the particles do not entangle.

The discovery of nano-scale channels in the fields of entangled particles, together with the ability to visualize them in space and time, provide the opportunity to unravel fundamentals of microscopic interactions between particles of materials and of biological assemblies. The reported continuous channels with a width of a few nanometers, two orders of magnitude smaller than the wavelength of the incident field, have their potential applications in the control of particle properties, including charge flow, in nano-scale materials science in biological channels and self-assembly.

Embodiments provide a technique for in situ visualization of the biomechanics of DNA structural networks using 4D Electron Microscopy. Vibrational oscillations of the DNA structure are excited mechanically through a short burst of substrate vibrations that is triggered by a laser pulse. Subsequently, the motion is probed with electron pulses to observe the impulse response of the specimen in space and time. From the frequency and amplitude of the observed oscillations, we determine the normal modes and eigenfrequencies of the structures involved. Moreover, by selective "nano-cutting" at a given point in the network, it was possible to obtain Young's modulus, and hence the stiffness, of the DNA filament at that position. This experimental approach enables nanoscale mechanics studies of macromolecules and has applications in other domains of biological networks such as origamis.

In macroscopic engineering of structures, the nature of mechanical motions is critical for their robustness and function, as evidenced in the design of colossal structures, from the Pyramids to the Eiffel Tower. Our modern-day quest for miniaturization has led to the construction of ever more sophisticated nanoscale structures and devices, defining new frontiers in materials science and nanotechnology. Biological nanostructures and nanomachines have also attracted considerable interest, and efforts are directed at harnessing their power for the construction of devices with novel functions. A prominent example is DNA nanotechnology, which exploits the fact that DNA can be programmed and made to self-assemble into complex structures and functional devices. For all of these structures and applications, the need continues for the development of suitable tools that enable the visualization of these nanoscopic systems and the control of their properties.

Ultrafast Electron Microscopy (UEM) has been developed to directly visualize nanomechanical motions in space and time. The applications span a range of materials properties, including the drumming of a thin graphite membrane, the vibrations of carbon nanotubes, molecular nanocrystals, and bimetallic nanostructures fabricated with nanoelectromechanical systems (NEMS) technology. While it appears promising to extend the approach to the investigation of the material properties of individual biological nanostructures, several additional challenges had to be overcome.

In UEM experiments, a short laser pulse is used to excite the specimen and trigger coherent motions, which are probed with the electron pulses. However, many biological systems do not possess a suitable chromophore and may be susceptible to photodamage, as we expect for the DNA nanostructures investigated here. The dynamics are usually recorded in stroboscopic mode, i.e. a single time frame is obtained by repetitive recording (here, on the order of $10^4$ individual experiments are averaged), and bleaching of the chromophore and accumulated damage due to excited-state reactions and laser-induced heating may severely limit the feasibility of direct imaging. Moreover, for biological structures of nanoscale thickness that do not absorb significant amounts of light, the question remains of how mechanical oscillations would be induced, and if they would be of sufficiently large amplitude.

Herein, in situ visualization of the mechanical properties of a DNA nanostructure and the direct measurement of its stiffness from the induced vibrational oscillations are described. The structures were created by stretching DNA over a hole embedded in a thin carbon film. Using the electron beam, we severed several of the filaments connecting it to the carbon support in order to obtain a free-standing structure that exhibits oscillations of sufficiently large amplitude and also lends itself to vibrational analysis. The mechanical motion is induced through an efficient methodology, which does not rely on the absorption properties of DNA and should be transferable to other biological studies. We employ a visible laser pulse to trigger a short burst of strain in the carbon substrate, which results in a sufficiently broad vibrational frequency spectrum, and in turn impulsively excites the oscillations of the nanostructure. This microscopic approach is analogous to the use of a hammer blow in order to excite the eigenmodes of a suspended macroscopic object whose oscillations are subsequently recorded as a function of time for deducing mode shapes and eigenfrequencies.

When a solution of λ-DNA is left to dry on a holey carbon film, the 48,502 bp bacteriophage DNA strands with a contour length of 16.3 μm form complex extended structures. Depending on the local concentration of DNA and the exact preparation procedure, we observe thin DNA membranes and filamentous structures that occasionally bridge the holes of the support film, as seen in FIG. 23A. FIG. 23A illustrates an electron micrograph of the DNA nanostructure suspended over a hole of the support film. FIG. 23B illustrates a free-standing structure made by cutting several filaments shown in FIG. 23B using a focused electron beam. Here, a crescent-shaped DNA sheet covers the lower part of a 2.5 μm diameter hole, with thin filaments (~20-30 nm diameters) extending to the top. Most of these nanostructures likely contain a mixture of different forms of DNA as well as ordered and amorphous domains.

Immediately after preparation, some DNA membranes showed selected area electron diffraction (SAED) patterns, which are consistent with the B form of DNA. It should be noted, however, that the structure of FIG. 23 had largely more time to dry, so we cannot draw definitive conclusions about the DNA form involved. We disconnected several filaments of the structure in FIG. 23A from the carbon support by cutting them with a focused electron beam. In the resulting structure (FIG. 23B), the free-standing filaments now slightly protrude from the plane of the carbon film, which is apparent from a tilt series. Furthermore, the DNA network connecting them to the crescent-shaped DNA sheet appears to have relaxed.

The vibrational properties of the DNA nanostructure of FIG. 22B was studied by directly imaging the oscillatory motion that it undergoes, following impulsive excitation with a picosecond laser pulse at 532 nm. FIG. 24 shows the transient behavior of the DNA nanostructure following laser excitation. (FIG. 24A) Dark field UEM images recorded at t-=−100 ns, t1=40 ns, and t2=110 ns. The displacement of the filament on the left in the direction of arrow (a) is shown in (FIG. 24B) as a function of time (data curve). A polynomial fit highlights the underlying slow drift motion of the filament. With this underlying movement subtracted (data curve in FIG. 24C), the horizontal displacement (h) of the circled feature can be well described by a simple sinusoidal function (sinusoidal curve in FIG. 24C).

FIG. 24 illustrates the transient behavior of the DNA nanostructure following laser excitation. (FIG. 24A) Dark field UEM images recorded at t-=−100 ns, t1=40 ns, and t2=110 ns. The displacement of the filament on the left in the direction of arrow (a) is shown in (FIG. 24B) as a function of time. A polynomial fit highlights the underlying slow drift motion of the filament. With this underlying movement subtracted (curve in FIG. 24C), the horizontal displacement (h) of the circled feature can be well described by a simple sinusoidal function.

FIG. 24A displays stroboscopically recorded dark field (DF) images of the structure at $t_-$=−100 ns (i.e. 100 ns before the arrival of the excitation pulse), $t_1$=40 ns, and $t_2$=110 ns. The displacement of the filament on the left in the direction of arrow (a) is shown as a function of time in FIG. 24B. It exhibits fast, fairly regular oscillations, superimposed on an slow aperiodic motion, which is highlighted by a polynomial fit of the data. We also observe this slow, irregular movement without laser excitation and therefore ascribe it to a drift motion of the filament, which occurs on the time scale of the experiment (~1 h). Calibration experiments indicate that the pulsed electron beam does not have a significant effect on this drift movement, suggesting a thermal origin for the drift. Subtracting this thermal background from the horizontal movement (h) of the circled feature in FIG. 24A, the data curve in FIG. 24C is obtained, which can be well approximated by a single sinusoidal function. Using the same procedure, we obtained the oscillations for the filament labeled (a) in FIG. 24A and for other sites in the network. The frequency spectra of the data are similar after background subtraction except, of course, for the reduced intensity of low-frequency features.

Other calibration experiments show that the DNA nanostructures can deform over time, especially when the pump laser power is made relatively high; the pulsed electron beam did not seem to cause noticeable damage. We also investigated of the effect of heating on the vibrational properties of the DNA structures. Despite some deformation that occurred after prolonged exposures to the pump laser beam, the vibrational frequencies of the investigated nanostructure remained unchanged to within 1%, while the vibrational amplitudes increased slightly.

FIG. 25 illustrates the vibrational properties of the DNA nanostructure. As indicated in (FIG. 25A), the displacement of different filaments in the directions of arrows (a-d) is analyzed as a function of time, as well as the vertical (e, g) and horizontal displacement (f, h) of the circled features. From the obtained transients, the slow drift motion of the structure is subtracted, and a time-frequency analysis with the MUSIC algorithm is performed (FIG. 25B). The pseudospectra were obtained for 500 ns long time windows and are shown with a logarithmic intensity scale. The shapes of the deduced vibrational modes of the DNA nanostructure are illustrated in (FIG. 25C), and their eigenfrequencies are given in MHz. The scale bars correspond to 200 nm.

We analyzed the vibrations of the DNA nanostructure of FIG. 23B by determining the deflection of the different filaments as a function of time (arrows (a-d) in FIG. 25A), as well as the vertical (e, g) and horizontal displacement (f, h) of the circled features. A time-frequency analysis of the obtained transients is shown in FIG. 25B. Pseudospectra were calculated for 500 ns long time windows and are displayed with a logarithmic intensity scale. The appearance of the spectra was found to be widely independent of the estimate of the signal subspace dimension; here an estimate of 23 was used (for 50 degrees of freedom).

The time-frequency analysis for the oscillations of the DNA filament on the left of FIG. 25A reveals a single oscillation frequency around 16.3 MHz (FIG. 25B, (a and b)). At long times, the second harmonic appears in the pseudospectra, which is likely an artifact introduced by the lower sampling rate that was used after about 1.7 μs. The higher spectral resolution provided by the MUSIC algorithm (as compared to, for example, a simple periodogram) reveals that the oscillation frequency varies over time within a range of about 2 MHz; in particular, it prominently decreases around 0.75 μs. Independent of which part of the filament is monitored (FIG. 25B (a and b)), almost identical changes of the frequency are observed, which renders it unlikely that they could be explained as an artifact of the data analysis. Since the observed frequency variation is generally not reproducible, we conclude that it occurs on the time scale of the experiment, similar to the drift of the equilibrium position of the filament. However, both phenomena do not appear to be correlated.

The oscillation frequencies associated with the movement of the bifurcated structure on the right of FIG. 25A appear more stable (FIG. 25B (c-h)). By identifying frequencies common to different parts of the DNA nanostructure, we can attempt an assignment of its normal modes, which is illustrated in FIG. 25C. This analysis reveals that the ~16 MHz oscillation of the single filament on the left of FIG. 25A is uncoupled from the rest of the structure. The double-headed arrow indicating the mode shape in FIG. 25C suggests an in-plane oscillation, however, we note that the oscillation might have an out-of-plane component that we cannot observe in projection. The bifurcated DNA structure exhibits two collective low-frequency oscillations. The entire branch swings in-plane with a frequency of ~8 MHz, which is common to the deflection of the filaments (c and d) and the horizontal displacement of the circled features (f and h). Their vertical displacement (e and g) shows a common ~4 MHz oscillation, which indicates an out-of-plane motion of the branched structure. Furthermore, the loose ends of the branch (c and d) exhibit oscillations with frequencies of ~28 and ~15 MHz, respectively. While the weak ~15 MHz vibration seems to be isolated, the ~28 MHz oscillation is slightly delocalized and also appears weakly in the frequency spectra of the horizontal displacements (f and h).

The vibrational frequencies of the free-standing filaments can be used to obtain Young's modulus of the DNA structure. The filaments were approximated as prismatic beams of circular cross section, clamped at one end and free at the other; their vibrations are largely isolated from the remaining structure. For this cantilever case, Young's modulus, Y, can be obtained from the equation, $$Y = \left(\frac{8}{\pi \cdot 1.194^2} \cdot \frac{f \cdot L^2}{\kappa}\right)^2 \cdot \rho,$$

where the frequency of the fundamental mode is f, the length of the beam is L, its density is $\rho$, and the radius of gyration is $\kappa$=r/2; r is the beam radius. When we determine L and r from FIG. 24B and assume the density $\rho$=1.23 g/cm$^3$ of dehydrated DNA, as discussed below, we obtain a modulus of 15±3 GPa for the isolated filament, as well as 12±3 and 11±3 GPa for the left and right filament of the bifurcated structure, respectively.

These values are considerably higher than the modulus of about 300 MPa that was determined in single-molecule stretching experiments in solution. However, Brillouin scattering studies have previously found that at low levels of hydration, the modulus of DNA films strongly increases up to values of 9.3-11.6 GPa at a relative humidity of 23%. Our results are therefore consistent with a low level of DNA hydration, and this justifies our choice of the value for the density of DNA. Stiffening as a result of dehydration has been observed for different types of biological materials. In the case of DNA, it has been attributed to a combination of different effects. An increase of the strength of interhelical interactions appears to play an important role, which occurs when the distance between neighboring DNA strands decreases upon removal of interhelical water and the Coulomb interaction of their phosphate groups becomes stronger.

Close inspection of the frames in FIG. 24A reveals that the appearance of the single filament on the left changes with time. While it appears sharp before time zero (t_), the images at short times show strong blurring (t$_1$), which then decreases at later times (t$_2$). These images suggest the excitation of higher-order vibrational modes which manifest as image blurring before damping out. The broad band of frequencies excited at early times gives a hint to the nature of the excitation mechanism which we discuss below.

When an inhomogeneous cantilever such as a bimetallic nano-strip is heated, it acts as a thermostat A laser-induced temperature jump will impulsively change its equilibrium position, so that it begins to oscillate. This excitation mechanism cannot be as effective for cantilevers consisting of homogeneous materials such as DNA. A sudden change of the equilibrium position leading to transverse oscillations can nevertheless be induced if the laser beam is sufficiently attenuated while passing through the cantilever and the material strongly expands or contracts as a result of photon absorption. In this case, an inhomogeneous strain profile is created along the direction of the laser beam, so that the cantilever starts to oscillate about its new equilibrium position.

Weakly absorbing, thin biological specimens would not lend themselves easily to this excitation mechanism, especially if they are sensitive to heat and high pump laser powers must be avoided. Since DNA is transparent at visible wavelengths, we can exclude its direct excitation with the laser pulse. It is also unlikely that the strongly absorbing carbon substrate would rapidly heat the DNA structure and mediate a temperature jump. Using published values for the thermal conductivity, specific heat capacity, and density of DNA, one can estimate that the DNA membrane, which connects the filaments to the carbon support, heats up on a timescale of about 100 ns after the substrate undergoes a temperature jump, far too slow to explain the oscillations of the filaments that set in promptly after the laser pulse.

In order to shed light on the excitation mechanism, we conducted the following series of experiments. FIG. 26 illustrates the distance dependence of DNA mechanical vibrations. The out-of-plane vibration of the DNA nanostructure in (FIG. 26A) is monitored by tracking the vertical displacement of the circled feature. (The bar corresponds to 300 nm.) The low-magnification micrograph in (FIG. 26B) indicates the location of the structure (circle) relative to the position of the laser focus (dots with the circles representing the beam diameter of 40 µm FWHM). The displacement of the tracked feature as a function of time is shown in (FIG. 26C) for the different laser focus positions. The curves corresponding to the smallest and largest distance between structure and laser spot are highlighted. The amplitude and time delay of the first maximum (marked with an arrow) are extracted from a fit with a sinusoidal function and plotted as a function of the distance between structure and laser focus in (FIG. 26D) and (FIG. 26E), respectively. From a linear fit to the data points in (FIG. 26E), the speed of sound in the substrate is obtained to be v=14±3 km/s.

Figure 26A:
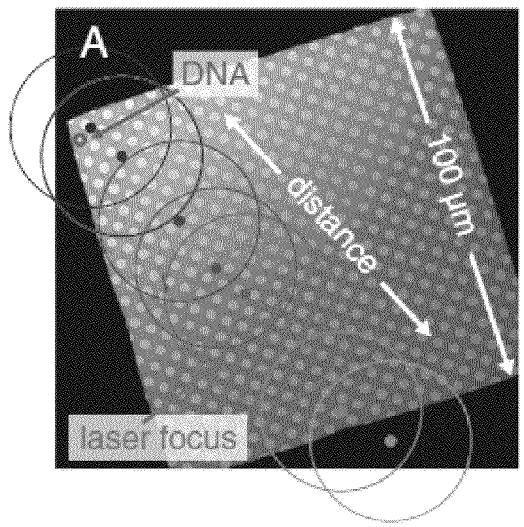
FIGS. 26A-E illustrate the distance dependence of DNA mechanical vibrations according to an embodiment of the present invention.
Figure 26B:
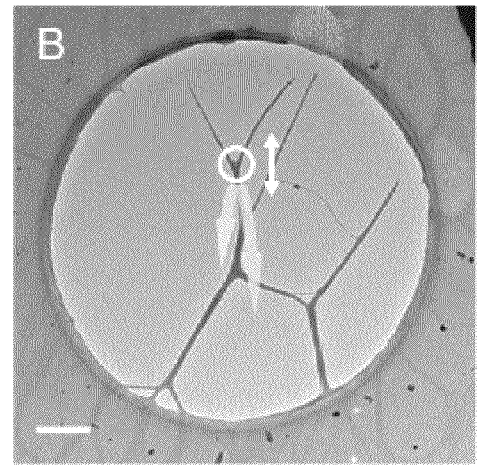
Figure 26C:
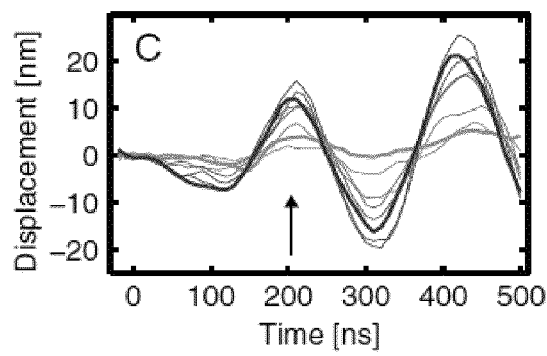

The low-magnification image in FIG. 26A shows a DNA nanostructure (circle) in the upper-left corner of a square area of the holey carbon film, which is surrounded by the copper bars of the support mesh. The distance between the DNA structure and the laser focus was successively increased. For each laser spot position (indicated by dots, with the surrounding circles representing the beam diameter of 40 µm), we recorded a movie covering the first 500 ns after laser excitation. An out-of-plane collective vibration of the tree-like DNA structure (FIG. 26B) was monitored by tracking the vertical displacement of the circled feature. This low-frequency mode is little affected by thermal drift motion, which is a prerequisite for the following analysis. FIG. 26C displays the displacement of the feature as a function of time for all eight laser spot positions, with two waveforms highlighted to correspond to the smallest and largest distance between the nanostructure and the laser focus. The data are presented with a three-point spline to reduce the amount of high-frequency noise.

In all eight experiments, we obtained waveforms of a similar shape, reminiscent of a driven oscillation, with the amplitude continually increasing during the first 500 ns. This behavior is inconsistent with a mechanism in which the pump laser pulse excites the DNA structure directly and induces oscillations, e.g., through inhomogeneous heating as discussed above. In this case, one would expect the oscillation to reach its maximum amplitude immediately, as for example observed for microcantilevers of Cu(TCNQ). In our case here, a driving force persists for at least 500 ns after the laser pulse.

Without limiting embodiments of the present invention, we believe that the oscillations of the DNA nanostructure are excited through vibrations of the holey carbon support that are triggered by the laser pulse. In fact, it has previously been reported that excitation of a 75 nm thick single-crystalline graphite film with a 532 nm laser pulse induces drumming motions with frequencies in the MHz range. Impulsive, local heating creates thermal stress, which initially leads to the excitation of vibrational modes with a broad band of frequencies. Rapid damping occurs, and at later times, only a few modes persist. It is conceivable that the holey carbon film (a composite of a 10 nm layer of amorphous carbon on a 10 nm layer of organic polymer, supported by a copper mesh) should show a similar response to laser excitation, although we expect its oscillations to dampen out more rapidly due to the inhomogeneity of the material. Since the DNA nanostructure is mechanically connected to the support film, its eigenmodes will be excited if the frequency spectrum of the substrate vibrations covers the range of their eigenfrequencies. The fact that oscillations of the DNA structure are excited even though the laser focus is positioned at a distance of more than 100 μm (while the laser spot diameter is only about 40 μm) lends further support to the proposed excitation mechanism. Evidently, the carbon substrate transfers the excitation energy to the structure.

Figure 26D:
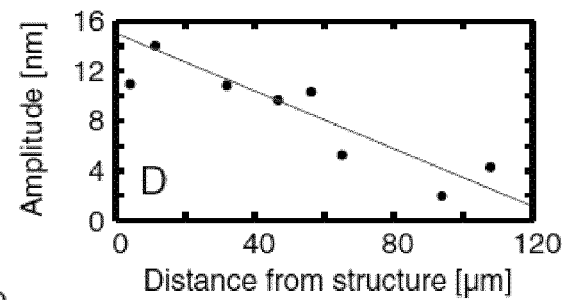
Figure 26E:
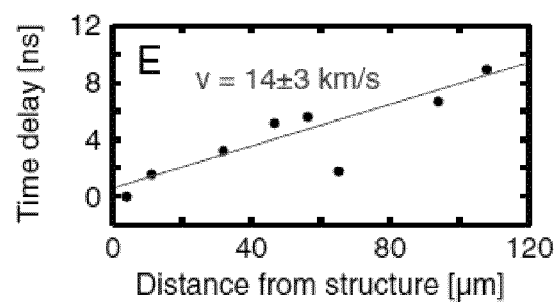

For the purpose of a quantitative analysis, we measured the distance between the structure and the laser focus in μm and determined the amplitude in nm and time delay in ns of the first maximum of the vibrational waveform (marked with an arrow in FIG. 26C) from a fit with a sinusoidal function. We can thus determine the spatial extent of the induced vibrations (stress) in the substrate as well as their speed of propagation. As shown in FIG. 26D, the amplitude decreases as a function of the distance, which supports the notion that the oscillations of the holey carbon film have their maximum amplitude at the center of the laser spot where the thermal stress is greatest. The time delay of the oscillation increases with distance (FIG. 26E). From a linear fit, the speed of sound in the holey carbon film was deduced giving v=14±3 km/s, which agrees favorably with the speed of 8.7-14 km/s measured in amorphous carbon thin films. This result further supports the suggested acoustic excitation mechanism; the laser pulse induces a short burst of strain vibrations in the substrate, which in turn impulsively excite mechanical oscillations of the structure of interest.

Thus, embodiments provide for nanoscale imaging of the biomechanics of DNA structures. Our approach enables the determination of vibrational normal modes and eigenfrequencies, as well as Young's modulus of free-standing DNA filaments that exhibit isolated oscillations. The mechanical oscillations of the DNA structure are excited through vibrations of the holey carbon following an impulsive excitation with a clocking laser pulse, even at a distance from the DNA structure. This excitation scheme avoids photodamage, since it does not require photon absorption of the DNA itself and the excitation can be made tens of microns away from the structure. The pulsed electron beam did not induce damage, possibly because of its short duration relative to the repetition rate. Lastly, the values obtained for Young's modulus indicate that the DNA structure is fairly dehydrated. An environmental cell should allow one to control the level of hydration. Our technique, building on the capabilities of 4D Electron Microscopy, can visualize the mechanics of complicated nanoscopic structures in space and time and is applicable in the study of other biological nanomaterials.

DNA nanostructures were prepared using a solution of λ-DNA (Takara Bio Inc.; 200-500 μg/mL, 10 mM Tris-HCl, pH 8.0, 1 mM EDTA) that was diluted by a factor of 50 with deionized water (with a resistivity of 18 MΩcm at 25° C.), and a drop of 5 μl was placed onto a Quantifoil holey carbon film with 2.5 μm diameter holes that had been rendered hydrophilic in an argon/oxygen plasma. After incubating for 5 min, the solution was wicked away with filter paper, and the sample was washed twice with 3 μl of deionized water before it was allowed to dry.

The resulting DNA nanostructures were imaged and manipulated by electron beam cutting in our ultrafast electron microscope, UEM-1. Time-resolved experiments were carried out in stroboscopic acquisition mode. Briefly, the vibrational dynamics of the DNA nanostructures were triggered with 532 nm picosecond laser pulses that were focused onto the specimen (16 ps FWHM, 0.25 μJ pulse energy, 40 μm FWHM spot size). A 266 nm nanosecond laser (10 ns FWHM), synchronized to the pump laser with a digital delay generator (25 ns jitter), produced photoelectron pulses that were used to image the structure at a given delay after excitation. Frames recorded every 10 or 20 ns were then used to construct a movie. Experiments were carried out with a repetition rate of 1 kHz (which ensured that oscillations had subsided before the beginning of the next cycle) and an acquisition time of 15 s per frame. Images were recorded in centered dark field (CDF) mode, with the tilt angle of the incident electron beam optimized for maximum contrast.

Cross-correlation based image registration was used to align the movie frames relative to each other as well as to track the branching points of DNA structures. The deflection of filaments along a given line was determined by obtaining an intensity profile and fitting it with a Gaussian. For the analysis of the excitation mechanism, the position of the laser focus was determined by recording microscopic burns on a Quantifoil holey carbon film. The extrema of the vibrational waveforms in FIG. 4C were fit to the function, $$y = a + (b_0 + b_1 t) \cdot \sin(\omega t + \Phi),$$

where y is the displacement, t the time, and a, $b_0$, $b_1$, $\omega$, and $\Phi$ are fit parameters. For the determination of Young's modulus, we obtained the length of the filaments from FIG. 23B by measuring the distance from their tip to their point of attachment to the nanostructure. As they slightly protrude from the plane of the holey carbon film, we are bound to somewhat underestimate their length. Their radii were determined from intensity profiles measured orthogonal to the filament tangent along its entire length. The profiles were aligned with respect to each other using the cross-correlation methodology.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A microscope system comprising:
   a microscope column;
   an electron beam path disposed within the microscope column, wherein the electron beam path impinges on a specimen disposed in the microscope column;
   a laser beam path operable to support a laser beam and disposed both external to and within the microscope column, wherein the laser beam path impinges on the specimen;
   a beam splitter disposed along the laser beam path and operable to split the laser beam into a specimen path and a detection path;
   a set of mirrors disposed along the detection path and optically coupled to the beam splitter, wherein the set of mirrors are oriented perpendicular to each other;

a turning mirror disposed along the detection path and optically coupled to a second mirror of the set of mirrors; and a detector optically coupled to the turning mirror.

2. The microscope system of claim 1 wherein the beam splitter comprises an uncoated fused silica element.

3. The microscope system of claim 1 wherein the set of mirrors and the turning mirror comprise fused silica elements having a thickness greater than a thickness of the beam splitter.

4. The microscope system of claim 1 wherein the beam splitter is oriented with an angle of incidence of about 45°.

5. The microscope system of claim 1 wherein:
the beam splitter and the turning mirror are operable to provide a first polarization reflection; and
the set of mirrors are operable to provide a second polarization reflection orthogonal to the first polarization reflection.

6. The microscope system of claim 1 wherein the specimen path and the detection path are characterized by an equal optical path length.

7. A microscope system comprising:
a microscope column;
a laser system operable to provide a laser beam;
an electron beam path disposed within the microscope column;
a window disposed in the microscope column;
a laser beam path disposed within the microscope column, wherein both the electron beam path and the laser beam path impinge on a specimen disposed in the microscope column at a predetermined position;
an optical system mounted in a fixed relationship to the window, wherein the optical system comprises:
a beam splitter operable to receive the laser beam, pass a first portion of the laser beam to the laser beam path, and pass a second portion of the laser beam along a detection path;
a set of mirrors disposed along the detection path and operable to receive the second portion of the laser beam;
a turning mirror disposed along the detection path and coupled to the set of mirrors; and
a detector, wherein the detection path impinges on the detector at a second predetermined position correlated to the predetermined position.

8. The microscope system of claim 7 wherein the second predetermined position is a surrogate of the predetermined position.

9. The microscope system of claim 7 wherein the second portion comprises an attenuation signal compared to the first portion.

10. The microscope system of claim 7 wherein the optical system provides for polarization compensation.

11. The microscope system of claim 7 wherein an optical path length from the beam splitter to the specimen is equal to an optical path length from the beam splitter to the detector.

12. A method of imaging a specimen, the method comprising:
providing a stage assembly configured to support the specimen;
generating a first train of optical pulses from a first laser source;
directing the first train of optical pulses along an optical path to impinge on a cathode;
generating a train of electron pulses in response to the first train of optical pulses impinging on the cathode;
directing the train of electron pulses along an imaging path to impinge on the specimen;
generating a second train of optical pulses from a second laser source;
splitting the second train of optical pulses into a specimen path and a detection path, wherein the specimen path and the detection path have equal optical path lengths;
directing the optical pulses in the specimen path to impinge on the specimen;
directing the optical pulses in the detection path to impinge on a detector after reflection from a set of mirrors and a turning mirror; and
detecting at least a portion of the train of electron pulses passing through the specimen.

13. The method of claim 12 further comprising blocking the optical pulses in the specimen path while concurrently directing the optical pulses in the detection path to impinge on the detector.

14. The method of claim 12 wherein the detector is operable to measure a polarization of the optical pulses in the detection path.

15. The method of claim 12 wherein the detection path comprises polarization compensating optical elements.

16. The method of claim 12 wherein a fluence of the optical pulses in the detection path is less than a fluence of the optical pulses in the specimen path.

17. The method of claim 12 wherein the first laser source and the second laser source are a same laser source.

\* \* \* \* \*